United States Patent
Chen

(10) Patent No.: US 9,193,778 B2
(45) Date of Patent: Nov. 24, 2015

(54) T CELL RECEPTORS SPECIFIC FOR IMMUNODOMINANT CTL EPITOPES OF HCV

(75) Inventor: Margaret Sällberg Chen, Stockholm (SE)

(73) Assignee: Tripep AB, Huddinge (SE)

(*) Notice: Subject to any disclaimer, the term of this patent is extended or adjusted under 35 U.S.C. 154(b) by 171 days.

(21) Appl. No.: 13/511,353

(22) PCT Filed: Nov. 23, 2010

(86) PCT No.: PCT/IB2010/003155
§ 371 (c)(1),
(2), (4) Date: Aug. 27, 2012

(87) PCT Pub. No.: WO2011/064664
PCT Pub. Date: Jun. 3, 2011

(65) Prior Publication Data
US 2013/0011375 A1  Jan. 10, 2013

Related U.S. Application Data

(60) Provisional application No. 61/264,155, filed on Nov. 24, 2009.

(51) Int. Cl.
| | |
|---|---|
| A61K 48/00 | (2006.01) |
| C07H 21/04 | (2006.01) |
| C07K 14/435 | (2006.01) |
| C12N 15/00 | (2006.01) |
| C12N 15/85 | (2006.01) |
| C07K 14/725 | (2006.01) |
| A61K 38/00 | (2006.01) |

(52) U.S. Cl.
CPC .......... *C07K 14/7051* (2013.01); *A01K 2207/15* (2013.01); *A01K 2227/105* (2013.01); *A01K 2267/0387* (2013.01); *A61K 38/00* (2013.01); *C12N 2740/13043* (2013.01); *C12N 2770/24211* (2013.01)

(58) Field of Classification Search
USPC .................. 424/93.1, 93.2; 435/69, 1, 320.1; 514/44; 536/23.1, 23.5
See application file for complete search history.

(56) References Cited

U.S. PATENT DOCUMENTS

| | | | |
|---|---|---|---|
| 4,745,051 A | 5/1988 | Smith | |
| 4,946,778 A | 8/1990 | Ladner et al. | |
| 6,511,830 B1 * | 1/2003 | Takahashi et al. | 800/4 |
| 2010/0015113 A1 * | 1/2010 | Restifo et al. | 424/93.71 |

FOREIGN PATENT DOCUMENTS

| | | |
|---|---|---|
| WO | WO 2007/056760 A2 | 5/2007 |
| WO | WO 2007/085814 A1 | 8/2007 |
| WO | WO 2009/132283 * | 10/2009 ............. A61K 39/00 |

OTHER PUBLICATIONS

Arden et al, Nature 316:783-787, 1985.*
Evavold et al, GenBank U46841; 2001.*
Strausberg et al, GenBank BC089553; 2009.*
Ahlen, G., et al. (2007) In vivo electroporation enhances the immunogenicity of hepatitis C virus nonstructural 3/4A DNA by increased local DNA uptake, protein expression, inflammation, and infiltration of CD3+ T cells, J Immunol 179:4741-53.
Alter, H. (2006) Viral hepatitis. Hepatology 43:S230-4.
Bowen, D. G., and C. M. Walker, (2005) Adaptive immune responses in acute and chronic hepatitis C virus infection, Nature 436:946-52.
Callender et al.,(2006) "Identification of a hepatitis C virus-reactive T cell receptor that does not require CD8 for target cell recognition", Hepatology, 43(5):973-981.
Chervin, A. S., et al., (2009) The impact of TCR binding properties and antigen presentation format on T cell responsiveness. J Immunol 1S3:1166-78.
Database EMBL [Online], "*Mus musculus* T-cell receptor alpha chain (TCRA) mRNA, partial cds", retrieved from EBI accession No. EMBL: AF012190, p. 2, passage "translation" and "sequence" compound, Aug. 26, 1997.
Fisher, D., Chap. 42 in: *Manual of Clinical Immunology*, 2d Ed. (Rose and Friedman, Eds.) Amer. Soc. For Microbiol., Washington, D.C. (1980).
Frelin, L., et al., (2003) Low dose and gene gun immunization with a hepatitis C virus non structural (NS) 3 DNA-based vaccine containing NS4A inhibit NS3/4A-expressing tumors in vivo, Gene Ther 10:686-99.
Frelin, L.. et al. (2004), Codon optimization and mRNA amplification effectively enhances the immunogenicity of the hepatitis C virus nonstructural 3/4A gene, Gene Ther 11:522-33.
Fytili, P., et al., (2005) Cross-genotype-reactivity of the immunodominant HCV CDS T-cell epitope NS3-1073, Vaccine 26:3818-26.
International Search Report and Written Opinion of the International Search Authority for PCT/IB2010/003155 dated May 25, 2011.
Kantzanou, M., et al. (2003) Viral escape and T cell exhaustion in hepatitis C virus infection analysed using Class I peptide tetramers, Immunol Lett 85:165-71.
Kronenberger, B., and S. Zeuzem, (2009) Current and future treatment options for HCV. Ann Hepatol 8:103-12.
Lechner, F., N. H. Gruener, S. Urbani, J. Uggeri, T. Santantonio, A. R. Kammer, A. Cerny, R. Phillips, C. Ferrari, G. R. Pape, and P. Klenerman. (2000) CD8+ T lymphocyte responses are induced during acute hepatitis C virus infection but are not sustained, Eur J Immunol 30:2479-87.

(Continued)

*Primary Examiner* — Kevin Hill
(74) *Attorney, Agent, or Firm* — Knobbe, Martens, Olson & Bear, LLP

(57) ABSTRACT

The present invention relates generally to the field of immunology. More particularly, aspects of the invention concern the discovery of several T cell receptors (TCRs) that are specific for an immunodominant CTL epitope of hepatitis C virus (HCV). Embodiments include TCRs, DNAs encoding TCRs, methods of making TCRs, and methods of using TCRs to treat, prevent or inhibit hepatitis C virus (HCV) proliferation.

25 Claims, 9 Drawing Sheets

(56) References Cited

OTHER PUBLICATIONS

Martin et al., (2004) "Genetic immunization and comprehensive screening approaches in identification of three novel epitopes in hepatitis C virus NS3 antigen", Journal of Medical Virology, vol. 74, No. 3, pp. 397-405.
Meyer-Olson, D. (2004) et al., "Limited T cell receptor diversity of HCV-specific T cell responses is associated with CTL escape", The Journal of Experimental Medicine, Rockefeller University Press, US, vol. 200, No. 3, pp. 307-319.
Nilges, K et al. (2003) Human papillomavirus type 16 E7 peptide-directed CDS+ T cells from patients with cervical cancer are cross-reactive with the coronavirus NS2 protein. J Virol 77:5464-74.
Ouchterlony, O. et al., Chap. 19 in: *Handbook of Experimental Immunology*, D. Wier (ed) Blackwell (1973).
Pascolo, S., N. et al., (1997) HLA-A2.1-restricted education and cytolytic activity of CD8(+) T lymphocytes from beta2 microglobulin (beta2m) HLA-A2.1 monochain transgenic H-2Db beta2m double knockout mice. J Exp Med 185:2043-51.
*Remmlngton's* Pharmaceutical Sciences, 15th Edition, Easton: Mack Publishing Company, pp. 1405-1412 and 1461-1487 (1975).
Rock, K. L., L. Rothstein, and S. Gamble, (1990) Generation of class I MHC-restricted TT hybridomas. J Immunol 145:804-11.
Roszkowski, J. J., et al., (2003) CDS-independent tumor cell recognition is a property of the T cell receptor and not the T cell, J Immunol 170:2582-9.
Sallberg, M et al., (1991) Rapid "tea-bag" peptide synthesis using 9-fluorenylmethoxycarbonyl (Fmoc) protected amino acids applied for antigenic mapping of viral proteins. Immunol Lett 30:59-68.
The National *Formulary XIV*, 14th Edition, Washington, American Pharmaceutical Association (1975).
Ward et al, (2002) "Cellular immune responses against hepatitis C virus: the evidence base 2002", Clinical and Experimental Immunology, vol. 128, No. 2 pp. 195-203.
Wertheimer, A. M., C. Miner, D. M. Lewinsohn, A. W. Sasaki, E. Kaufman, and H. R. Rosen, (2003) Novel CD4+ and CD8+ T-cell determinants within the NS3 protein in subjects with spontaneously resolved HCV infection. Hepatology 37:577-89.
Woitas et al., (2002) "Differential expansion of T-cell receptor variable beta subsets after antigenic stimulation in patients with difference outcomes of hepatitis C infection", Immunology, vol. 106, No. 3, pp. 419-427.
Colberre-Garapin, et al., (1981) "A new dominant hybrid selective marker for higher eukaryotic cells" *J. Mol. Biol.* Jul. 25; 150:1.
Cole et al. "The EBV-hybridoma technique and its application to human lung cancer," *Monoclonal Antibodies and Cancer Therapy*, Alan R. Liss Inc, New York N.Y., pp 77-96 (1985).
Cote et al. (1983) "Generation of human monoclonal antibodies reactive with cellular antigens." *Proc Natl Acad Sci* April; 80(7):2026-2030.
Davis, L. et al. (1986) "Monoclonal Antibody Production: Hybridoma Fusion" *Basic Methods in Molecular Biology*, Elsevier, New York. Section 21-2
Dayhoff et al., (1978) *Atlas of Protein Sequence and Structure*, vol. 5, Supp. 3 National Biomedical Research Foundation.
Engvall, E., (1980) "Enzyme Immunoassay ELISA and EMIT" *Meth. Enzymol.* 70:419. Academic Press.

Huse W. D. et al. (1989) "Generation of a Large Combinatorial Library of the Immunoglobulin Repertoire in Phage Lambda" Science December; 256:1275-1281.
Inouye & Inouye, (1985) "Up-promoter mutations in the *Ipp* gene of *Escherichia coli*"*Nucleic Acids Res.*, April; 13(9):3101-3109.
Janknecht, et al., (1991) "Rapid and efficient purification of native histidine-tagged protein expressed by recombinant vaccinia virus" *Proc. Natl. A cad. Sci. USA* October; 88: 8972-8976.
Koehler and Milstein, (1975) "Continuous cultures of fused cells secreting antibody of predefined specificity" *Nature* August; 256:495-497.
Kozbor et al., (1983) "The production of monoclonal antibodies from human lymphocytes" *Immunol Today* 4(3):72.
Lowy, et al., (1980) "Isolation of Transforming DNA: Cloning the Hampster aprt Gene" *Cell* December; 22:817.
Morrison et al., "Chimeric human antibody molecules: Mouse antigen-binding domains with human constant region domains" *Proc Natl Acad Sci*, November; 81:6851-6855 (1984).
Mulligan & Berg, (1981) "Selection for animal cells that express the *Escherichia coli* gene coding for xanthine-guanine phosphoribosyltransferase" *Proc Natl Acad Sci, USA* April; 78:2072.
Neuberger et al., (1984) "Recombinant antibodies possessing novel effector functions" *Nature* December; 312:604-608.
O'Hare, et al., "Transformation of mouse fibroblasts to methotrexate resistance by a recombinant plasmid expressing a prokaryotic dihydrofolate reductase" *Proc. Natl. Acad. Sci. USA* March; 78:1527 (1981).
Orlandi et al., "Cloning immunoglobulin variable domains for expression by the polymerase chain reaction" *Proc Natl Acad Sci* May; 86: 3833-3837 (1989).
Ruther et al., (1983) "Easy identification of cDNA clones" *EMBO J.* 2(10):1791.
Santerre, et al., (1984) "Expression of prokaryotic genes for hygromycin B and G418 resistance as dominant-selection markers in mouse L cells" *Gene* 30:147.
Smith et al., (1983) "Molecular Engineering of the Autographa californica Nuclear Polyhedrosis Virus Genome: Deletion Mutations Within the Polyhedrin Gene" *J. Virol.* May; 46:584.
Szybalska & Szybalski, (1962) "Genetics of human cell lines, IV. DNA-mediated heritable transformation of a biochemical trait" *Proc. Natl. Acad. Sci. USA* October; 48:2026.
Takeda et al., (1985) "Construction of chimaeric processed immunoglobulin genes containing mouse variable and human constant region sequences" *Nature* April; 314:452-454.
Vaitukaitis, J. et al., (1971) "A method for producing specific antisera with small doses of immunogen" *J. Clin. Endocrinol. Metab.* 33:988-991.
Van Heeke & Schuster, (1989) "Expression of Human Asparigine Synthetase in *Escherichia coli*" *J. Biol. Chem.*, April; 264:5503-5509.
Wigler, et al., (1977) "Transfer of Purified Herpes Virus Thymidine Kinase Gene to Cultured Mouse Cells" *Cell* May;11:223.
Wigler, et al., (1980) "Transformation of mammalian cells with an amplifiable dominant-acting gene" *Proc. Natl. Acad. Sci. USA* June; 77:3567.
Winter G. And Milstein C; (1991) "Man-made antibodies" *Nature* January; 349:293-299.

\* cited by examiner

| Clone ID | WT | Pos. 1 | Pos. 2 | Pos. 3 | Pos. 4 | Pos. 5 | Pos. 6 | Pos. 7 | Pos. 8 | Pos. 9 |
|---|---|---|---|---|---|---|---|---|---|---|
| 18H4 | 100 | 105 | 50 | 9 | 3 | 3 | 54 | 3 | 45 | 50 |
| 18A4 | 100 | 119 | 22 | 14 | 3 | 4 | 18 | 4 | 5 | 6 |
| 14G7 | 100 | 120 | 112 | 4 | 1 | 2 | 48 | 2 | 43 | 32 |
| 14F8 | 100 | 111 | 87 | 3 | 2 | 2 | 50 | 2 | 45 | 31 |
| 12B11 | 100 | 115 | 59 | 18 | 7 | 8 | 174 | 7 | 168 | 63 |
| 14E9 | 100 | 87 | 126 | 4 | 2 | 2 | 42 | 2 | 40 | 28 |
| 16B3 | 100 | 89 | 124 | 4 | 2 | 2 | 44 | 2 | 42 | 31 |
| 17B7 | 100 | 115 | 71 | 6 | 2 | 2 | 53 | 2 | 50 | 18 |
| 14F9 | 100 | 100 | 95 | 4 | 2 | 2 | 49 | 2 | 81 | 44 |

B

| Clone ID | Pos. 1 | Pos. 2 | Pos. 3 | Pos. 4 | Pos. 5 | Pos. 6 | Pos. 7 | Pos. 8 | Pos. 9 |
|---|---|---|---|---|---|---|---|---|---|
| 18H4 | 0.64 | 2000 | >10000 | >10000 | >10000 | 0.13 | >10000 | 400 | 400 |
| 18A4 | 0.13 | 400 | >10000 | >10000 | >10000 | .80 | >10000 | >10000 | >10000 |
| 14G7 | 0.13 | 80 | >10000 | >10000 | >10000 | 0.13 | >10000 | 3.2 | 2000 |
| 14F8 | 0.18 | 2000 | >10000 | >10000 | >10000 | 0.13 | >10000 | 16 | 2000 |
| 12B11 | 0.64 | 2000 | >10000 | >10000 | >10000 | 0.13 | >10000 | 16 | 2000 |
| 14E9 | 0.13 | 2000 | >10000 | >10000 | >10000 | 0.13 | >10000 | 16 | 2000 |
| 16B3 | 0.13 | 2000 | >10000 | >10000 | >10000 | 0.13 | >10000 | 3.2 | 2000 |
| 17B7 | 0.13 | 2000 | >10000 | >10000 | >10000 | 0.13 | >10000 | 16 | 2000 |
| 14F9 | 0.64 | 2000 | >10000 | >10000 | >10000 | 0.13 | >10000 | 80 | 2000 |

| Chain | CDR3 Sequence | SEQ ID NO |
|---|---|---|
| 19 alpha | C A A S L I T G N T G K L I F G L G T T L Q V Q P<br>TRAV 10          TRAJ 37 | 104 |
| 19 beta | C A S S L T A N T E V F F G K G T R L T V V<br>TRBV 19 TRBD1      TRBJ 1-1 | 105 |

B

| Chain | CDR3 Sequence | SEQ ID NO |
|---|---|---|
| 69 alpha | C A S G D E G Y N S P L Y F A A G T R L T V T<br>TRBV13.2 TRBD1    TRBJ 1-6 | 106 |
| 69 beta | C I V T D L G I T G N T G K L I F G L G T T L Q V Q P<br>TRAV2           TRAJ 37 | 107 |

```
                         SEQUENCE LISTING

<160> NUMBER OF SEQ ID NOS: 119

<210> SEQ ID NO 1
<211> LENGTH: 25
<212> TYPE: PRT
<213> ORGANISM: Artificial Sequence
<220> FEATURE:
<223> OTHER INFORMATION: I8H4 CDR3 region for alpha chain

<400> SEQUENCE: 1

Cys Ala Met Arg Glu Ile Thr Gly Asn Thr Gly Lys Leu Ile Phe Gly
1               5                   10                  15

Leu Gly Thr Thr Leu Gln Val Gln Pro
            20                  25

<210> SEQ ID NO 2
<211> LENGTH: 25
<212> TYPE: PRT
<213> ORGANISM: Artificial Sequence
<220> FEATURE:
<223> OTHER INFORMATION: I8H4 CDR3 region for beta chain

<400> SEQUENCE: 2

Cys Ala Ser Ser Asp Ala Leu Gly Gly Glu Asp Ala Glu Gln Phe Phe
1               5                   10                  15

Gly Pro Gly Thr Arg Leu Thr Val Leu
            20                  25

<210> SEQ ID NO 3
<211> LENGTH: 25
<212> TYPE: PRT
<213> ORGANISM: Artificial Sequence
<220> FEATURE:
<223> OTHER INFORMATION: I8A4 CDR3 region for alpha chain

<400> SEQUENCE: 3

Cys Ile Val Thr Asp Val Glu Thr Gly Gly Tyr Lys Ala Val Phe Gly
1               5                   10                  15

Ser Gly Thr Arg Leu Leu Val Ser Pro
            20                  25

<210> SEQ ID NO 4
<211> LENGTH: 24
<212> TYPE: PRT
<213> ORGANISM: Artificial Sequence
<220> FEATURE:
<223> OTHER INFORMATION: I8A4 CDR3 region for beta chain

<400> SEQUENCE: 4

Cys Ala Ser Ala Ser Thr Gly Ala Ser Ser Tyr Glu Gln Tyr Phe Gly
1               5                   10                  15

Pro Gly Thr Arg Leu Thr Val Leu
            20

<210> SEQ ID NO 5
<211> LENGTH: 24
<212> TYPE: PRT
<213> ORGANISM: Artificial Sequence
<220> FEATURE:
<223> OTHER INFORMATION: I4G7 CDR3 region for alpha chain
```

```
<400> SEQUENCE: 5

Cys Ala Val Ser Arg Asp Thr Asn Thr Gly Lys Leu Thr Phe Gly Asp
  1               5                  10                  15

Gly Thr Val Leu Thr Val Lys Pro
             20

<210> SEQ ID NO 6
<211> LENGTH: 23
<212> TYPE: PRT
<213> ORGANISM: Artificial Sequence
<220> FEATURE:
<223> OTHER INFORMATION: I4G7 CDR3 region for beta chain

<400> SEQUENCE: 6

Cys Ala Ser Ser Gly Gly Leu Gly Gly His Thr Leu Tyr Phe Gly Ala
  1               5                  10                  15

Gly Thr Arg Leu Ser Val Leu
             20

<210> SEQ ID NO 7
<211> LENGTH: 24
<212> TYPE: PRT
<213> ORGANISM: Artificial Sequence
<220> FEATURE:
<223> OTHER INFORMATION: I4G7 CDR3 region for beta chain 2

<400> SEQUENCE: 7

Cys Ala Ser Ser Asp Tyr Arg Asp Ser Gly Asn Thr Leu Tyr Phe Gly
  1               5                  10                  15

Glu Gly Ser Arg Leu Ile Val Val
             20

<210> SEQ ID NO 8
<211> LENGTH: 22
<212> TYPE: PRT
<213> ORGANISM: Artificial Sequence
<220> FEATURE:
<223> OTHER INFORMATION: I4F8 CDR3 region for alpha chain

<400> SEQUENCE: 8

Cys Ala Val Ser Asn Met Gly Tyr Lys Leu Thr Phe Gly Thr Gly Thr
  1               5                  10                  15

Ser Leu Leu Val Asp Pro
             20

<210> SEQ ID NO 9
<211> LENGTH: 24
<212> TYPE: PRT
<213> ORGANISM: Artificial Sequence
<220> FEATURE:
<223> OTHER INFORMATION: I4F8 CDR3 region for beta chain

<400> SEQUENCE: 9

Cys Ala Ser Ser Gln Glu Met Gly Gly Ala Leu Glu Gln Tyr Phe Gly
  1               5                  10                  15

Pro Gly Thr Arg Leu Thr Val Leu
             20

<210> SEQ ID NO 10
<211> LENGTH: 9
<212> TYPE: PRT
<213> ORGANISM: Artificial Sequence
<220> FEATURE:
<223> OTHER INFORMATION: NS3 1073-1081
```

```
<400> SEQUENCE: 10

Cys Ile Asn Gly Val Cys Trp Thr Val
 1               5

<210> SEQ ID NO 11
<211> LENGTH: 9
<212> TYPE: PRT
<213> ORGANISM: Artificial Sequence
<220> FEATURE:
<223> OTHER INFORMATION: NS3 1073-1081 (5-A)

<400> SEQUENCE: 11

Cys Ile Asn Gly Ala Cys Trp Thr Val
 1               5

<210> SEQ ID NO 12
<211> LENGTH: 9
<212> TYPE: PRT
<213> ORGANISM: Artificial Sequence
<220> FEATURE:
<223> OTHER INFORMATION: NS3 1073-1081 (1-A)

<400> SEQUENCE: 12

Ala Ile Asn Gly Val Cys Trp Thr Val
 1               5

<210> SEQ ID NO 13
<211> LENGTH: 9
<212> TYPE: PRT
<213> ORGANISM: Artificial Sequence
<220> FEATURE:
<223> OTHER INFORMATION: NS3 1073-1081 (6-A)

<400> SEQUENCE: 13

Cys Ile Asn Gly Val Ala Trp Thr Val
 1               5

<210> SEQ ID NO 14
<211> LENGTH: 9
<212> TYPE: PRT
<213> ORGANISM: Artificial Sequence
<220> FEATURE:
<223> OTHER INFORMATION: NS3 1073-1081 (2-A)

<400> SEQUENCE: 14

Cys Ala Asn Gly Val Cys Trp Thr Val
 1               5

<210> SEQ ID NO 15
<211> LENGTH: 9
<212> TYPE: PRT
<213> ORGANISM: Artificial Sequence
<220> FEATURE:
<223> OTHER INFORMATION: NS3 1073-1081 (7-A)

<400> SEQUENCE: 15

Cys Ile Asn Gly Val Cys Ala Thr Val
 1               5

<210> SEQ ID NO 16
<211> LENGTH: 9
<212> TYPE: PRT
<213> ORGANISM: Artificial Sequence
<220> FEATURE:
<223> OTHER INFORMATION: NS3 1073-1081 (3-A)
```

```
<400> SEQUENCE: 16

Cys Ile Ala Gly Val Cys Trp Thr Val
 1               5

<210> SEQ ID NO 17
<211> LENGTH: 9
<212> TYPE: PRT
<213> ORGANISM: Artificial Sequence
<220> FEATURE:
<223> OTHER INFORMATION: NS3 1073-1081 (8-A)

<400> SEQUENCE: 17

Cys Ile Asn Gly Val Cys Trp Ala Val
 1               5

<210> SEQ ID NO 18
<211> LENGTH: 9
<212> TYPE: PRT
<213> ORGANISM: Artificial Sequence
<220> FEATURE:
<223> OTHER INFORMATION: NS3 1073-1081 (4-A)

<400> SEQUENCE: 18

Cys Ile Asn Ala Val Cys Trp Thr Val
 1               5

<210> SEQ ID NO 19
<211> LENGTH: 9
<212> TYPE: PRT
<213> ORGANISM: Artificial Sequence
<220> FEATURE:
<223> OTHER INFORMATION: NS3 1073-1081 (9-A)

<400> SEQUENCE: 19

Cys Ile Asn Gly Val Cys Trp Thr Ala
 1               5

<210> SEQ ID NO 20
<211> LENGTH: 9
<212> TYPE: PRT
<213> ORGANISM: Artificial Sequence
<220> FEATURE:
<223> OTHER INFORMATION: NS3 1073-1081

<400> SEQUENCE: 20

Cys Val Asn Gly Val Cys Trp Thr Val
 1               5

<210> SEQ ID NO 21
<211> LENGTH: 10
<212> TYPE: PRT
<213> ORGANISM: Artificial Sequence
<220> FEATURE:
<223> OTHER INFORMATION: NS3 1406-1415

<400> SEQUENCE: 21

Lys Leu Val Ala Leu Gly Val Asn Ala Val
 1               5                   10

<210> SEQ ID NO 22
<211> LENGTH: 9
<212> TYPE: PRT
<213> ORGANISM: Artificial Sequence
<220> FEATURE:
<223> OTHER INFORMATION: NS3 1073-1081 (1-A)

<400> SEQUENCE: 22
```

```
Ala Ile Asn Gly Val Cys Trp Thr Val
 1               5

<210> SEQ ID NO 23
<211> LENGTH: 9
<212> TYPE: PRT
<213> ORGANISM: Artificial Sequence
<220> FEATURE:
<223> OTHER INFORMATION: NS3 1073-1081 (2-A)

<400> SEQUENCE: 23

Cys Ala Asn Gly Val Cys Trp Thr Val
 1               5

<210> SEQ ID NO 24
<211> LENGTH: 9
<212> TYPE: PRT
<213> ORGANISM: Artificial Sequence
<220> FEATURE:
<223> OTHER INFORMATION: NS3 1073-1081 (3-A)

<400> SEQUENCE: 24

Cys Ile Ala Gly Val Cys Trp Thr Val
 1               5

<210> SEQ ID NO 25
<211> LENGTH: 9
<212> TYPE: PRT
<213> ORGANISM: Artificial Sequence
<220> FEATURE:
<223> OTHER INFORMATION: NS3 1073-1081 (4-A)

<400> SEQUENCE: 25

Cys Ile Asn Ala Val Cys Trp Thr Val
 1               5

<210> SEQ ID NO 26
<211> LENGTH: 9
<212> TYPE: PRT
<213> ORGANISM: Artificial Sequence
<220> FEATURE:
<223> OTHER INFORMATION: NS3 1073-1081 (5-A)

<400> SEQUENCE: 26

Cys Ile Asn Gly Ala Cys Trp Thr Val
 1               5

<210> SEQ ID NO 27
<211> LENGTH: 9
<212> TYPE: PRT
<213> ORGANISM: Artificial Sequence
<220> FEATURE:
<223> OTHER INFORMATION: NS3 1073-1081 (6-A)

<400> SEQUENCE: 27

Cys Ile Asn Gly Val Ala Trp Thr Val
 1               5

<210> SEQ ID NO 28
<211> LENGTH: 9
<212> TYPE: PRT
<213> ORGANISM: Artificial Sequence
<220> FEATURE:
<223> OTHER INFORMATION: NS3 1073-1081 (7-A)

<400> SEQUENCE: 28
```

Cys Ile Asn Gly Val Cys Ala Thr Val
1               5

<210> SEQ ID NO 29
<211> LENGTH: 9
<212> TYPE: PRT
<213> ORGANISM: Artificial Sequence
<220> FEATURE:
<223> OTHER INFORMATION: NS3 1073-1081 (8-A)

<400> SEQUENCE: 29

Cys Ile Asn Gly Val Cys Trp Ala Val
1               5

<210> SEQ ID NO 30
<211> LENGTH: 9
<212> TYPE: PRT
<213> ORGANISM: Artificial Sequence
<220> FEATURE:
<223> OTHER INFORMATION: NS3 1073-1081 (9-A)

<400> SEQUENCE: 30

Cys Ile Asn Gly Val Cys Trp Thr Ala
1               5

<210> SEQ ID NO 31
<211> LENGTH: 20
<212> TYPE: DNA
<213> ORGANISM: Artificial Sequence
<220> FEATURE:
<223> OTHER INFORMATION: Ca Inner

<400> SEQUENCE: 31
agagggtgct gtcctgagac                                          20

<210> SEQ ID NO 32
<211> LENGTH: 20
<212> TYPE: DNA
<213> ORGANISM: Artificial Sequence
<220> FEATURE:
<223> OTHER INFORMATION: Va1

<400> SEQUENCE: 32
cagcagagcc cagaatccct                                          20

<210> SEQ ID NO 33
<211> LENGTH: 20
<212> TYPE: DNA
<213> ORGANISM: Artificial Sequence
<220> FEATURE:
<223> OTHER INFORMATION: Va2

<400> SEQUENCE: 33
ttcccatggt actggcagtt                                          20

<210> SEQ ID NO 34
<211> LENGTH: 17
<212> TYPE: DNA
<213> ORGANISM: Artificial Sequence
<220> FEATURE:
<223> OTHER INFORMATION: Va3/4

<400> SEQUENCE: 34
ctkttctggt atgtcca                                             17

<210> SEQ ID NO 35

-continued

<210> SEQ ID NO 35
<211> LENGTH: 22
<212> TYPE: DNA
<213> ORGANISM: Artificial Sequence
<220> FEATURE:
<223> OTHER INFORMATION: Va4

<400> SEQUENCE: 35
ggtacccwrm yctkttctgg ta                                      22

<210> SEQ ID NO 36
<211> LENGTH: 19
<212> TYPE: DNA
<213> ORGANISM: Artificial Sequence
<220> FEATURE:
<223> OTHER INFORMATION: Va5/7

<400> SEQUENCE: 36
ayytyttctg gtacaagca                                          19

<210> SEQ ID NO 37
<211> LENGTH: 20
<212> TYPE: DNA
<213> ORGANISM: Artificial Sequence
<220> FEATURE:
<223> OTHER INFORMATION: Va6/12

<400> SEQUENCE: 37
atctaytggt accgacaggt                                         20

<210> SEQ ID NO 38
<211> LENGTH: 20
<212> TYPE: DNA
<213> ORGANISM: Artificial Sequence
<220> FEATURE:
<223> OTHER INFORMATION: Va8

<400> SEQUENCE: 38
gtgacccaga cagaaggcct                                         20

<210> SEQ ID NO 39
<211> LENGTH: 19
<212> TYPE: DNA
<213> ORGANISM: Artificial Sequence
<220> FEATURE:
<223> OTHER INFORMATION: Va10

<400> SEQUENCE: 39
tgcagtggtt ttaccaaag                                          19

<210> SEQ ID NO 40
<211> LENGTH: 17
<212> TYPE: DNA
<213> ORGANISM: Artificial Sequence
<220> FEATURE:
<223> OTHER INFORMATION: Va11

<400> SEQUENCE: 40
agaattccag gggcagc                                            17

<210> SEQ ID NO 41
<211> LENGTH: 19
<212> TYPE: DNA
<213> ORGANISM: Artificial Sequence
<220> FEATURE:
<223> OTHER INFORMATION: Va15

<400> SEQUENCE: 41

-continued gaaagccaaa cgcttctcc                                             19

<210> SEQ ID NO 42
<211> LENGTH: 21
<212> TYPE: DNA
<213> ORGANISM: Artificial Sequence
<220> FEATURE:
<223> OTHER INFORMATION: Cb Inner

<400> SEQUENCE: 42
gccaagcaca cgagggtagc c                                          21

<210> SEQ ID NO 43
<211> LENGTH: 23
<212> TYPE: DNA
<213> ORGANISM: Artificial Sequence
<220> FEATURE:
<223> OTHER INFORMATION: Vb1

<400> SEQUENCE: 43
atctaatcct gggaagagca aat                                        23

<210> SEQ ID NO 44
<211> LENGTH: 23
<212> TYPE: DNA
<213> ORGANISM: Artificial Sequence
<220> FEATURE:
<223> OTHER INFORMATION: Vb2

<400> SEQUENCE: 44
ggcgtctggt accacgtggt caa                                        23

<210> SEQ ID NO 45
<211> LENGTH: 23
<212> TYPE: DNA
<213> ORGANISM: Artificial Sequence
<220> FEATURE:
<223> OTHER INFORMATION: Vb3

<400> SEQUENCE: 45
gtgaaagggc aaggacaaaa agc                                        23

<210> SEQ ID NO 46
<211> LENGTH: 22
<212> TYPE: DNA
<213> ORGANISM: Artificial Sequence
<220> FEATURE:
<223> OTHER INFORMATION: Vb4

<400> SEQUENCE: 46
gatatgcgaa cagtatctag gc                                         22

<210> SEQ ID NO 47
<211> LENGTH: 22
<212> TYPE: DNA
<213> ORGANISM: Artificial Sequence
<220> FEATURE:
<223> OTHER INFORMATION: Vb5

<400> SEQUENCE: 47
acataacaaa ggaaagggag aa                                         22

<210> SEQ ID NO 48
<211> LENGTH: 23
<212> TYPE: DNA

```
<213> ORGANISM: Artificial Sequence
<220> FEATURE:
<223> OTHER INFORMATION: Vb6

<400> SEQUENCE: 48
tcctgattgg tcaggaaggg caa                                          23

<210> SEQ ID NO 49
<211> LENGTH: 23
<212> TYPE: DNA
<213> ORGANISM: Artificial Sequence
<220> FEATURE:
<223> OTHER INFORMATION: Vb7

<400> SEQUENCE: 49
tacctgatca aaagaatggg aga                                          23

<210> SEQ ID NO 50
<211> LENGTH: 21
<212> TYPE: DNA
<213> ORGANISM: Artificial Sequence
<220> FEATURE:
<223> OTHER INFORMATION: Vb8

<400> SEQUENCE: 50
gtactggtat cggcaggaca c                                            21

<210> SEQ ID NO 51
<211> LENGTH: 23
<212> TYPE: DNA
<213> ORGANISM: Artificial Sequence
<220> FEATURE:
<223> OTHER INFORMATION: Vb9

<400> SEQUENCE: 51
agcttgcaag agttggaaaa cca                                          23

<210> SEQ ID NO 52
<211> LENGTH: 23
<212> TYPE: DNA
<213> ORGANISM: Artificial Sequence
<220> FEATURE:
<223> OTHER INFORMATION: Vb10

<400> SEQUENCE: 52
gattatgttt agctacaata ata                                          23

<210> SEQ ID NO 53
<211> LENGTH: 23
<212> TYPE: DNA
<213> ORGANISM: Artificial Sequence
<220> FEATURE:
<223> OTHER INFORMATION: Vb11

<400> SEQUENCE: 53
acaaggtgac agggaaggga caa                                          23

<210> SEQ ID NO 54
<211> LENGTH: 23
<212> TYPE: DNA
<213> ORGANISM: Artificial Sequence
<220> FEATURE:
<223> OTHER INFORMATION: Vb12

<400> SEQUENCE: 54
acctacagaa cccaaggact cag                                          23
```

<210> SEQ ID NO 55
<211> LENGTH: 23
<212> TYPE: DNA
<213> ORGANISM: Artificial Sequence
<220> FEATURE:
<223> OTHER INFORMATION: Vb13

<400> SEQUENCE: 55
cagttgccct cggatcgatt ttc         23

<210> SEQ ID NO 56
<211> LENGTH: 23
<212> TYPE: DNA
<213> ORGANISM: Artificial Sequence
<220> FEATURE:
<223> OTHER INFORMATION: Vb14

<400> SEQUENCE: 56
gccgagatca aggctgtggg cag         23

<210> SEQ ID NO 57
<211> LENGTH: 23
<212> TYPE: DNA
<213> ORGANISM: Artificial Sequence
<220> FEATURE:
<223> OTHER INFORMATION: Vb15

<400> SEQUENCE: 57
agaaccatct gtaagagtgg aac         23

<210> SEQ ID NO 58
<211> LENGTH: 23
<212> TYPE: DNA
<213> ORGANISM: Artificial Sequence
<220> FEATURE:
<223> OTHER INFORMATION: Vb16

<400> SEQUENCE: 58
catcaaataa tacatatggg gca         23

<210> SEQ ID NO 59
<211> LENGTH: 22
<212> TYPE: DNA
<213> ORGANISM: Artificial Sequence
<220> FEATURE:
<223> OTHER INFORMATION: Vb17

<400> SEQUENCE: 59
gtagtcctga aagggcaca ct         22

<210> SEQ ID NO 60
<211> LENGTH: 22
<212> TYPE: DNA
<213> ORGANISM: Artificial Sequence
<220> FEATURE:
<223> OTHER INFORMATION: Vb18

<400> SEQUENCE: 60
catctgtcaa agtggcactt ca         22

<210> SEQ ID NO 61
<211> LENGTH: 22
<212> TYPE: DNA
<213> ORGANISM: Artificial Sequence
<220> FEATURE:

<223> OTHER INFORMATION: Vb19

<400> SEQUENCE: 61
agacatctgg tcaaaggaaa ag                                           22

<210> SEQ ID NO 62
<211> LENGTH: 10
<212> TYPE: PRT
<213> ORGANISM: Artificial Sequence
<220> FEATURE:
<223> OTHER INFORMATION: NS3 1406-1415

<400> SEQUENCE: 62

Lys Leu Val Ala Leu Gly Ile Asn Ala Val
 1               5                  10

<210> SEQ ID NO 63
<211> LENGTH: 852
<212> TYPE: DNA
<213> ORGANISM: Artificial Sequence
<220> FEATURE:
<223> OTHER INFORMATION: I8H4 alpha chain

<400> SEQUENCE: 63
atgctgattc tgagcctgct gggcgcggcg tttggcagca tttgctttgc ggcgaccagc      60
atggcgcaga aagtgaccca gacccagacc agcattagcg tggtggaaaa aaccaccgtg     120
accatggatt gcgtgtatga aacccgcgat agcagctatt ttcggccgcg aattcgccct     180
tggtacccta ctctgttttg gtataaacag accgcgagcg gcgaaattgt gtttctgatt     240
cgccaggata gctataaaaa agaaaacgcg accgtgggcc attatagcct gaactttcag     300
aaaccgaaaa gcagcattgg cctgattatt accgcgaccc agattgaaga tagcgcggtg     360 tattttgcg cgatgcgcga attaccggc aacaccggca actgattttt tggcctgggc       420
accaccctgc aggtgcagcc ggatattcag aacccggaac cggcggtgta tcagctgaaa     480
gatccgcgca gccaggatag caccctgtgc ctgtttaccg attttgatag ccagattaac     540
gtgccgaaaa ccatggaaag cggcaccttt attaccgata aaaccgtgct ggatatgaaa     600
gcgatggata gcaaaagcaa cggcgcgatt gcgtggagca ccagaccag ctttacctgc       660 caggatattt ttaaagaaac caacgcgacc tatccgagca gcgatgtgcc gtgcgatgcg     720
accctgaccg aaaaaagctt tgaaaccgat atgaacctga ctttcagaa cctgagcgtg      780 atgggcctgc gcattctgct gctgaaagtg gcgggcttta acctgctgat gaccctgcgc     840
ctgtggagca gc                                                         852

<210> SEQ ID NO 64
<211> LENGTH: 960
<212> TYPE: DNA
<213> ORGANISM: Artificial Sequence
<220> FEATURE:
<223> OTHER INFORMATION: I8H4 beta chain

<400> SEQUENCE: 64
atggttagcc aagtgtgct tctctcccct gaattcccaa gtctttctgc tcagatgaca       60
tcatcaggct ttgtctttct ctatcataga acacatggag gctgcagtca cccaaagccc     120
tagaaacaag gtgacagtaa caggaggaaa cgtgacattg agctgtcgcc agactaatag     180
ccacaactac atgtactggt atcggcagga cactgggcat gggctgaggc tgatccatta     240
ctcatatggt gctggcaacc ttcgaatagg agatgtccct gatgggtaca aggccaccag     300

| | | |
|---|---|---|
| aacaacgcaa gaagacttct tcctcctgct ggaattggct tctccctctc agacatcttt | 360 | |
| gtacttctgt gccagcagtg atgcgctggg cggcgaagat gcggaacagt tttttggccc | 420 | |
| gggcacccgc ctgaccgtgc tggaggatct gagaaatgtg actccaccca aggtctcctt | 480 | |
| gtttgagcca tcaaaagcag agattgcaaa caaacaaaag ctaccctcg tgtgcttggc | 540 | |
| caggggcttc ttccctgacc acgtggagct gagctggtgg gtgaatggca aggaggtcca | 600 | |
| cagtggggtc agcacggacc ctcaggccta caaggagagc aattatagct actgcctgag | 660 | |
| cagccgcctg agggtctctg ctaccttctg gcacaatcct cgaaaccact tccgctgcca | 720 | |
| agtgcagttc catgggcttt cagaggagga caagtggcca gagggctcac ccaaacctgt | 780 | |
| cacacagaac atcagtgcag aggcctgggg ccgagcagac tgtgggatta cctcagcatc | 840 | |
| ctatcaacaa gggtcttgt ctgccaccat cctctatgag atcctgctag ggaaagccac | 900 | |
| cctgtatgct gtgcttgtca gtacactggg ggtgatggct atggtcaaaa gaagaattc | 960 | |

<210> SEQ ID NO 65
<211> LENGTH: 798
<212> TYPE: DNA
<213> ORGANISM: Artificial Sequence
<220> FEATURE:
<223> OTHER INFORMATION: I8A4 alpha chain

<400> SEQUENCE: 65

| | | |
|---|---|---|
| atgaagcagg tggcaaaagt gactgtgctc ctgatcttgg tctcatggag ccttgccaag | 60 | |
| accacccagc cccctccat ggaggcctat gaagggcaag aagtgaacgt gtcctgcagc | 120 | |
| catacaaaca ttgctacaag cgagtacatc tactggtacc gacaggttcc ccaccaggga | 180 | |
| ccacagttta tcattcaagg atataaggac tatgtggtaa atgaagtggc atctctgttt | 240 | |
| atctctgctg accggaagct cagcactctg agcctgccct gggtttccct gagagatgct | 300 | |
| gctgtgtatt actgcattgt gactgacgtg gaaactggag ctataaagc ggtctttgga | 360 | |
| agtgggactc gattgctggt aagccctgac atccagaacc cagaacctgc tgtgtaccag | 420 | |
| ttaaaagatc ctcggtctca ggacagcacc ctctgcctgt tcaccgactt tgactcccaa | 480 | |
| atcaatgtgc cgaaaaccat ggaatctgga acgttcatca ctgacaaaac tgtgctggac | 540 | |
| atgaaagcta tggattccaa gagcaatggg gccattgcct ggagcaacca gacaagcttc | 600 | |
| acctgccaag atatcttcaa agagaccaac gccacctacc ccagttcaga cgttccctgt | 660 | |
| gatgccacgt tgactgagaa aagctttgaa acagatatga acctaaactt tcaaaacctg | 720 | |
| tcagttatgg gactccgaat cctcctgctg aaagtagccg gatttaacct gctcatgacg | 780 | |
| ctgaggctgt ggtccagt | 798 | |

<210> SEQ ID NO 66
<211> LENGTH: 1007
<212> TYPE: DNA
<213> ORGANISM: Artificial Sequence
<220> FEATURE:
<223> OTHER INFORMATION: I8A4 beta chain

<400> SEQUENCE: 66

| | | |
|---|---|---|
| atgggctcca ggctcttctt cgtgctctcc agtctcctgt gttcaatgag tgctggtcag | 60 | |
| gccacaggtg tgcttctctc tccagaattc ccaagtcttt ttgctaagat gacatcatca | 120 | |
| ggttttgtct ttctttatag acacatggag gctgcagtca cccaaagccc aagaaacaag | 180 | |
| gtggcagtaa caggagaaa ggtgacattg agctgtaatc agactaataa ccacaacaac | 240 | |
| atgtactggt atcggcagga cacggggcat gggctgaggc tgatccatta ttcatatggt | 300 | |

```
gctggcagca ctgagaaagg agatatccct gatggataca aggcctccag accaagccaa      360
gagaacttct ccctcattct ggagttggct accccctctc agacatcagt gtacttctgt      420
gccagcgcct cgactggggc gagctcctat gaacagtact tcggtcccgg caccaggctc      480
acggttttag aggatctgag aaatgtgact ccacccaagg tctccttgtt tgagccatca      540
aaagcagaga ttgcaaacaa acaaaaggct accctcgtgt gcttggccag gggcttcttc      600
cctgaccacg tggagctgag ctggtgggtg aatggcaagg aggtccacag tggggtcagc      660
acggaccctc aggcctacaa ggagagcaat tatagctact gcctgagcag ccgcctgagg      720
gtctctgcta ccttctggca caatcctcga aaccacttcc gctgccaagt gcagttccat      780
gggctttcag aggaggacaa gtggccagag ggctcaccca aacctgtcac acagaacatc      840
agtgcagagg cctggggccg agcagactgt gggattacct cagcatccta tcaacaaggg      900
gtcttgtctg ccaccatcct ctatgagatc ctgctaggga agccacccct gtatgctgtg      960
cttgtcagta cactggtggt gatggctatg gtcaaaagaa agaattc                  1007
```

<210> SEQ ID NO 67  
<211> LENGTH: 843  
<212> TYPE: DNA  
<213> ORGANISM: Artificial Sequence  
<220> FEATURE:  
<223> OTHER INFORMATION: I4G7 alpha chain

<400> SEQUENCE: 67

```
atgctgctgg cgctgctgcc ggtgctgggc attcattttc tgctgcgcga tgcgcaggcg       60
cagagcgtga cccagccgga tgcgcgcgtg accgtgagcg aaggcgcgag cctgcagctg      120
cgctgcaaat atagctattt tggcaccccg tatcgcattg aatttagcgg ccgcgaattt      180
gcgctgctgt tttggtatgt gcagtatccg cgccagggcc tgcagctgct gctgaaatat      240
tatccgggcg atccggtggt gcagggcgtg aacggctttg aagcggaatt tagcaaaagc      300
aacagcagct ttcatctgcg caaagcgagc gtgcattgga gcgattgggc ggtgtatttt      360
tgcgcggtga gccgcgatac caacaccggc aaactgacct ttggcgatgg caccgtgctg      420 accgtgaaaac cgaacattca gaacccggaa ccggcggtgt atcagctgaa agatccgcgc      480
agccaggata gcaccctgtg cctgtttacc gattttgata gccagattaa cgtgccgaaa      540
accatggaaa gcggcacctt tattaccgat aaaaccgtgc tggatatgaa agcgatggat      600
agcaaaagca acggcgcgat tgcgtggagc aaccagacca gctttacctg ccaggatatt      660
tttaaagaaa ccaacgcgac ctatccgagc agcgatgtgc gtgcgatgc gaccctgacc      720 gaaaaaagct ttgaaaccga tatgaacctg aactttcaga acctgagcgt gatgggcctg      780
cgcattctgc tgctgaaagt ggcgggcttt aacctgctga tgaccctgcg cctgtggagc      840
agc                                                                    843
```

<210> SEQ ID NO 68  
<211> LENGTH: 944  
<212> TYPE: DNA  
<213> ORGANISM: Artificial Sequence  
<220> FEATURE:  
<223> OTHER INFORMATION: I4G7 beta chain

<400> SEQUENCE: 68

```
atgggctcca gactcttctt tgtggttttg attctcctgt gtgcacatat ggaagcggcg       60
gtgacccaga gcccgcgcaa caaagtggcg gtgaccggcg gcaaagtgac cctgagctgc      120
```

```
aaccagacca caaccataa caacatgggc gaactgaacc tggcggcggc gaacagcccg    180
ctgtattggt atcgccagga taccggccat ggcctgcgcc tgattcatta tagctatgtg    240
gcggatagca ccgaaaaagg cgatattccg gatggctata aagcgagccg cccgagccag    300
gaaaacttta gcctgattct ggaactggcg agcctgagcc agaccgcggt gtattttgc     360 gcgagcagcg gcggcctggg cggccatacc ctgtattttg gcgcgggcac ccgcctgagc    420
gtgctggagg atctgagaaa tgtgactcca cccaaggtct ccttgtttga gccatcaaaa    480
gcagagattg caaacaaaca aaaggctacc ctcgtgtgct tggccagggg cttcttccct    540
gaccacgtgg agctgagctg tgggtgaat ggcaaggagg tccacagtgg ggtcagcacg      600
gaccctcagg cctacaagga gcaattat agctactgcc tgagcagccg cctgagggtc       660
tctgctacct tctggcacaa tcctcgaaac acttccgct gccaagtgca gttccatggg      720
ctttcagagg aggacaagtg gccagagggc tcacccaaac ctgtcacaca gaacatcagt    780
gcagaggcct ggggccgagc agactgtggg attacctcag catcctatca acaaggggtc    840
ttgtctgcca ccatcctcta tgagatcctg ctagggaaag ccaccctgta tgctgtgctt    900
gtcagtacac tggtggtgat ggctatggtc aaaagaaaga attc                    944

<210> SEQ ID NO 69
<211> LENGTH: 957
<212> TYPE: DNA
<213> ORGANISM: Artificial Sequence
<220> FEATURE:
<223> OTHER INFORMATION: I4G7 beta chain 2

<400> SEQUENCE: 69
atggttagcc caagtgtgct tctctccct gaattcccaa gtctttctgc tcagatgaca      60
tcatcaggct ttgtctttct ctatcataga acacatggag gctgcagtca cccaaagccc    120
tagaaacaag gtgacagtaa caggaggaaa cgtgacattg agctgtcgcc agactaatag    180
ccacaactac atgtactggt atcggcagga cactgggcat gggctgaggc tgatccatta    240
ctcatatggt gctggcaacc ttcgaatagg agatgtccct gatgggtaca aggccaccag    300
aacaacgcaa gaagacttct tcctcctgct ggaattggct tctccctctc agacatcttt    360
gtacttctgc gcgagcagcg attatcgcga tagcggcaac accctgtatt ttggcgaagg    420
cagccgcctg attgtggtgg aagatctgcg caacgtgact ccacccaagg tctccttgtt    480
tgagccatca aaagcagaga ttgcaaacaa acaaaaggct accctcgtgt gcttggccag    540
gggcttcttc cctgaccacg tggagctgag ctggtgggtg aatggcaagg aggtccacag    600
tggggtcagc acggaccctc aggcctacaa ggagagcaat tatagctact gcctgagcag    660
ccgcctgagg gtctctgcta ccttctggca caatcctcga aaccacttcc gctgccaagt    720
gcagttccat gggctttcag aggaggacaa gtggccagag ggctcaccca aacctgtcac    780
acagaacatc agtgcagagg cctgggggcg agcagactgt gggattaccct cagcatccta    840 tcaacaaggg gtcttgtctg ccaccatcct ctatgagatc ctgctaggga aagccaccct    900
gtatgctgtg cttgtcagta cactggtggt gatggctatg gtcaaaagaa agaattc      957

<210> SEQ ID NO 70
<211> LENGTH: 840
<212> TYPE: DNA
<213> ORGANISM: Artificial Sequence
<220> FEATURE:
<223> OTHER INFORMATION: I4F8 alpha chain

<400> SEQUENCE: 70
```

```
atgctgctgg cgctgctgcc ggtgctgggc attcattttc tgctgcgcga tgcgcaggcg    60
cagagcgtga cccagccgga tgcgcgcgtg accgtgagcg aaggcgcgag cctgcagctg   120
cgctgcaaat atagctattt tggcaccccg tatggccgca ttgaatttag cggccgcgaa   180
tttgcgctgc tgttttggta tgtgcagtat ccgcgccagg gcctgcagct gctgctgaaa   240
tattatccgg gcgatccggt ggtgcagggc gtgaacggct ttgaagcgga atttagcaaa   300
agcaacagca gctttcatct gcgcaaagcg agcgtgcatt ggagcgattg ggcggtgtat   360
ttttgcgcgg tgagcaacat gggctataaa ctgacctttg gcaccggcac cagcctgctg   420
gtggatccga acattcagaa cccggaaccg gcggtgtatc agctgaaaga tccgcgcagc   480
caggatagca ccctgtgcct gtttaccgat tttgatagcc agattaacgt gccgaaaacc   540
atggaaagcg gcacctttat taccgataaa accgtgctgg atatgaaagc gatggatagc   600
aaaagcaacg gcgcgattgc gtggagcaac cagaccagct ttacctgcca ggatattttt   660
aaagaaacca acgcgaccta tccgagcagc gatgtgccgt gcgatgcgac cctgaccgaa   720
aaaagctttg aaaccgatat gaacctgaac tttcagaacc tgagcgtgat gggcctgcgc   780
attctgctgc tgaaagtggc gggctttaac ctgctgatga ccctgcgcct gtggagcagc   840
```

<210> SEQ ID NO 71
<211> LENGTH: 929
<212> TYPE: DNA
<213> ORGANISM: Artificial Sequence
<220> FEATURE:
<223> OTHER INFORMATION: I4F8 beta chain

<400> SEQUENCE: 71

```
atgggcagca ttttctctgag ctgcctggcg gtgtgcctgc tggtggcggg cccggtggat    60
ccgaaaatta ttcagaaacc gaaatatctg gtggcggtga ccggcagcga aaaaattacc   120
aacagcccgc tgatttgcga acagtatctg ggccataacg cgatgtattg gtatcgccag   180
agcgcgaaaa aaccgctgga atttatgttt agctatagct atcagaaact gatggataac   240
cagaccgcga gcagccgctt tcagccgcag agcagcaaaa aaaaccatct ggatctgcag   300
attaccgcgc tgaaaccgga tgatagcgcg acctattttt gcgcgagcag ccaggaaatg   360
ggcggcgcgc tgaacagta ttttggcccg ggcacccgcc tgaccgtgct ggaagatctg   420
cgcaacgtga ctccacccaa ggtctccttg tttgagccat caaaagcaga gattgcaaac   480
aaacaaaagg ctaccctcgt gtgcttggcc aggggcttct cccctgacca cgtggagctg   540
agctggtggg tgaatggcaa ggaggtccac agtggggtca gcacggaccc tcaggcctac   600
aaggagagca attatagcta ctgcctgagc agccgcctga gggtctctgc taccttctgg   660
cacaatcctc gaaaccactt ccgctgccaa gtgcagttcc atgggctttc agaggaggac   720
aagtggccag agggctcacc caaacctgtc acacagaaca tcagtgcaga ggcctggggc   780
cgagcagact gtgggattac ctcagcatcc tatcaacaag ggcttgtc tgccaccatc   840 ctctatgaga tcctgctagg gaaagccacc ctgtatgctg tgcttgtcag tacactggtg   900
gtgatggcta tggtcaaaag aaagaattc                                      929
```

<210> SEQ ID NO 72
<211> LENGTH: 274
<212> TYPE: PRT
<213> ORGANISM: Artificial Sequence
<220> FEATURE:
<223> OTHER INFORMATION: I8H4 Alpha Chain -continued

<400> SEQUENCE: 72

```
Met Leu Ile Leu Ser Leu Leu Gly Ala Ala Phe Gly Ser Ile Cys Phe
 1               5                  10                  15

Ala Ala Thr Ser Met Ala Gln Lys Val Thr Gln Thr Gln Thr Ser Ile
             20                  25                  30

Ser Val Val Glu Lys Thr Thr Val Thr Met Asp Cys Val Tyr Glu Thr
         35                  40                  45

Arg Asp Ser Ser Tyr Phe Leu Phe Trp Tyr Lys Gln Thr Ala Ser Gly
     50                  55                  60

Glu Ile Val Phe Leu Ile Arg Gln Asp Ser Tyr Lys Lys Glu Asn Ala
 65                  70                  75                  80

Thr Val Gly His Tyr Ser Leu Asn Phe Gln Lys Pro Lys Ser Ser Ile
                 85                  90                  95

Gly Leu Ile Ile Thr Ala Thr Gln Ile Glu Asp Ser Ala Val Tyr Phe
            100                 105                 110

Cys Ala Met Arg Glu Ile Thr Gly Asn Thr Gly Lys Leu Ile Phe Gly
        115                 120                 125

Leu Gly Thr Thr Leu Gln Val Gln Pro Asp Ile Gln Asn Pro Glu Pro
130                 135                 140

Ala Val Tyr Gln Leu Lys Asp Pro Arg Ser Gln Asp Ser Thr Leu Cys
145                 150                 155                 160

Leu Phe Thr Asp Phe Asp Ser Gln Ile Asn Val Pro Lys Thr Met Glu
                165                 170                 175

Ser Gly Thr Phe Ile Thr Asp Lys Thr Val Leu Asp Met Lys Ala Met
            180                 185                 190

Asp Ser Lys Ser Asn Gly Ala Ile Ala Trp Ser Asn Gln Thr Ser Phe
        195                 200                 205

Thr Cys Gln Asp Ile Phe Lys Glu Thr Asn Ala Thr Tyr Pro Ser Ser
    210                 215                 220

Asp Val Pro Cys Asp Ala Thr Leu Thr Glu Lys Ser Phe Glu Thr Asp
225                 230                 235                 240

Met Asn Leu Asn Phe Gln Asn Leu Ser Val Met Gly Leu Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 73
<211> LENGTH: 306
<212> TYPE: PRT
<213> ORGANISM: Artificial Sequence
<220> FEATURE:
<223> OTHER INFORMATION: I8H4 beta chain

<400> SEQUENCE: 73

```
Met Gly Ser Arg Leu Phe Phe Val Val Leu Ile Leu Leu Cys Ala Lys
 1               5                  10                  15

His Met Glu Ala Ala Val Thr Gln Ser Pro Arg Asn Lys Val Thr Val
             20                  25                  30

Thr Gly Gly Asn Val Thr Leu Ser Cys Arg Gln Thr Asn Ser His Asn
         35                  40                  45

Tyr Met Tyr Trp Tyr Arg Gln Asp Thr Gly His Gly Leu Arg Leu Ile
     50                  55                  60

His Tyr Ser Tyr Gly Ala Gly Asn Leu Arg Ile Gly Asp Val Pro Asp
 65                  70                  75                  80
```

Gly Tyr Lys Ala Thr Arg Thr Thr Gln Glu Asp Phe Phe Leu Leu Leu
                85                  90                  95

Glu Leu Ala Ser Pro Ser Gln Thr Ser Leu Tyr Phe Cys Ala Ser Ser
            100                 105                 110

Asp Ala Leu Gly Gly Glu Asp Ala Glu Gln Phe Phe Gly Pro Gly Thr
            115                 120                 125

Arg Leu Thr Val Leu Glu Asp Leu Arg Asn Val Thr Pro Pro Lys Val
        130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305

<210> SEQ ID NO 74
<211> LENGTH: 825
<212> TYPE: DNA
<213> ORGANISM: Artificial Sequence
<220> FEATURE:
<223> OTHER INFORMATION: I8H4 alpha chain

<400> SEQUENCE: 74
atgctgattc tgagcctgct ggagcagcc tttggctcca tttgttttgc agcaaccagc      60
atggcccaga aggtaacaca gactcagact tcaatttctg tggtggagaa gacaacggtg     120
acaatggact gtgtgtatga aacccgggac agttcttact tcttattctg gtacaagcaa    180
acagcaagtg gggaaatagt tttccttatt cgtcaggact cttacaaaaa ggaaaatgca    240
acagtgggtc attattctct gaactttcag aagccaaaaa gttccatcgg actcatcatc    300
accgccacac agattgagga ctcagcagta tatttctgtg ctatgagaga gataacaggc    360
aataccggaa aactcatctt tggactgggg acaactttac aagtgcaacc agacatccag    420
aacccagaac tgctgtgta ccagttaaaa gatcctcggt ctcaggacag caccctctgc    480
ctgttcaccg actttgactc ccaaatcaat gtgccgaaaa ccatggaatc tggaacgttc    540
atcactgaca aaactgtgct ggacatgaaa gctatggatt ccaagagcaa tggggccatt    600
gcctggagca accagacaag cttcacctgc caagatatct tcaaagagac caacgccacc    660
taccccagtt cagacgttcc ctgtgatgcc acgttgactg agaaaagctt tgaaacagat    720

```
atgaacctaa actttcaaaa cctgtcagtt atgggactcc gaatcctcct gctgaaagta    780
gccggattta acctgctcat gacgctgagg ctgtggtcca gctga                    825
```

<210> SEQ ID NO 75
<211> LENGTH: 921
<212> TYPE: DNA
<213> ORGANISM: Artificial Sequence
<220> FEATURE:
<223> OTHER INFORMATION: I8H4 beta chain

<400> SEQUENCE: 75

```
atgggctcca gactcttctt tgtggttttg attctcctgt gtgcaaaaca catggaggct     60
gcagtcaccc aaagccctag aaacaaggtg acagtaacag aggaaacgt gacattgagc    120 tgtcgccaga ctaatagcca caactacatg tactggtatc ggcaggacac tgggcatggg    180
ctgaggctga tccattactc atatggtgct ggcaaccttc aataggaga tgtccctgat    240 gggtacaagg ccaccagaac aacgcaagaa gacttcttcc tcctgctgga attggcttct    300
ccctctcaga catctttgta cttctgtgcc agcagtgatg cgctgggcgg cgaagatgcg    360
gaacagtttt ttggcccggg cacccgcctg accgtgctgg aggatctgag aaatgtgact    420
ccacccaagg tctccttgtt tgagccatca aaagcagaga ttgcaaacaa caaaaggct     480 accctcgtgt gcttggccag ggcttcttc cctgaccacg tggagctgag ctggtgggtg    540
aatggcaagg aggtccacag tggggtcagc acggaccctc aggcctacaa ggagagcaat    600
tatagctact gcctgagcag ccgcctgagg gtctctgcta ccttctggca caatcctcga    660
aaccacttcc gctgccaagt gcagttccat gggctttcag aggaggacaa gtggccagag    720
ggctcaccca aacctgtcac acagaacatc agtgcagagg cctggggccg agcagactgt    780
ggaatcactt cagcatccta tcatcagggg gttctgtctg caaccatcct ctatgagatc    840
ctactgggga aggccaccct gtatgctgtg cttgtcagta cactggtggt gatggctatg    900
gtcaaaagaa agaattcatg a                                              921
```

<210> SEQ ID NO 76
<211> LENGTH: 825
<212> TYPE: DNA
<213> ORGANISM: Artificial Sequence
<220> FEATURE:
<223> OTHER INFORMATION: I8H4 co-1 alpha chain

<400> SEQUENCE: 76

```
atgctgattc tgagcctgct gggagccgcc tttggctcca tttgttttgc cgccaccagc     60
atggcccaga aggtgacaca gactcagact tccattagcg tggtggagaa gacaaccgtg    120
acaatggact gtgtgtatga aacccgggac agcagctact cctgttctg gtacaagcag    180 acagccagcg gggaaatcgt ttcctcatt cggcaggaca gctacaaaaa ggaaaatgcc    240
acagtgggcc attatagcct gaactttcag aagcccaaaa gctccatcgg actcatcatc    300
accgccacac agattgagga ctccgccgtg tatttctgtg ccatgagaga gatcacaggc    360
aataccggaa aactcatctt tggactgggg acaactctgc aggtgcagcc agacatccag    420
aacccagaac ctgctgtgta ccagctgaaa gatcctcgga gccaggacag caccctctgc    480
ctgttcaccg actttgactc ccagatcaat gtgcccaaaa ccatggaaag cggaaccttc    540
atcactgaca aaaactgtgct ggacatgaaa gctatggatt ccaagagcaa tggggccatt    600
gcctggagca accagacaag cttcacctgc caggatatct tcaaagagac caacgccacc    660
```

```
taccccagct ccgacgtgcc ctgtgatgcc accctgactg agaaaagctt tgaaacagat    720
atgaacctga actttcagaa cctgtccgtg atgggactcc ggatcctcct gctgaaagtg    780
gccggattta acctgctcat gaccctgagg ctgtggtcca gctga                    825
```

```
<210> SEQ ID NO 77
<211> LENGTH: 921
<212> TYPE: DNA
<213> ORGANISM: Artificial Sequence
<220> FEATURE:
<223> OTHER INFORMATION: I8H4 co-1 beta chain

<400> SEQUENCE: 77
atgggctcca gactgttctt tgtggtgctg attctgctgt gtgccaaaca catggaggct     60
gccgtcaccc agagccctag aaacaaggtg acagtgacag aggaaacgt gacactgagc    120 tgtaggcaga ctaatagcca caactacatg tactggtatc ggcaggacac tgggcatggg   180
ctgaggctga tccattactc ctatggagct ggcaacctgc ggatcggaga tgtccctgat   240
gggtacaagg ccaccagaac aacccaagaa gacttcttcc tgctgctgga actggctagc   300
cccagccaga caagcctgta cttctgtgcc agcagcgatg ccctgggcgg cgaagatgcc   360
gaacagtttt ttggccccgg caccaggctg accgtgctgg aggatctgag aaatgtgact   420
ccacccaagg tctccctgtt tgagccatcc aaagccgaga ttgccaacaa caaaaggct    480 accctggtgt gcctggccag ggcttcttc cctgaccacg tggagctgag ctggtgggtg    540
aatggcaagg aggtccacag cggggtcagc actgacctc aggcctacaa ggagagcaat   600
tatagctact gcctgagcag caggctgagg gtctccgcta ccttctggca caatcctcgg   660
aaccacttca ggtgccaggt gcagttccat gggctgtccg aggaggacaa gtggccagag   720
ggctccccta aacctgtcac acagaacatc agcgccgagg cctggggaag agccgactgt   780
ggaatcactt ccgcctccta tcatcagggg gtgctgagcg ccaccatcct gtatgagatc   840
ctgctgggga aggccaccct gtatgctgtg ctggtcagca cactggtggt gatggctatg   900
gtcaaaagaa agaattcctg a                                             921
```

```
<210> SEQ ID NO 78
<211> LENGTH: 825
<212> TYPE: DNA
<213> ORGANISM: Artificial Sequence
<220> FEATURE:
<223> OTHER INFORMATION: I8H4 co-2 alpha chain

<400> SEQUENCE: 78
atgctcatcc tgtcactgct gggcgctgct tttggctcaa tttgcttcgc tgctactagt    60
atggctcaga agtcacaca gacacagacc tccatttccg tggtcgaaaa aacaaccgtc   120
accatggatt gtgtgtacga gactagggac tcctcttact tcctcttttg gtacaaacag   180
accgcctctg gcgaaatcgt gttcctcatt aggcaggact catacaaaaa ggagaacgcc   240
actgtcggac attactccct gaacttccag aaacccaaat cctctatcgg cctcatcatt   300
accgctactc agatcgagga ctccgctgtc tactttgtg ccatgaggga gattactggc   360
aataccggga aactcatctt tggactgggc actacactcc aggtccagcc cgatattcag   420
aatcccgaac tgctgtctca ccagctgaag gatcctagga gccaggatag taccctgtgc   480
ctcttcaccg acttcgattc ccagatcaac gtccccaaaa caatggaatc tggcaccttc   540
attaccgaca aaaccgtgct ggatatgaaa gcaatggact ccaaatccaa tggcgctatc   600
gcttggtcaa accagacatc attcacatgt caggacatct taaggaaac caacgccacc   660
```

```
tacccatctt ccgatgtgcc ctgtgatgct actctcaccg aaaaatcatt cgaaaccgac    720
atgaacctca actttcagaa cctgtccgtg atgggactga aattctgct gctcaaagtg    780 gccggattca atctgctcat gaccctgaga ctgtggtcct cttga                   825
```

<210> SEQ ID NO 79
<211> LENGTH: 921
<212> TYPE: DNA
<213> ORGANISM: Artificial Sequence
<220> FEATURE:
<223> OTHER INFORMATION: I8H4 co-2 beta chain

<400> SEQUENCE: 79

```
atggggagta ggctgttctt tgtcgtgctc atcctgctgt gtgccaaaca catggaggcc    60
gccgtgaccc agagtcctag gaacaaagtc actgtcactg gaggaaatgt gaccctgtcc   120
tgtagacaga ccaatagcca caattacatg tactggtacc ggcaggatac cggacatgga   180
ctgagactca tccactactc ttacggcgct ggcaatctcc gaattggcga cgtccccgac   240
ggctacaaag caactcggac aacacaggag gacttctttc tgctgctgga actcgcttca   300
ccatcccaga cctcactcta cttttgtgct tcatccgatg ctctcggcgg agaggatgcc   360
gagcagtttt ttggacctgg aactcgactc actgtgctgg aggatctgag aaatgtcact   420
ccacccaaag tgtccctctt cgaaccctct aaagccgaaa tcgccaacaa acagaaggct   480
accctcgtct gtctggctag aggattcttc ccgatcacg tggaactgtc ctggtgggtg   540
aacggcaagg aagtccatag cggagtctct accgatcctc aggcttacaa ggagtcaaat   600
tactcttact gcctgtcatc acgactgaga gtgtctgcca cctttggca taaccctaga   660 aaccacttca gatgccaggt ccagtttcat ggactcagcg aggaggacaa atggcccgag   720
ggatctccta aacctgtgac tcagaacatc tctgctgagg cttggggcg agccgactgt   780 ggaatcacta gtgcctctta ccatcagggc gtgctgtctg ctactattct gtacgagatt   840
ctcctgggaa aagccacact gtacgctgtg ctggtgtcca ccctggtcgt catggccatg   900
gtcaaacgga aaaattcctg a                                             921
```

<210> SEQ ID NO 80
<211> LENGTH: 266
<212> TYPE: PRT
<213> ORGANISM: Artificial Sequence
<220> FEATURE:
<223> OTHER INFORMATION: I8A4 alpha chain

<400> SEQUENCE: 80

```
Met Lys Gln Val Ala Lys Val Thr Val Leu Leu Ile Leu Val Ser Trp
  1               5                  10                  15

Ser Leu Ala Lys Thr Thr Gln Pro Pro Ser Met Glu Ala Tyr Glu Gly
                 20                  25                  30

Gln Glu Val Asn Val Ser Cys Ser His Thr Asn Ile Ala Thr Ser Glu
             35                  40                  45

Tyr Ile Tyr Trp Tyr Arg Gln Val Pro His Gln Gly Pro Gln Phe Ile
         50                  55                  60

Ile Gln Gly Tyr Lys Asp Tyr Val Val Asn Glu Val Ala Ser Leu Phe
 65                  70                  75                  80

Ile Ser Ala Asp Arg Lys Leu Ser Thr Leu Ser Leu Pro Trp Val Ser
                 85                  90                  95

Leu Arg Asp Ala Ala Val Tyr Tyr Cys Ile Val Thr Asp Met Glu Thr
                100                 105                 110
```

```
Gly Gly Tyr Lys Val Val Phe Gly Ser Gly Thr Arg Leu Leu Val Ser
            115                 120                 125

Pro Asp Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Thr Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
            195                 200                 205

Thr Asn Ala Thr Tyr Pro Ser Ser Asp Val Pro Cys Asp Ala Thr Leu
            210                 215                 220

Thr Glu Lys Ser Phe Glu Thr Asp Met Asn Leu Asn Phe Gln Asn Leu
225                 230                 235                 240

Ser Val Met Gly Leu Arg Ile Leu Leu Leu Lys Val Ala Gly Phe Asn
                245                 250                 255

Leu Leu Met Thr Leu Arg Leu Trp Ser Ser
            260                 265

<210> SEQ ID NO 81
<211> LENGTH: 305
<212> TYPE: PRT
<213> ORGANISM: Artificial Sequence
<220> FEATURE:
<223> OTHER INFORMATION: I8A4 beta chain

<400> SEQUENCE: 81

Met Gly Ser Arg Leu Phe Phe Val Leu Ser Ser Leu Leu Cys Ser Lys
  1               5                  10                  15

His Met Glu Ala Ala Val Thr Gln Ser Pro Arg Asn Lys Val Ala Val
             20                  25                  30

Thr Gly Gly Lys Val Thr Leu Ser Cys Asn Gln Thr Asn Asn His Asn
             35                  40                  45

Asn Met Tyr Trp Tyr Arg Gln Asp Thr Gly His Gly Leu Arg Leu Ile
 50                  55                  60

His Tyr Ser Tyr Gly Ala Gly Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                 85                  90                  95

Glu Leu Ala Thr Pro Ser Gln Thr Ser Val Tyr Phe Cys Ala Ser Ala
            100                 105                 110

Ser Thr Gly Ala Ser Ser Tyr Glu Gln Tyr Phe Gly Pro Gly Thr Arg
            115                 120                 125

Leu Thr Val Leu Glu Asp Leu Arg Asn Val Thr Pro Pro Lys Val Ser
            130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
            195                 200                 205
```

```
Arg Val Ser Ala Thr Phe Trp His Asn Pro Arg Asn His Phe Arg Cys
    210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
                245                 250                 255
Ala Asp Cys Gly Ile Thr Ser Ala Ser Tyr Gln Gln Gly Val Leu Ser
                260                 265                 270
Ala Thr Ile Leu Tyr Glu Ile Leu Leu Gly Lys Ala Thr Leu Tyr Ala
            275                 280                 285
Val Leu Val Ser Thr Leu Val Val Met Ala Met Val Lys Arg Lys Asn
    290                 295                 300
Ser
305

<210> SEQ ID NO 82
<211> LENGTH: 797
<212> TYPE: DNA
<213> ORGANISM: Artificial Sequence
<220> FEATURE:
<223> OTHER INFORMATION: I8A4 alpha chain

<400> SEQUENCE: 82
atgaagcagg tggcaaaagt gactgtgctc ctgatcttgg tctcatggag ccttgccaag      60
accacccagc cccctccat ggaggcctat gaagggcaag aagtgaacgt gtcctgcagc     120
catacaaaca ttgctacaag cgagtacatc tactggtacc gacaggttcc ccaccaggga    180
ccacagttta tcattcaagg atataaggac tatgtggtaa atgaagtggc atctctgttt    240
atctctgctg accggaagct cagcactctg agcctgccct gggtttccct gagagatgct    300
gctgtgtatt actgcattgt gactgacatg gaaactggag ctataaagt ggtctttgga    360 agtgggactc gattgctggt aagccctgac atccagaacc cagaacctgc tgtgtaccag    420
ttaaaagatc tcggtctca ggacagcacc ctctgcctgt tcaccgactt tgactcccaa     480
atcaatgtgc cgaaaaccat ggaatctgga acgttcatca ctgacaaaac tgtgctggac    540
atgaaagcta tggattccaa gagcaatggg gccattgcct ggagcaacca gacaagcttc    600
acctgccaag atatcttcaa agagaccaac gccacctacc ccagttcaga cgttccctgt    660
gatgccacgt tgactgagaa aagctttgaa acagatatga acctaaactt tcaaaacctg    720
tcagttatgg gactccgaat cctcctgctg aaagtagccg gatttaacct gctcatgacg    780
ctgaggctgt ggtccag                                                   797

<210> SEQ ID NO 83
<211> LENGTH: 918
<212> TYPE: DNA
<213> ORGANISM: Artificial Sequence
<220> FEATURE:
<223> OTHER INFORMATION: I8A4 beta chain

<400> SEQUENCE: 83
atgggctcca ggctcttctt cgtgctctcc agtctcctgt gttcaaaaca catggaggct      60
gcagtcaccc aaagcccaag aaacaaggtg gcagtaacag aggaaaggt gacattgagc    120 tgtaatcaga ctaataacca caacaacatg tactggtatc ggcaggacac ggggcatggg    180
ctgaggctga tccattattc atatggtgct ggcagcactg agaaaggaga tatccctgat    240
ggatacaagg cctccagacc aagccaagag aacttctccc tcattctgga gttggctacc    300
```

```
cccctctcaga catcagtgta cttctgtgcc agcgcctcga ctggggcgag ctcctatgaa    360
cagtacttcg gtcccggcac caggctcacg gttttagagg atctgagaaa tgtgactcca    420
cccaaggtct ccttgtttga gccatcaaaa gcagagattg caaacaaaca aaaggctacc    480
ctcgtgtgct tggccagggg cttcttccct gaccacgtgg agctgagctg gtgggtgaat    540
ggcaaggagg tccacagtgg ggtcagcacg gaccctcagg cctacaagga gagcaattat    600
agctactgcc tgagcagccg cctgagggtc tctgctacct tctggcacaa tcctcgaaac    660
cacttccgct gccaagtgca gttccatggg ctttcagagg aggacaagtg gccagagggc    720
tcacccaaac ctgtcacaca gaacatcagt gcagaggcct ggggccgagc agactgtggg    780
attacctcag catcctatca acaaggggtc ttgtctgcca ccatcctcta tgagatcctg    840
ctagggaaag ccaccctgta tgctgtgctt gtcagtacac tggtggtgat ggctatggtc    900
aaaagaaaga attcatga                                                  918

<210> SEQ ID NO 84
<211> LENGTH: 801
<212> TYPE: DNA
<213> ORGANISM: Artificial Sequence
<220> FEATURE:
<223> OTHER INFORMATION: I8A4 co-1 alpha chain

<400> SEQUENCE: 84
atgaagcagg tggcaaaagt gactgtgctc ctgatcttgg tctcatggag ccttgccaag     60
accacccagc cccctccat ggaggcctat gaagggcaag aagtgaacgt gtcctgcagc    120
catacaaaca ttgctacaag cgagtacatc tactggtacc gacaggttcc ccaccaggga    180
ccacagttta tcattcaagg atataaggac tatgtggtaa atgaagtggc atctctgttt    240
atctctgctg accggaagct cagcactctg agcctgccct gggtttccct gagagatgct    300
gctgtgtatt actgcattgt gactgacatg gaaactggag ctataaagt ggtctttgga    360 agtgggactc gattgctggt aagccctgac atccagaacc cagaacctgc tgtgtaccag    420
ctgaaagatc tcggagcca ggacagcacc ctctgcctgt tcaccgactt tgactcccag    480
atcaatgtgc ccaaaaccat ggaaagcgga accttcatca ctgacaaaac tgtgctggac    540
atgaaagcta tggattccaa gagcaatggg gccattgcct ggagcaacca gacaagcttc    600
acctgccagg atatcttcaa agagaccaac gccacctacc ccagctccga cgtgccctgt    660
gatgccaccc tgactgagaa aagctttgaa acagatatga acctgaactt tcagaacctg    720
tccgtgatgg gactccggat cctcctgctg aaagtggccg gatttaacct gctcatgacc    780
ctgaggctgt ggtccagctg a                                              801

<210> SEQ ID NO 85
<211> LENGTH: 918
<212> TYPE: PRT
<213> ORGANISM: Artificial Sequence
<220> FEATURE:
<223> OTHER INFORMATION: I8A4 co-1 beta chain

<400> SEQUENCE: 85

Ala Thr Gly Gly Gly Cys Thr Cys Cys Ala Gly Gly Cys Thr Cys Thr
 1               5                  10                  15

Thr Cys Thr Thr Cys Gly Thr Gly Cys Thr Cys Thr Cys Cys Ala Gly
                20                  25                  30

Thr Cys Thr Cys Cys Thr Gly Thr Gly Thr Thr Cys Ala Ala Ala Ala
                35                  40                  45
```

-continued

```
Cys Ala Cys Ala Thr Gly Gly Ala Gly Gly Cys Thr Gly Cys Ala Gly
    50                  55                  60

Thr Cys Ala Cys Cys Cys Ala Ala Ala Gly Cys Cys Cys Ala Ala Gly
65                  70                  75                  80

Ala Ala Ala Cys Ala Ala Gly Gly Thr Gly Gly Cys Ala Gly Thr Ala
                85                  90                  95

Ala Cys Ala Gly Gly Ala Gly Gly Ala Ala Ala Gly Gly Thr Gly Ala
            100                 105                 110

Cys Ala Thr Thr Gly Ala Gly Cys Thr Gly Thr Ala Ala Thr Cys Ala
        115                 120                 125

Gly Ala Cys Thr Ala Ala Thr Ala Ala Cys Cys Ala Cys Ala Ala Cys
    130                 135                 140

Ala Ala Cys Ala Thr Gly Thr Ala Cys Thr Gly Gly Thr Ala Thr Cys
145                 150                 155                 160

Gly Gly Cys Ala Gly Gly Ala Cys Ala Cys Gly Gly Gly Gly Cys Ala
                165                 170                 175

Thr Gly Gly Gly Cys Thr Gly Ala Gly Gly Cys Thr Gly Ala Thr Cys
            180                 185                 190

Cys Ala Thr Thr Ala Thr Thr Cys Ala Thr Ala Thr Gly Gly Thr Gly
        195                 200                 205

Cys Thr Gly Gly Cys Ala Gly Cys Ala Cys Thr Gly Ala Gly Ala Ala
    210                 215                 220

Ala Gly Gly Ala Gly Ala Thr Ala Thr Cys Cys Cys Thr Gly Ala Thr
225                 230                 235                 240

Gly Gly Ala Thr Ala Cys Ala Ala Gly Gly Cys Cys Thr Cys Cys Ala
                245                 250                 255

Gly Ala Cys Cys Ala Ala Gly Cys Cys Ala Ala Gly Ala Gly Ala Ala
            260                 265                 270

Cys Thr Thr Cys Thr Cys Cys Cys Thr Cys Ala Thr Thr Cys Thr Gly
        275                 280                 285

Gly Ala Gly Thr Thr Gly Gly Cys Thr Ala Cys Cys Cys Cys Cys Thr
    290                 295                 300

Cys Thr Cys Ala Gly Ala Cys Ala Thr Cys Ala Gly Thr Gly Thr Ala
305                 310                 315                 320

Cys Thr Thr Cys Thr Gly Thr Gly Cys Cys Ala Gly Cys Gly Cys Cys
                325                 330                 335

Thr Cys Gly Ala Cys Thr Gly Gly Gly Gly Cys Gly Ala Gly Cys Thr
            340                 345                 350

Cys Cys Thr Ala Thr Gly Ala Ala Cys Ala Gly Thr Ala Cys Thr Thr
        355                 360                 365

Cys Gly Gly Thr Cys Cys Cys Gly Gly Cys Ala Cys Cys Ala Gly Gly
    370                 375                 380

Cys Thr Cys Ala Cys Gly Gly Thr Thr Thr Thr Ala Gly Ala Gly Gly
385                 390                 395                 400

Ala Thr Cys Thr Gly Ala Gly Ala Ala Ala Thr Gly Thr Gly Ala Cys
                405                 410                 415

Thr Cys Cys Ala Cys Cys Cys Ala Ala Gly Gly Thr Cys Thr Cys Cys
            420                 425                 430

Cys Thr Gly Thr Thr Thr Gly Ala Gly Cys Cys Ala Thr Cys Cys Ala
        435                 440                 445

Ala Ala Gly Cys Cys Gly Ala Gly Ala Thr Thr Gly Cys Cys Ala Ala
    450                 455                 460
```

```
Cys Ala Ala Ala Cys Ala Ala Ala Gly Gly Cys Thr Ala Cys Cys
465                 470                 475                 480

Cys Thr Gly Gly Thr Gly Thr Gly Cys Cys Thr Gly Gly Cys Cys Ala
                485                 490                 495

Gly Gly Gly Gly Cys Thr Thr Cys Thr Thr Cys Cys Cys Thr Gly Ala
            500                 505                 510

Cys Cys Ala Cys Gly Thr Gly Ala Gly Cys Thr Gly Ala Gly Cys
        515                 520                 525

Thr Gly Gly Thr Gly Gly Thr Gly Ala Thr Gly Gly Cys Gly Ala
    530                 535                 540

Ala Gly Gly Ala Gly Thr Cys Cys Ala Cys Ala Gly Cys Gly Gly
545                 550                 555                 560

Gly Gly Thr Cys Ala Gly Cys Ala Cys Thr Gly Ala Cys Cys Thr
                565                 570                 575

Cys Ala Gly Gly Cys Cys Thr Cys Ala Ala Gly Gly Ala Gly Ala
            580                 585                 590

Gly Cys Ala Ala Thr Thr Ala Thr Ala Gly Cys Thr Ala Cys Thr Gly
    595                 600                 605

Cys Cys Thr Gly Ala Gly Cys Ala Gly Cys Ala Gly Gly Cys Thr Gly
            610                 615                 620

Ala Gly Gly Gly Thr Cys Thr Cys Cys Gly Cys Thr Ala Cys Cys Thr
625                 630                 635                 640

Thr Cys Thr Gly Gly Cys Ala Cys Ala Ala Thr Cys Cys Thr Cys Gly
                645                 650                 655

Gly Ala Ala Cys Cys Ala Cys Thr Thr Cys Ala Gly Gly Thr Gly Cys
            660                 665                 670

Cys Ala Gly Gly Thr Gly Cys Ala Gly Thr Thr Cys Ala Thr Gly
    675                 680                 685

Gly Gly Cys Thr Gly Thr Cys Cys Gly Cys Gly Gly Ala Gly Gly Ala
        690                 695                 700

Cys Ala Ala Gly Thr Gly Gly Cys Cys Ala Gly Ala Gly Gly Gly Cys
705                 710                 715                 720

Thr Cys Cys Cys Thr Ala Ala Ala Cys Cys Thr Gly Thr Cys Ala
            725                 730                 735

Cys Ala Cys Ala Gly Ala Ala Cys Ala Thr Cys Ala Gly Cys Gly Cys
        740                 745                 750

Cys Gly Ala Gly Gly Cys Cys Thr Gly Gly Gly Ala Ala Gly Ala
    755                 760                 765

Gly Cys Cys Gly Ala Cys Thr Gly Thr Gly Gly Ala Ala Thr Cys Ala
770                 775                 780

Cys Thr Thr Cys Cys Gly Cys Cys Thr Cys Cys Ala Thr Cys Ala
            785                 790                 795                 800

Thr Cys Ala Gly Gly Gly Gly Thr Gly Cys Thr Gly Ala Gly Cys
                805                 810                 815

Gly Cys Cys Ala Cys Cys Ala Thr Cys Cys Gly Thr Ala Thr Gly
        820                 825                 830

Ala Gly Ala Thr Cys Cys Thr Gly Cys Thr Gly Gly Gly Ala Ala
    835                 840                 845

Gly Gly Cys Cys Ala Cys Cys Thr Gly Thr Ala Thr Gly Cys Thr
        850                 855                 860

Gly Thr Gly Cys Thr Gly Gly Thr Cys Ala Gly Cys Ala Cys Ala Cys
865                 870                 875                 880

Thr Gly Gly Thr Gly Gly Thr Gly Ala Thr Gly Gly Cys Thr Ala Thr
```

```
                885                 890                 895
Gly Gly Thr Cys Ala Ala Ala Gly Ala Ala Gly Ala Ala Thr
                    900                 905                 910
Thr Cys Cys Thr Gly Ala
        915

<210> SEQ ID NO 86
<211> LENGTH: 819
<212> TYPE: DNA
<213> ORGANISM: Artificial Sequence
<220> FEATURE:
<223> OTHER INFORMATION: I8A4 co-2 alpha chain

<400> SEQUENCE: 86
atgaaacagg tcgccaaagt caccgtgctg ctcattctgg tgtcatggag tctggctaaa      60
accacacagc cccctctat ggaggcttac gagggacagg aagtgaacgt ctcttgctct     120
cacacaaaca ttgccacatc cgagtacatc tactggtacc gacaggtgcc ccatcaggga     180
ccacagttta tcattcaggg atacaaggac tacgtcgtca cgaggtggc ctctctgttc     240 atctctgccg accgaaaact ctctacactg tctctgcctt gggtgtcact gagggatgct     300
gccgtctact actgtattgt gaccgacatg gagactggag ctacaaagt ggtgttcggc     360 tctgggacta gactgctcgt gtctcccgat attcagaacc ctgagcctgc cgtctaccag     420
ctgaaagacc ctaggagtca ggatagtacc ctctgtctct tcaccgactt cgactctcag     480
atcaacgtgc ccaaaacaat ggaatccggg accttcatta ccgacaaaac cgtcctggac     540
atgaaagcca tggatagcaa atccaacggc gctattgctt ggtcaaatca gacctccttc     600
acatgccagg acatttttcaa ggagacaaac gccacatacc cctcttccga tgtgccttgt     660
gatgctaccc tcaccgaaaa atccttcgaa accgatatga acctgaactt ccagaacctc     720
tccgtcatgg gactgaggat tctgctgctg aaagtggctg gcttcaatct cctcatgact     780
ctccgcctct ggtcctccga gggccgagga tctctgctg                             819

<210> SEQ ID NO 87
<211> LENGTH: 918
<212> TYPE: DNA
<213> ORGANISM: Artificial Sequence
<220> FEATURE:
<223> OTHER INFORMATION: I8A4 co-2 beta chain

<400> SEQUENCE: 87
atggggagta ggctgttctt tgtgctgtcc tctctgctgt gttccaaaca catggaggcc      60
gccgtgacac agagtcctag gaacaaagtg gctgtgactg gcggaaaagt gaccctgagc     120
tgtaatcaga ccaacaacca taacaacatg tactggtaca ggcaggatac cggacacgga     180
ctgagactca tccattactc ttacgggct ggctctaccg agaaaggcga tattcccgat     240
ggctacaaag cctctagacc ttctcaggag aacttctccc tcatcctgga actggcaaca     300
ccatctcaga catccgtcta cttttgtgcc tctgcttcta ctggcgcttc ctcctacgag     360
cagtacttcg gacctgggac ccggctcact gtcctggagg atctgaggaa tgtgacaccc     420
cctaaagtgt ctctgttcga accctctaaa gccgaaatcg ccaacaaaca gaaggctacc     480
ctcgtctgtc tggctagggg attcttcccc gatcacgtgg aactctcatg gtgggtgaac     540
ggcaaagaag tccattctgg agtctctacc gatcctcagg cctacaagga gagcaactac     600
tcatactgtc tgtcatctcg gctccgagtg tctgccacat tttggcataa ccccggaac     660 cattttcgct gtcaggtcca gtttcatggc ctgtccgagg aggacaaatg gcccgaggga     720
```

```
tctcctaaac ctgtcactca gaacattagc gctgaggcat ggggacgggc cgattgtgga    780
atcacatctg cctcatacca gcagggagtg ctgagtgcta ctatcctgta cgagatcctg    840
ctcgggaaag ccacactcta cgctgtcctg gtgtctactc tggtggtgat ggctatggtg    900
aaacggaaaa actcctga                                                   918
```

<210> SEQ ID NO 88
<211> LENGTH: 273
<212> TYPE: PRT
<213> ORGANISM: Artificial Sequence
<220> FEATURE:
<223> OTHER INFORMATION: TCR-19 alhpa chain

<400> SEQUENCE: 88

```
Met Met Lys Thr Ser Leu His Thr Val Phe Leu Phe Leu Trp Leu Trp
 1               5                   10                  15

Met Asp Trp Glu Ser His Gly Glu Lys Val Glu Gln His Gln Ser Thr
            20                  25                  30

Leu Ser Val Arg Glu Gly Asp Ser Ala Val Ile Asn Cys Thr Tyr Thr
        35                  40                  45

Asp Thr Ala Ser Ser Tyr Phe Pro Trp Tyr Lys Gln Glu Ala Gly Lys
    50                  55                  60

Ser Leu His Phe Val Ile Asp Ile Arg Ser Asn Val Asp Arg Lys Gln
65                  70                  75                  80

Ser Gln Arg Leu Thr Val Leu Leu Asp Lys Lys Ala Lys Arg Phe Ser
                85                  90                  95

Leu His Ile Thr Ala Thr Gln Pro Glu Asp Ser Ala Ile Tyr Phe Cys
            100                 105                 110

Ala Ala Ser Leu Ile Thr Gly Asn Thr Gly Lys Leu Ile Phe Gly Leu
        115                 120                 125

Gly Thr Thr Leu Gln Val Gln Pro Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser
```

<210> SEQ ID NO 89
<211> LENGTH: 307
<212> TYPE: PRT
<213> ORGANISM: Artificial Sequence
<220> FEATURE:
<223> OTHER INFORMATION: TCR-19 beta chain

<400> SEQUENCE: 89

Met Asn Lys Trp Val Phe Cys Trp Val Thr Leu Cys Leu Leu Thr Val
1               5                   10                  15

Glu Thr Thr His Gly Asp Gly Gly Ile Ile Thr Gln Thr Pro Lys Phe
            20                  25                  30

Leu Ile Gly Gln Glu Gly Gln Lys Leu Thr Leu Lys Cys Gln Gln Asn
        35                  40                  45

Phe Asn His Asp Thr Met Tyr Trp Tyr Arg Gln Asp Ser Gly Lys Gly
    50                  55                  60

Leu Arg Leu Ile Tyr Tyr Ser Ile Thr Glu Asn Asp Leu Gln Lys Gly
65                  70                  75                  80

Asp Leu Ser Glu Gly Tyr Asp Ala Ser Arg Glu Lys Lys Ser Ser Phe
                85                  90                  95

Ser Leu Thr Val Thr Ser Ala Gln Lys Asn Glu Met Ala Val Phe Leu
            100                 105                 110

Cys Ala Ser Ser Leu Thr Ala Asn Thr Glu Val Phe Phe Gly Lys Gly
        115                 120                 125

Thr Arg Leu Thr Val Val Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
    290                 295                 300

Lys Asn Ser
305

<210> SEQ ID NO 90
<211> LENGTH: 822
<212> TYPE: DNA
<213> ORGANISM: Artificial Sequence
<220> FEATURE:
<223> OTHER INFORMATION: TCR-19 alpha chain

<400> SEQUENCE: 90
atgatgaaga catcccttca cactgtattc ctattcttgt ggctatggat ggactgggag    60
agccatggag agaaggtcga gcaacatgag tctacactga gtgttcgaga gggagacagc   120
gctgtcatca actgcactta cacagatact gcttcatcat acttcccttg gtacaagcaa   180

| | |
|---|---|
| gaagctggaa agagtctcca ctttgtgata gacattcgtt caaatgtgga cagaaaacag | 240 |
| agccaaagac ttatagtttt gttggataag aaagccaaac gcttctccct gcacatcaca | 300 |
| gccacacagc ctgaagattc agccatctac ttctgtgcag caagcctcat aacaggcaat | 360 |
| accggaaaac tcatctttgg actgggggaca actttacaag tgcaaccaga catccagaac | 420 |
| ccagaacctg ctgtgtacca gttaaaagat cctcggtctc aggacagcac cctctgcctg | 480 |
| ttcaccgact ttgactccca atcaatgtg ccgaaaacca tggaatctgg aacgttcatc | 540 |
| actgacaaaa ctgtgctgga catgaaagct atggattcca gagcaatgg ggccattgcc | 600 |
| tggagcaacc agacaagctt cacctgccaa gatatcttca agagaccaa cgccacctac | 660 |
| cccagttcag acgttccctg tgatgccacg ttgactgaga aaagctttga acagatatg | 720 |
| aacctaaact ttcaaaacct gtcagttatg ggactccgaa tcctcctgct gaaagtagcc | 780 |
| ggatttaacc tgctcatgac gctgaggctg tggtccagct ga | 822 |

<210> SEQ ID NO 91
<211> LENGTH: 924
<212> TYPE: DNA
<213> ORGANISM: Artificial Sequence
<220> FEATURE:
<223> OTHER INFORMATION: TCR-19 beta chain

<400> SEQUENCE: 91

| | |
|---|---|
| atgaacaagt gggttttctg ctgggtaacc ctttgtctcc ttactgtaga gaccacacat | 60 |
| ggtgatggtg gcatcattac tcagacaccc aaattcctga ttggtcagga agggcaaaaa | 120 |
| ctgaccttga aatgtcaaca gaatttcaat catgatacaa tgtactggta ccgacaggat | 180 |
| tcagggaaag gattgagact gatctactat tcaataactg aaaacgatct tcaaaaaggc | 240 |
| gatctatctg aaggctatga tgcgtctcga gagaagaagt catctttttc tctcactgtg | 300 |
| acatctgccc agaagaacga gatggccgtt tttctctgtg ccagcagttt gacagcaaac | 360 |
| acagaagtct tctttggtaa aggaaccaga ctcacagttg tagaggatct gagaaatgtg | 420 |
| actccacccca aggtctcctt gtttgagcca tcaaaagcag agattgcaaa caacaaaag | 480 |
| gctaccctcg tgtgcttggc caggggcttc ttccctgacc acgtggagct gagctggtgg | 540 |
| gtgaatggca aggaggtcca cagtggggtc agcacggacc ctcaggccta caaggagagc | 600 |
| aattatagct actgcctgag cagccgcctg agggtctctg ctaccttctg cacaatcct | 660 |
| cgaaaccact tccgctgcca agtgcagttc catgggcttt cagaggagga caagtggcca | 720 |
| gagggctcac ccaaacctgt cacacagaac atcagtgcag aggcctgggg ccgagcagac | 780 |
| tgtggaatca cttcagcatc ctatcatcag ggggttctgt ctgcaaccat cctctatgag | 840 |
| atcctactgg gaaaggccac cctatatgct gtgctggtca gtggcctagt gctgatggcc | 900 |
| atggtcaaga aaaaaaattc ctga | 924 |

<210> SEQ ID NO 92
<211> LENGTH: 822
<212> TYPE: DNA
<213> ORGANISM: Artificial Sequence
<220> FEATURE:
<223> OTHER INFORMATION: TCR-19 co-1 alpha chain

<400> SEQUENCE: 92

| | |
|---|---|
| atgatgaaga catccctgca caccgtgttc ctgttcctgt ggctgtggat ggactgggaa | 60 |
| agccatggag agaaggtgga gcagcaccag agcacactga gtgtgagaga gggagacagc | 120 |
| gccgtgatca actgcaccta cacagatacc gccagctcct acttcccttg gtacaagcag | 180 |

```
gaagccggaa agagtctgca ctttgtgatc gacattcgtt ccaatgtgga cagaaaacag    240
agccagagac tgacagtgct gctggataag aaagccaaaa gattctccct gcacatcaca    300
gccacacagc ctgaagattc cgccatctac ttctgtgccg caagcctgat acaggcaat     360 accgaaaac tgatctttgg actggggaca accctgcagg tgcagccaga catccagaac     420
ccagaacctg ctgtgtacca gctgaaagat cctcggagcc aggacagcac cctctgcctg    480
ttcaccgact tgactcccca gatcaatgtg cccaaaacca tggaaagcgg aaccttcatc    540
actgacaaaa ctgtgctgga catgaaagct atggattcca gagcaatgg ggccattgcc     600 tggagcaacc agacaagctt cacctgccag gatatcttca agagaccaa cgccacctac     660 cccagctccg acgtgccctg tgatgccacc ctgactgaga aaagctttga acagatatg     720 aacctgaact tcagaacct gtccgtgatg ggactccgga tcctcctgct gaaagtggcc     780
ggatttaacc tgctcatgac cctgaggctg tggtccagct ga                        822
```

`<210>` SEQ ID NO 93
`<211>` LENGTH: 924
`<212>` TYPE: DNA
`<213>` ORGANISM: Artificial Sequence
`<220>` FEATURE:
`<223>` OTHER INFORMATION: TCR-19 co-1 beta chain

`<400>` SEQUENCE: 93

```
atgaacaagt gggtgttctg ctgggtgacc ctgtgtctgc tgactgtgga gaccacacat     60
ggtgatggtg gcatcattac ccagacaccc aagttcctga ttggtcagga ggggcagaag    120
ctgaccctga agtgtcagca gaatttcaat catgatacaa tgtactggta cagacaggat    180
tccgggaagg gactgagact gatctactat tccatcaccg agaacgatct gcagaagggc    240
gatctgagcg agggctatga tgccagcaga gagaagaagt ccagctttag cctgaccgtg    300
acaagcgccc agaagaacga gatggccgtg tttctgtgtg ccagcagtct gacagccaac    360
acagaggtgt tctttggtaa gggaaccaga ctgacagtgg tggaggatct gagaaatgtg    420
actccaccca aggtgtccct gtttgagcca tccaaagccg agattgccaa caaacaaaag    480
gctaccctgg tgtgcctggc cagggcttc ttccctgacc acgtggagct gagctggtgg    540
gtgaatggca aggaggtcca cagcggggtc agcactgacc ctcaggccta caaggagagc    600
aattatagct actgcctgag cagcaggctg agggtctccg ctaccttctg gcacaatcct    660
cggaaccact tcaggtgcca ggtgcagttc catgggctgt ccgaggagga caagtggcca    720
gagggctccc ctaaacctgt cacacagaac atcagcgccg aggcctgggg aagagccgac    780
tgtggaatca cttccgcctc ctatcatcag gggttctgt ctgcaaccat cctctatgag     840
atcctactgg ggaaggccac cctatatgct gtgctggtca gtggcctagt gctgatggcc    900
atggtcaaga aaaaaaattc ctga                                             924
```

`<210>` SEQ ID NO 94
`<211>` LENGTH: 822
`<212>` TYPE: DNA
`<213>` ORGANISM: Artificial Sequence
`<220>` FEATURE:
`<223>` OTHER INFORMATION: TCR-19 co-2 alpha chain

`<400>` SEQUENCE: 94

```
atgatgaaaa cctccctcca caccgtgttt ctgttcctct ggctctggat ggattgggag     60
tctcacggcg aaaaagtcga gcagcaccag tcaaccctga gtgtccgaga gggcgattct    120
```

```
gctgtgatca actgtaccta caccgatacc gcttcatcct acttcccttg gtacaaacag      180
gaggccggca atcactcca ttttgtcatc gacatccggt ccaacgtgga tagaaaacag      240
tcccagcggc tcactgtcct gctggacaaa aaggctaaac ggttctctct ccatattacc      300
gccacccagc ctgaggatag tgccatctac ttttgtgccg cctctctcat taccggcaat      360
accgggaaac tcatctttgg cctgggaaca acactccagg tccagcccga tattcagaat      420
cctgagcctg ctgtctacca gctgaaggac cctaggagtc aggactccac actctgtctg      480
ttcaccgact tcgattctca gatcaacgtg cccaaaacca tggaatctgg aacattcatt      540
accgacaaaa ctgtgctgga tatgaaggcc atggactcaa aatcaaacgg cgccattgct      600
tggtcaaatc agacctcttt cacctgccag gacatcttta aggagacaaa cgccacatac      660
ccctcttccg atgtgccttg tgatgctact ctcaccgaaa aatcattcga aaccgacatg      720
aacctgaact ttcagaacct ctccgtgatg ggcctgagga tcctcctcct caaagtggct      780
ggcttcaatc tgctcatgac actgagactg tggtcctcat ga                        822
```

<210> SEQ ID NO 95
<211> LENGTH: 924
<212> TYPE: DNA
<213> ORGANISM: Artificial Sequence
<220> FEATURE:
<223> OTHER INFORMATION: TCR-19 co-2 beta chain

<400> SEQUENCE: 95

```
atgaacaaat gggtgttctg ctgggtgaca ctgtgtctgc tcaccgtgga acaacacac       60 ggagatggcg gcatcattac tcagacccca aaattcctca ttggacagga gggccagaaa     120
ctcactctga aatgtcagca gaatttcaac cacgacacca tgtactggta caggcaggat     180
agcggaaaag gcctgagact catctactac tccattaccg agaacgacct ccagaagggc     240
gatctctctg agggatacga tgcctctcgg gaaaaaaaat cctccttctc actcactgtc     300
acatctgccc agaaaaacga atggccgtgt tcctgtgtg cttcttcact caccgccaat     360
accgaagtgt tcttcggcaa gggcactaga ctcactgtgg tcgaggacct ccgaaacgtg     420
actcctccca agtgtctct gttcgaaccc tctaaagccg agattgccaa caaacagaaa     480
gccaccctgg tgtgtctcgc tagaggcttc ttccccgatc atgtggaact gtcttggtgg     540
gtcaacggca agaagtcca ttccggagtc tctaccgatc ctcaggctta caaagagagc     600
aattactcct actgtctgtc tagccgactg agagtgtctg ccacatttg gcacaaccct     660 aggaaccact ttcggtgtca ggtccagttt cacggactgt ccgaggagga caaatggccc     720
gagggatctc ctaaacctgt gactcagaat attagcgccg aggcttgggg acgagccgat     780
tgtgggatta ctagcgcttc ctaccatcag ggagtgctgt ccgccaccat tctgtacgag     840
atcctgctcg gcaaagcaac tctgtacgct gtgctcgtgt ctggactggt gctcatggct     900
atggtcaaga aaaaaaactc atga                                             924
```

<210> SEQ ID NO 96
<211> LENGTH: 268
<212> TYPE: PRT
<213> ORGANISM: Artificial Sequence
<220> FEATURE:
<223> OTHER INFORMATION: TCR-69 alpha chain

<400> SEQUENCE: 96

Met Lys Gln Val Ala Lys Val Thr Val Leu Leu Ile Leu Val Ser Trp
1               5                   10                  15

Ser Leu Ala Lys Thr Thr Gln Pro Pro Ser Met Glu Ala Tyr Glu Gly
            20                  25                  30

Gln Glu Val Asn Val Ser Cys Ser His Thr Asn Ile Ala Thr Ser Glu
        35                  40                  45

Tyr Ile Tyr Trp Tyr Arg Gln Val Pro His Gln Gly Pro Gln Phe Ile
    50                  55                  60

Ile Gln Gly Tyr Lys Asp Tyr Val Val Asn Glu Val Ala Ser Leu Phe
65                  70                  75                  80

Ile Ser Ala Asp Arg Lys Leu Ser Thr Leu Ser Leu Pro Trp Val Ser
                85                  90                  95

Leu Arg Asp Ala Ala Val Tyr Tyr Cys Ile Val Thr Asp Leu Gly Ile
                100                 105                 110

Thr Gly Asn Thr Gly Lys Leu Ile Phe Gly Leu Gly Thr Thr Leu Gln
            115                 120                 125

Val Gln Pro Asp Ile Gln Asn Pro Glu Pro Ala Val Tyr Gln Leu Lys
        130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 97
<211> LENGTH: 304
<212> TYPE: PRT
<213> ORGANISM: Artificial Sequence
<220> FEATURE:
<223> OTHER INFORMATION: TCR-69 beta chain

<400> SEQUENCE: 97

Met Gly Ser Arg Leu Phe Phe Val Leu Ser Ser Leu Leu Cys Ser Lys
1               5                   10                  15

His Met Glu Ala Ala Val Thr Gln Ser Pro Arg Asn Lys Val Ala Val
            20                  25                  30

Thr Gly Gly Lys Val Thr Leu Ser Cys Asn Gln Thr Asn Asn His Asn
        35                  40                  45

Asn Met Tyr Trp Tyr Arg Gln Asp Thr Gly His Gly Leu Arg Leu Ile
    50                  55                  60

His Tyr Ser Tyr Gly Ala Gly Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

Glu Leu Ala Thr Pro Ser Gln Thr Ser Val Tyr Phe Cys Ala Ser Gly
                100                 105                 110

```
Asp Glu Gly Tyr Asn Ser Pro Leu Tyr Phe Ala Ala Gly Thr Arg Leu
            115                 120                 125

Thr Val Thr Glu Asp Leu Arg Asn Val Thr Pro Lys Val Ser Leu
        130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

<210> SEQ ID NO 98
<211> LENGTH: 807
<212> TYPE: DNA
<213> ORGANISM: Artificial Sequence
<220> FEATURE:
<223> OTHER INFORMATION: TCR-69 alpha chain

<400> SEQUENCE: 98
atgaagcagg tggcaaaagt gactgtgctc ctgatcttgg tctcatggag ccttgccaag    60
accacccagc cccctccat ggaggcctat gaagggcaag aagtgaacgt gtcctgcagc    120
catacaaaca ttgctacaag cgagtacatc tattggtacc gacaggttcc ccaccaggga   180
ccacagttta tcattcaagg atataaggac tatgtggtaa atgaagtggc atctctgttt   240
atctctgctg accggaagct cagcactctg agcctgccct gggtttccct gagagatgct   300
gctgtgtatt actgcattgt gactgacctg gggataacag caataccgg aaaactcatc    360
tttggactgg gacaacttt acaagtgcaa ccagacatcc agaacccaga acctgctgtg    420
taccagttaa agatcctcg gtctcaggac agcaccctct gcctgttcac cgactttgac    480
tcccaaatca atgtgccgaa aaccatggaa tctggaacgt tcatcactga caaaactgtg   540
ctggacatga agctatgga ttccaagagc aatggggcca ttgcctggag caaccagaca   600
agcttcacct gccaagatat cttcaaagag accaacgcca cctacccag ttcagacgtt    660
ccctgtgatg ccacgttgac tgagaaaagc tttgaaacag atatgaacct aaactttcaa   720
aacctgtcag ttatgggact ccgaatcctc ctgctgaaag tagccggatt taacctgctc   780
atgacgctga ggctgtggtc cagctga                                       807

<210> SEQ ID NO 99
<211> LENGTH: 915
<212> TYPE: DNA
<213> ORGANISM: Artificial Sequence
```

<220> FEATURE:
<223> OTHER INFORMATION: TCR-69 beta chain

<400> SEQUENCE: 99

```
atgggctcca ggctcttctt cgtgctctcc agtctcctgt gttcaaaaca catggaggct    60
gcagtcaccc aaagcccaag aaacaaggtg cagtaacag gaggaaaggt gacattgagc    120
tgtaatcaga ctaataacca caacaacatg tactggtatc ggcaggacac ggggcatggg   180
ctgaggctga tccattattc atatggtgct ggcagcactg agaaggaga tatccctgat    240
ggatacaagg cctccagacc aagccaagag aacttctccc tcattctgga gttggctacc   300
ccctctcaga catcagtgta cttctgtgcc agcggtgatg agggatataa ttcgccctc    360
tactttgcgg caggcacccg gctcactgtg acagaggatc tgagaaatgt gactccaccc   420
aaggtctcct tgtttgagcc atcaaaagca gagattgcaa acaaacaaaa ggctaccctc   480
gtgtgcttgg ccaggggctt cttccctgac cacgtggagc tgagctggtg ggtgaatggc   540
aaggaggtcc acagtggggt cagcacggac cctcaggcct acaaggagag caattatagc   600
tactgcctga gcagccgcct gagggtctct gctaccttct ggcacaatcc tcgaaaccac   660
ttccgctgcc aagtgcagtt ccatgggctt tcagaggagg acaagtggcc agagggctca   720
cccaaacctg tcacacagaa catcagtgca gaggcctggg gccgagcaga ctgtggaatc   780
acttcagcat cctatcatca gggggttctg tctgcaacca tcctctatga gatcctactg   840
gggaaggcca ccctgtatgc tgtgcttgtc agtacactgg tggtgatggc tatggtcaaa   900
agaaagaatt catga                                                    915
```

<210> SEQ ID NO 100
<211> LENGTH: 807
<212> TYPE: DNA
<213> ORGANISM: Artificial Sequence
<220> FEATURE:
<223> OTHER INFORMATION: TCR-69 co -1 alpha chain

<400> SEQUENCE: 100

```
atgaagcagg tggccaaagt gaccgtgctg ctgatccttg tgtcttggag cctggccaag    60
accacccagc cccctccat ggaggcctat gaagggcagg aagtgaacgt gtcctgcagc   120
catacaaaca ttgccacaag cgagtacatc tattggtaca gacaggtgcc tcaccaggga   180
ccacagtttt a tcattcaggg atataaggac tatgtggtga tgaagtggc tagcctgttt   240
atcagcgctg atagaaagct gagcacactg agcctgccct gggtgtccct gagagatgcc   300
gccgtgtatt actgcattgt gaccgacctg gggatcacag caataccgg aaaactgatc   360
tttggactgg ggacaaccct gcaggtgcag ccagacatcc agaacccaga acctgctgtg   420
taccagctga aagatcctcg gagccaggac agcaccctct gcctgttcac cgactttgac   480
tcccagatca atgtgcccaa accatggaa agcggaacct tcatcactga caaaactgtg   540
ctggacatga agctatgga ttccaagagc aatgggcca ttgcctggag caaccagaca   600
agcttcacct gccaggatat cttcaaagag accaacgcca cctacccag ctccgacgtg   660
ccctgtgatg ccacctgac tgagaaaagc tttgaaacag atatgaacct gaactttcag   720
aacctgtccg tgatgggact ccggatcctc ctgctgaaag tggccggatt taacctgctc   780
atgaccctga ggctgtggtc cagctga                                      807
```

<210> SEQ ID NO 101
<211> LENGTH: 915
<212> TYPE: DNA

<213> ORGANISM: Artificial Sequence
<220> FEATURE:
<223> OTHER INFORMATION: TCR-69 co -1 beta chain

<400> SEQUENCE: 101

```
atgggctcca ggctgttctt cgtgctgtcc agtctgctgt gttccaaaca catggaggcc      60
gccgtgaccc agagcccaag aaacaaggtg gccgtgacag gaggaaaggt gacactgagc     120
tgtaatcaga ccaataacca caacaacatg tactggtatc ggcaggacac ggggcatggg     180
ctgaggctga tccattattc ctatggagcc ggcagcaccg agaaggaga tatccctgat      240
ggatacaagg cctccagacc aagccaggag aacttctccc tgattctgga gctggccacc     300
cccagccaga catccgtgta cttctgtgcc agcggagatg agggatataa ttccccctg      360
tactttgccg ccggcacccg gctgaccgtg acagaggatc tgagaaatgt gaccccaccc     420
aaggtgtccc tgtttgagcc atccaaagcc gagattgcca caaacaaaa ggctaccctg      480
gtgtgcctgg ccaggggctt cttccctgac cacgtggagc tgagctggtg ggtgaatggc     540
aaggaggtcc acagcggggt cagcactgac cctcaggcct acaaggagag caattatagc     600
tactgcctga gcagcaggct gagggtctcc gctaccttct ggcacaatcc tcggaaccac     660
ttcaggtgcc aggtgcagtt ccatgggctg tccgaggagg acagtggcc agagggctcc      720
cctaaacctg tcacacagaa catcagcgcc gaggcctggg gaagagccga ctgtggaatc     780
acttccgcct cctatcatca ggggtgctg agcgccacca tcctgtatga gatcctgctg     840
gggaaggcca ccctgtatgc tgtgctggtc agcacactgg tggtgatggc tatggtcaaa     900
agaaagaatt cctga                                                     915
```

<210> SEQ ID NO 102
<211> LENGTH: 807
<212> TYPE: DNA
<213> ORGANISM: Artificial Sequence
<220> FEATURE:
<223> OTHER INFORMATION: TCR-69 co -2 alpha chain

<400> SEQUENCE: 102

```
atgaaacagg tcgccaaagt caccgtgctg ctcattctgg tgtcatggag tctggctaaa      60
accacacagc cccctctat ggaggcttac gagggacagg aagtgaacgt ctcttgctct     120
cacacaaaca ttgccacatc cgagtacatc tactggtaca gacaggtgcc ccatcaggga     180
ccacagttta tcatccaggg atacaaggac tacgtcgtca acgaggtggc ctctctcttc     240
atttctgccg accggaaact ctctacactg tcactgccat gggtgtcact ccagagatgct     300
gccgtctact actgtattgt gaccgatctg ggcattactg ggaataccgg gaaactcatc     360
ttcggcctgg gaacaacact ccaggtccag cccgacattc agaatcctga acctgccgtc     420
taccagctga agaccctag agccaggat agtaccctgt gcctgttcac cgatttcgac      480
tcacagatca acgtgcccaa aacaatggaa tccggaacat tcatcaccga caaaaccgtc     540
ctcgacatga aagccatgga ctcaaaaatcc aatggcgcta ttgcctggtc aaatcagacc     600
tccttcacat gccaggacat tttcaaggag acaaacgcca cttaccctc atccgatgtg      660
ccttgtgatg ctaccctcac tgaaaaaatca ttcgaaaccg atatgaatct caacttccag     720
aacctctccg tcatgggact gagaattctg ctgctgaaag tggccggctt caatctcctc     780
atgactctcc gcctctggtc atcttaa                                        807
```

<210> SEQ ID NO 103
<211> LENGTH: 915

<212> TYPE: DNA
<213> ORGANISM: Artificial Sequence
<220> FEATURE:
<223> OTHER INFORMATION: TCR-69 co -2 beta chain

<400> SEQUENCE: 103

```
atgggctctc gactgttctt tgtgctctcc tctctgctgt gttccaaaca catggaggct      60
gctgtcacac agagtcctcg gaacaaagtg gccgtgaccg gcggcaaagt caccctgagc     120
tgtaatcaga ccaacaatca taacaacatg tactggtaca ggcaggatac tggacatgga     180
ctgagactca tccactactc ttacggcgct ggatcaaccg aaaaaggcga catccccgat     240
ggctacaaag cttctagacc ctctcaggag aactttagcc tcattctgga actggccaca     300
ccatcacaga ctagcgtgta cttttgtgcc tctggcgacg agggatacaa ttcacccctc     360
tacttcgctg ctgggactag gctcactgtc actgaggatc tccgaaacgt cactcccccc     420
aaagtgtccc tgttcgaacc ttctaaggcc gaaattgcca caaacagaa agcaaccctg      480
gtctgtctgg ctagaggctt ctttcccgat cacgtggaac tctcatggtg ggtcaacggc     540
aaagaggtcc actctggagt ctctaccgat ccacaggctt acaaggagtc caattactcc     600
tactgtctct cttcacgact ccgggtgtcc gccacatttt ggcataaccc ccggaatcac     660
ttcagatgtc aggtccagtt tcacggactg tctgaggagg acaaatggcc tgagggatcc     720
cctaaacccg tcacccagaa catttctgcc gaggcatggg gacgagccga ttgtggcatc     780
actagcgcct cttaccatca gggcgtgctg tctgctacaa ttctgtacga gattctgctc     840
ggaaaagcca cactgtacgc tgtcctggtg tctacactgg tggtcatggc tatggtcaaa     900
cggaaaaact cttga                                                      915
```

<210> SEQ ID NO 104
<211> LENGTH: 25
<212> TYPE: PRT
<213> ORGANISM: Artificial Sequence
<220> FEATURE:
<223> OTHER INFORMATION: TCR-19 CD3 region for alpha chain

<400> SEQUENCE: 104

Cys Ala Ala Ser Leu Ile Thr Gly Asn Thr Gly Lys Leu Ile Phe Gly
1               5                   10                  15
Leu Gly Thr Thr Leu Gln Val Gln Pro
            20                  25

<210> SEQ ID NO 105
<211> LENGTH: 22
<212> TYPE: PRT
<213> ORGANISM: Artificial Sequence
<220> FEATURE:
<223> OTHER INFORMATION: TCR-19 CD3 region for beta chain

<400> SEQUENCE: 105

Cys Ala Ser Ser Leu Thr Ala Asn Thr Glu Val Phe Phe Gly Lys Gly
1               5                   10                  15
Thr Arg Leu Thr Val Val
            20

<210> SEQ ID NO 106
<211> LENGTH: 23
<212> TYPE: PRT
<213> ORGANISM: Artificial Sequence
<220> FEATURE:
<223> OTHER INFORMATION: TCR-69 CD3 region for alpha chain

```
<400> SEQUENCE: 106

Cys Ala Ser Gly Asp Glu Gly Tyr Asn Ser Pro Leu Tyr Phe Ala Ala
1               5                   10                  15

Gly Thr Arg Leu Thr Val Thr
            20

<210> SEQ ID NO 107
<211> LENGTH: 27
<212> TYPE: PRT
<213> ORGANISM: Artificial Sequence
<220> FEATURE:
<223> OTHER INFORMATION: TCR-69 CD3 region for beta chain

<400> SEQUENCE: 107

Cys Ile Val Thr Asp Leu Gly Ile Thr Gly Asn Thr Gly Lys Leu Ile
1               5                   10                  15

Phe Gly Leu Gly Thr Thr Leu Gln Val Gln Pro
            20                  25

<210> SEQ ID NO 108
<211> LENGTH: 9
<212> TYPE: PRT
<213> ORGANISM: Artificial Sequence
<220> FEATURE:
<223> OTHER INFORMATION: HCV gt 1a

<400> SEQUENCE: 108

Cys Ile Asn Gly Val Cys Trp Thr Val
1               5

<210> SEQ ID NO 109
<211> LENGTH: 9
<212> TYPE: PRT
<213> ORGANISM: Artificial Sequence
<220> FEATURE:
<223> OTHER INFORMATION: HCV gt 1b

<400> SEQUENCE: 109

Cys Val Asn Gly Val Cys Trp Thr Val
1               5

<210> SEQ ID NO 110
<211> LENGTH: 9
<212> TYPE: PRT
<213> ORGANISM: Artificial Sequence
<220> FEATURE:
<223> OTHER INFORMATION: HCV gt 2

<400> SEQUENCE: 110

Thr Ile Ser Gly Val Leu Trp Thr Val
1               5

<210> SEQ ID NO 111
<211> LENGTH: 9
<212> TYPE: PRT
<213> ORGANISM: Artificial Sequence
<220> FEATURE:
<223> OTHER INFORMATION: HCV gt 3

<400> SEQUENCE: 111

Thr Ile Gly Gly Val Met Trp Thr Val
1               5

<210> SEQ ID NO 112
<211> LENGTH: 9
```

```
<212> TYPE: PRT
<213> ORGANISM: Artificial Sequence
<220> FEATURE:
<223> OTHER INFORMATION: HCV gt 4

<400> SEQUENCE: 112

Ala Val Asn Gly Val Met Trp Thr Val
 1               5

<210> SEQ ID NO 113
<211> LENGTH: 9
<212> TYPE: PRT
<213> ORGANISM: Artificial Sequence
<220> FEATURE:
<223> OTHER INFORMATION: HCV gt 5

<400> SEQUENCE: 113

Cys Ile Asn Gly Val Met Trp Thr Val
 1               5

<210> SEQ ID NO 114
<211> LENGTH: 9
<212> TYPE: PRT
<213> ORGANISM: Artificial Sequence
<220> FEATURE:
<223> OTHER INFORMATION: HCV gt 6

<400> SEQUENCE: 114

Ala Ile Asn Gly Val Met Trp Thr Val
 1               5

<210> SEQ ID NO 115
<211> LENGTH: 9
<212> TYPE: PRT
<213> ORGANISM: Artificial Sequence
<220> FEATURE:
<223> OTHER INFORMATION: Flu

<400> SEQUENCE: 115

Cys Val Asn Gly Ser Cys Phe Thr Val
 1               5

<210> SEQ ID NO 116
<211> LENGTH: 11
<212> TYPE: PRT
<213> ORGANISM: Artificial Sequence
<220> FEATURE:
<223> OTHER INFORMATION: HCV NS5 2221

<400> SEQUENCE: 116

Ser Pro Asp Ala Asp Leu Ile Glu Ala Asn Leu
 1               5                  10

<210> SEQ ID NO 117
<211> LENGTH: 9
<212> TYPE: PRT
<213> ORGANISM: Artificial Sequence
<220> FEATURE:
<223> OTHER INFORMATION: HCV NS5 1992

<400> SEQUENCE: 117

Val Leu Thr Asp Phe Lys Thr Trp Leu
 1               5

<210> SEQ ID NO 118
<211> LENGTH: 9
<212> TYPE: PRT
```

```
<213> ORGANISM: Artificial Sequence
<220> FEATURE:
<223> OTHER INFORMATION: HCMV pp65 495

<400> SEQUENCE: 118

Asn Leu Val Pro Met Val Ala Thr Val
 1               5

<210> SEQ ID NO 119
<211> LENGTH: 25
<212> TYPE: PRT
<213> ORGANISM: Artificial Sequence
<220> FEATURE:
<223> OTHER INFORMATION: I8A4 CDR3 region for alpha chain (alternative)

<400> SEQUENCE: 119

Cys Ile Val Thr Asp Met Glu Thr Gly Gly Tyr Lys Val Val Phe Gly
 1               5                  10                  15

Ser Gly Thr Arg Leu Leu Val Ser Pro
            20                  25
```

T CELL RECEPTORS SPECIFIC FOR IMMUNODOMINANT CTL EPITOPES OF HCV

CROSS REFERENCE TO RELATED APPLICATIONS

This application claims the benefit and priority to and is a U.S. National Phase Application of PCT International Application Number PCT/IB2010/003155, filed on Nov. 23, 2010, designating the United States of America and published in the English language, which is an International Application of and claims the benefit of priority to U.S. Provisional Application No. 61/264,155, filed on Nov. 24, 2009. The disclosures of the above-referenced applications are hereby expressly incorporated by reference in their entireties.

CROSS-REFERENCE TO RELATED APPLICATIONS

This application claims the benefit of priority to U.S. Application No. 61/264,155, filed Nov. 24, 2009, which is hereby expressly incorporated by reference in its entirety.

REFERENCE TO SEQUENCE LISTING

The present application is being filed along with a Sequence Listing in electronic format. The Sequence Listing is provided as a file entitled TRIPEP114WO.TXT, created Nov. 22, 2010, which is 79 KB in size. The information in the electronic format of the Sequence Listing is incorporated herein by reference in its entirety.

FIELD OF THE INVENTION

The present invention relates generally to the field of immunology. More particularly, aspects of the invention concern the discovery of several T cell receptors (TCRs) that are specific for immunodominant epitopes of hepatitis C virus (HCV). Embodiments include TCRs, DNAs encoding TCRS, methods of making TCRs, and methods of using TCRs to treat, prevent or inhibit hepatitis C virus (HCV) proliferation.

BACKGROUND OF THE INVENTION

Since the identification of HCV in 1989, it is today estimated that 180 million individuals are infected worldwide of which 130 million are chronic HCV carriers at risk of developing liver cirrhosis and/or liver cancer. See Kantzanou, M., et al. (2003) Viral escape and T cell exhaustion in hepatitis C virus infection analysed using Class I peptide tetramer, Immunol Lett 85:165-71, which is hereby incorporated by reference in its entirety. Being a small enveloped RNA virus, HCV is one of the most persistent viruses in humans. Spontaneous resolution of HCV infection occurs in a minority of infected individuals. See Alter, H. 2006. Viral hepatitis. Hepatology 43:S230-4, which is hereby incorporated by reference in its entirety. Considering the steady increase of reported incidence in Europe and the fact that current interferon therapy is only 50-60% effective, a reduction of HCV prevalence is not anticipated in the near future. Several promising HCV specific inhibitors designed to impair the protease/polymerase activity of HCV non-structural proteins (NS) 3-5 are currently in clinical evaluation. See Kronenberger, B., and S. Zeuzem, (2009) Current and future treatment options for HCV. Ann Hepatol 8:103-12, which is hereby incorporated by reference in its entirety.

Based on analysis of individuals who have resolved HCV infection, it appears that a successful immunity requires T cell control and clearance. Bowen, D. G., and C. M. Walker, (2005) Adaptive immune responses in acute and chronic hepatitis C virus infection, Nature 436:946-52. It is now known that CD4+ and CD8+ lymphocyte activation early in the infection is strongly associated with eradication of HCV infection, and an early development of polyfunctional T cells may further predict a spontaneous resolution of HCV infection. Failure to sustain virus-specific CD8+ lymphocytes may, on the other hand, contribute to persistence of the virus. Lechner, F., N. H. Gruener, S. Urbani, J. Uggeri, T. Santantonio, A. R. Kammer, A. Cerny, R. Phillips, C. Ferrari, G. R. Pape, and P. Klenerman. (2000) CD8+ T lymphocyte responses are induced during acute hepatitis C virus infection but are not sustained, Eur J Immunol 30:2479-87, which is hereby incorporated by reference in its entirety. Features in HCV-specific T lymphocytes, such as, functional exhaustion, developmental arrest, tolerance induction, impairment in proliferative capacity and effector function are often observed in the chronic phase of infection. Some believe these events are a consequence of continued antigen stimulation, or a viral factor leading to Antigen Presentation Cell (APC) suppression, but considerable uncertainty still remains. Nevertheless, it appears that dysfunctional effector T cells ineffectively control the infection and the persistence of the virus leads to long-term liver damage in the host.

Many studies have investigated HCV infection and the host immune response, however, very often these studies are conducted in an allogeneic setting by assessing the magnitude of lymphocytic activity in mixed lymphocyte reactions. Bona fide HCV antiviral lymphocytic activations have been examined in very few studies. The limited number of existing human HCV T-cell clones could be one explanation, however, the relatively short lifespan of primary T cell lines is surely a contributing factor. The need for a better understanding of how HCV and HCV-infected cells are recognized and responded to by the immune system is manifest.

SUMMARY OF THE INVENTION

Several approaches to make murine T cell hybridomas that are specific for a variety of epitopes of pathogens and/or allergens (e.g., human viral epitopes such as, hepatitis, in particular, HCV) have been discovered. The robust methods described herein facilitate the production and isolation of T cell receptors (TCRs) and nucleic acids encoding said TCRs because the approaches avoid having to use primary human T cell cultures. Since murine TCRs are less likely to interfere or mispair with endogenous human TCRs, the methods provided herein generate very specific TCRs with high efficiency.

Accordingly, several embodiments, for example, concern the identification and immortalization of several T cell clones with specificity to the human HLA-A2 restricted NS3 Cytolytic T lymphocytes (CTL) epitope. The T cell clones were raised in the human HLA (HHD) transgenic mice and functional and TCR gene analyses showed that the clones are polyfunctional and monoclonal (e.g., they differ in several aspects including the functional avidity, affinity to the NS3/HLA-complex pentamer and the genes encoding TCR alpha and beta chains). Moreover, the clones described herein will provide high affinity TCRs because the response to exogenously or endogenously processed NS3 peptide target was CD8 co-receptor independent. DNAs encoding the TCRs described herein can be introduced into constructs with and without a suicide gene (e.g., HSV-TK) and the constructs can be introduced into packaging cell lines so as to produce retroviral vectors. The retroviral vectors can then be used to introduce the DNA encoding the TCRs described herein into T cells, preferably, T cells isolated from a subject in need of an agent that inhibits the proliferation of HCV. T cells expressing the TCRs described herein can then be re-introduced into the subject and, if the T cells contain the suicide gene (e.g., HSV-TK), the T cells can be eliminated by providing said subject acyclovir or gancyclovir or a suitable analog. Accordingly, embodiments include the DNAs and peptides described herein and cells containing these molecules, as well as, methods of generating TCRs, especially CD8-independent TCRs, and methods of treating, inhibiting, and/or prophylaxis of HCV.

Several embodiments described herein concern an isolated polypeptide comprising a T cell receptor (TCR) specific for an NS3 or NS5 peptide. In some embodiments, the TCR is specific for an NS3 peptide corresponding to amino acid residues 1073-1081 of HCV-1a. The TCR can comprise, consist essentially of, or consist of, for example, a polypeptide sequence, or a fragment thereof (e.g., at least, equal to, greater than, or less than, or any number in between 3, 5, 8, 10, 12, 15, 18, 20, 21, 22, 23, 24, 25, 50, 75, 100, 125, 150, or 175 consecutive amino acids of the polypeptide sequence) selected from the group consisting of SEQ ID NOS: 1-9, SEQ ID NO: 72, SEQ ID NO: 73, SEQ ID NO: 80, SEQ ID NO: 81 and SEQ ID NO 119. The TCR can also be CD8 independent. A nucleic acid encoding any one of the isolated polypeptides (including fragments thereof) described above, for example, a sequence selected from the group consisting of SEQ ID NOS: 63-71, SEQ ID NOS: 74-79 and SEQ ID NOS: 82-87 is also an embodiment. In some embodiments, the nucleic acid sequence is codon-optimized for expression in a subject needing an immune response specific to an NS3 peptide (e.g., a human infected with HCV). Non-limiting examples of codon-optimized nucleic acids encoding said isolated polypeptides include SEQ ID NOS: 76-79 and SEQ ID NOS: 84-87. In some embodiments, said nucleic acid comprises a nucleotide sequence comprising at least one substitution of a different codon (e.g., at least one, at least three, at least five, at least ten, or at least fifteen codon substitutions) that encodes a functionally equivalent amino acid (e.g., the same amino acid). The codon substitutions may, for example, improve expression when administered to a subject needing an immune response specific to an NS3 peptide (e.g., a human infected with HCV). Non-limiting examples of nucleic acids with codon substitutions that encode said isolated polypeptide sequences include SEQ ID NOS: 76-79 and SEQ ID NOS: 84-87. Further, constructs, retroviral vectors, isolated cells, in particular, isolated T cells that comprise the nucleic acids and/or proteins above are also embodiments. Antibodies or fragments thereof that are specific for the isolated peptides above are also embodiments.

Several embodiments described herein concern an isolated polypeptide comprising a T cell receptor (TCR) specific for an NS5 peptide. In some embodiments, the TCR is specific for an NS5 peptide corresponding to amino acid residues 1992-2000 of HCV-1a. The TCR can comprise, consist essentially of, or consist of, for example, a polypeptide sequence, or a fragment thereof (e.g., at least, equal to, greater than, or less than, or any number in between 3, 5, 8, 10, 12, 15, 18, 20, 21, 22, 23, 24, 25, 50, 75, 100, 125, 150, or 175 consecutive amino acids of the polypeptide sequence) selected from the group consisting of SEQ ID NOS: 88, SEQ ID NO: 89, SEQ ID NO: 96, SEQ ID NO: 97, SEQ ID NO: 104, SEQ ID NO: 105, SEQ ID NO: 106, and SEQ ID NO: 107. The TCR can also be CD8 independent. A nucleic acid encoding any one of the isolated polypeptides described above, for example, a sequence selected from the group consisting of SEQ ID NOS: 90-95 and SEQ ID NOS: 98-103 is also an embodiment. In some embodiments, the nucleic acid sequence is codon-optimized for expression in a subject needing an immune response specific to an NS5 peptide (e.g., a human infected with HCV). Non-limiting examples of codon-optimized nucleic acids encoding a polypeptide sequences encoding said isolated polypeptides include SEQ ID NOS: 92-95 and SEQ ID NOS: 100-103. In some embodiments, said nucleic acid comprises a nucleotide sequence comprising at least one substitution of a different codon (e.g., at least one, at least three, at least five, at least ten, or at least fifteen codon substitutions) that encodes a functionally equivalent amino acid (e.g., the same amino acid). The codon substitutions may, for example, improve expression when administered to a subject needing an immune response specific to an NS5 peptide (e.g., a human infected with HCV). Non-limiting examples of nucleic acids with codon substitutions that encode said isolated polypeptide sequences include SEQ ID NOS: 92-95 and SEQ ID NOS: 100-103. Further, constructs, retroviral vectors, isolated cells, in particular, isolated T cells that comprise the nucleic acids and/or proteins above are also embodiments. Antibodies or fragments thereof that are specific for the isolated peptides above are also embodiments.

Some embodiments include nucleic acids that have homology or sequence identity to any one of the nucleic acid sequences disclosed herein (e.g. SEQ. ID. NOS. 74-79, 82-87, 90-95, 98-103, etc.). Several techniques exist to determine nucleic acid or protein sequence homology. Thus, embodiments of the nucleic acids can have from 70% homology or sequence identity to 100% homology or sequence identity to any one of the nucleic acid sequences or protein sequences disclosed herein. That is, embodiments can have at least, equal to or any number between about 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% homology or sequence identity to any one of the polypeptide or nucleic acid sequences disclosed herein. Further, constructs, retroviral vectors, isolated cells, in particular, isolated T cells that comprise the nucleic acids having the above-discussed homology or sequence identity are also embodiments.

Some embodiments included isolated nucleic acids having sufficient homology or sequence identity to any one of the nucleic acid sequences disclosed herein such that hybridization will occur between the isolated nucleic acid and any one of the nucleic acids sequences disclosed herein. In some aspects, hybridization occurs under usual washing conditions in Southern hybridization, that is, at a salt concentration corresponding to 0.1 times saline sodium citrate (SSC) and 0.1% SDS at 37° C. (low stringency), preferably 0.1 times SSC and 0.1% SDS at 60° C. (medium stringency), and more preferably 0.1 times SSC and 0.1% SDS at 65° C. (high stringency). In certain aspects, the nucleic acid embodiments have a percentage of consecutive bases that hybridize under stringent conditions with any one of the nucleic acids sequences disclosed herein, where the number of consecutive bases is at least 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% of the total number of bases in the nucleic acid sequence. Further, constructs, retroviral vectors, isolated cells, in particular, isolated T cells that comprise the nucleic acid having the above-discussed sufficient homology or sequence identity are also embodiments.

Some embodiments include polypeptides that have homology or sequence identity to any one of the polypeptide sequences disclosed herein (e.g. SEQ. ID. Nos. 1-9, 72, 73, 80, 81, 88, 89, 96, 97, 119, etc.). In some embodiments, said polypeptides generate, enhance, or improve an immune response, as defined above. Several techniques exist to determine protein sequence homology or sequence identity. Thus, embodiments of the polypeptides can have from 70% homology to 100% homology or sequence identity to any one of the polypeptides disclosed herein. That is, embodiments can have at least, equal to, or any number in between about 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% homology or sequence identity to any one of the polypeptide or nucleic acid sequences disclosed herein. Further, constructs, retroviral vectors, isolated cells, in particular, isolated T cells that comprise the polypeptide and/or nucleic acids encoding the polypeptide, where said polypeptide has the above-discussed homology or sequence identity are also embodiments.

Aspects of the invention also concern a method of making a nucleic acid that encodes a TCR specific for a candidate peptide. By some approaches these methods are practiced by immunizing a human HLA (HHD) transgenic mouse with a candidate peptide; isolating spleencocytes from the immunized transgenic mouse isolating spleencocytes from the immunized transgenic mouse; generating hybridomas that comprise T-cells from said spleencocytes; isolating hybridomas that comprise a TCR specific to said candidate peptide; obtaining RNA from said hybridomas that encode said TCR; and generating cDNA from said RNA. In some embodiments, the above methods are practiced, wherein said candidate peptide is a hepatitis peptide, including but not limited to a hepatitis B virus (HBV) peptide such as a HBV core peptide, a hepatitis C virus (HCV) peptide, such as an NS3 or NS5 peptide, in particular an $NS3_{1073-1081}$ or $NS5_{1992-2000}$ peptide. In some embodiments, the above methods are practiced, wherein said candidate peptide is a Japanese Encephalitis virus (JeV) peptide or a Birch allergen peptide. In some embodiments, the methods further comprise cloning said cDNA into a construct, which may be a retroviral vector.

Aspects of the invention also include methods of inhibiting proliferation of HCV. Several of these methods are practiced by immunizing a human HLA (HHD) transgenic mouse with an HCV peptide; isolating spleencocytes from the immunized transgenic mouse; isolating spleencocytes from the immunized transgenic mouse; generating hybridomas that comprise T-cells from said spleencocytes; isolating hybridomas that comprise a TCR specific to said candidate peptide; obtaining RNA from said hybridomas that encodes said TCR; generating cDNA from said RNA; incorporating said cDNA into a retroviral expression system; producing retrovirus comprising said cDNA; obtaining T cells from a subject in need of an agent that inhibits the proliferation of HCV; infecting said T cells with said retrovirus; and providing said infected T cells to said subject. In some embodiments, the above methods are practiced, wherein said HCV peptide is an NS3 peptide, in particular the $NS3_{1073-1081}$ peptide. In some embodiments, the above methods are practiced, wherein said HCV peptide is an NS5 peptide, in particular the $NS5_{1992-2000}$ peptide. In some embodiments, the above methods are practiced, wherein said infected T cells further comprise a gene encoding HSV-TK. These methods cam also further comprise measuring the level or amount of HCV infection before and/or after providing said infected T cells to said subject.

BRIEF DESCRIPTION OF THE DRAWINGS

FIG. 4 (A) Summary of reactivity to mutant peptide analogs given as percentage reactivity relative to the wild type (WT) $NS3_{1073}$ peptide. Hybridomas were stimulated with T2 target cells loaded with or without the indicated peptide mutated at indicated position (pos 1-9, 10 ug/ml) in duplicate co-cultures and tested for IL-2. The reactivity is given in percentage relative to its response to WT peptide. The IL-2 concentration produced by each hybridoma stimulated with WT peptide target is set as 100%. Reactivity below 25% relative to its WT peptide reactivity is filled with grey. (B) The EC50 of WT and the respective mutant peptide (ng/ml peptide) for each hybridoma. The EC50 values represent peptide concentrations at which half-maximum IL-2 production reaches the WT response. EC50<100 ng/ml is filled with grey.

FIG. 9 TCR alpha and beta chain CDR3 region of the indicated hybridoma clone. (A) TCR-19 alpha chain (SEQ ID NO. 104) and TCR-19 beta chain (SEQ ID NO. 105). (B) TCR-69 alpha chain (SEQ ID NO. 106) and TCR-69 beta chain (SEQ ID NO. 107).

DETAILED DESCRIPTION OF THE INVENTION

Figure 1:
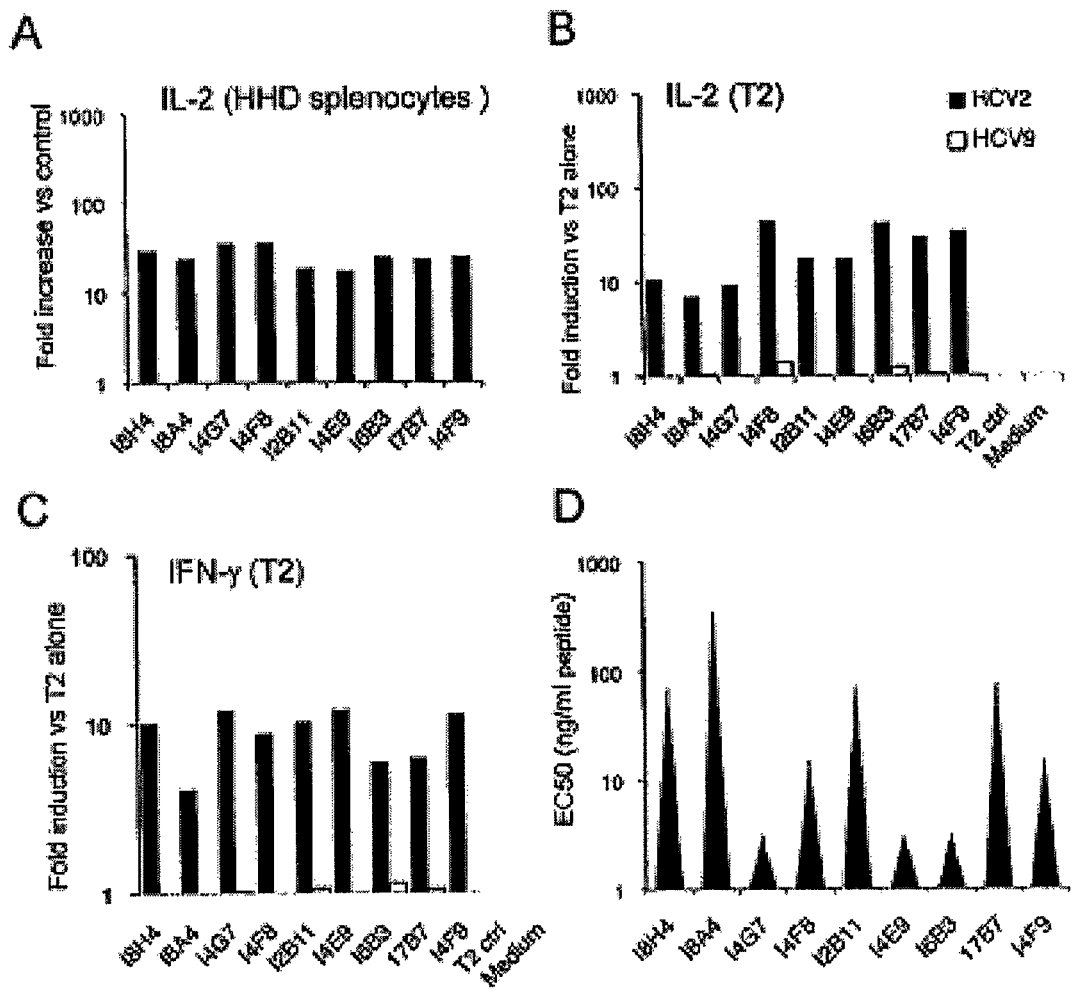
FIG. 1 Hybridoma reactivity is specific against HHD- and HLA-A2 target cells loaded with $NS3_{1073}$. (A) Fold increase in IL-2 secretion upon stimulation with $NS3_{1073}$-loaded HHD target. (B) IL-2 and (C) IFN-γ secretion upon stimulation with T2 cells loaded with $NS3_{1073}$ (□ HCV2) or $NS3_{1406}$ (■ HCV9). Depicted fold induction is given as the ratio of cytokine concentration in co-cultures containing peptide-loaded target (10 μg/ml of indicated peptide) over the control (0 μg/ml of indicated peptide). Average values of duplicate co-cultures from one experiment are shown. Comparative results were obtained in 2-3 separate experiments. (D) EC50 values of $NS3_{1073}$ reactivity for each hybridoma.

Methods of generating a wide variety of murine T cell hybridomas that are specific for a desired epitope are described herein. Preferably, the murine T cell hybridomas are specific for "human antigens," which include epitopes of pathogens that infect humans such as, viral epitopes including, but not limited to, hepatitis viral epitopes such as, hepatitis B virus (HBV) and HCV, as well as, other antigens such as, allergens including, but not limited to, birch allergens. These robust methods facilitate the production and isolation of T cell receptors (TCRs) and nucleic acids encoding said T cell receptors because the approaches described herein avoid having to use primary human T cell cultures. Since murine TCRs are less likely to interfere or mispair with endogenous human TCRs, these methods also generate very specific TCRs that are directed to human antigens with high efficiency.

Aspects of the invention, for example, concern the discovery of several human HCV-specific murine lymphocyte clones, and stable immortalization of these clones via somatic cell hybridization with the BW5147 cell line. Hybrids were selected to the HCV HLA-A2$^+$ restricted NS3$_{1073}$ CTL target, an immunodominant T cell epitope previously reported to coincide with acute HCV and spontaneous resolved HCV infection. See Wertheimer, A. M., C. Miner, D. M. Lewinsohn, A. W. Sasaki, E. Kaufman, and H. R. Rosen, (2003) Novel CD4+ and CD8+ T-cell determinants within the NS3 protein in subjects with spontaneously resolved HCV infection. Hepatology 37:577-89, which is hereby incorporated by reference in its entirety. Although the T cell receptors (TCRs) share the same peptide specificity, certain differences in the functional avidity was observed. The hybridoma I4G7 appeared more active than the others and displayed substantial activity at the lower range of nanomolar peptide density. Moreover, an increased ability to tolerate mutational changes in the target peptide was also seen. The hybridoma I8A4, on the other hand, showed features representing a low functional avidity clone. In addition, it tolerated very little peptide alteration (essentially only 1 out of 9 amino acid residues) and resembled the description of primary human T cell clones reported earlier. See Fytili, P., et al., (2008) Cross-genotype-reactivity of the immunodominant HCV CD8 T-cell epitope NS3-1073, Vaccine 26:3818-26, the contents of which are hereby incorporated by reference in its entirety. On the basis of the present findings, the methods described herein allow for rational selection and preservation of functional T cells with specificity to human MHC restricted antigens, which otherwise would be difficult to grow and maintain indefinitely.

BW T cell hybrids can express CD4 following hybridization with T help lymphocytes, but CD8 expression is retained in CD8+ lymphocyte hybrids. See Rock, K. L., L. Rothstein, and S. Gamble, (1990) Generation of class I MHC-restricted T-T hybridomas. J Immunol 145:804-11, which is hereby incorporated by reference in its entirety. The BW hybrids created by the methods disclosed herein lack CTL function but the effector cytokine secretion provides a sensitive and quantitative measurement of an antigen-dependent T cell activation. Selection of CD8-independent functional T cells is therefore contemplated. Since CD8-independent TCR activation is reported as a hallmark in reported high-affinity TCR, see Chervin, A. S., et al., (2009) The impact of TCR-binding properties and antigen presentation format on T cell responsiveness. J Immunol 183:1166-78, wich is hereby incoporated by reference in its entirety, the methods described herein also bias toward such a selection. Moreover, the hybridoma recognition of NS3$_{1073}$ is cross-reactive between the human HLA and the HHD, which allows further in vivo functional studies of these TCR in the HHD mouse model.

Antigen-specific T lymphocytes are desirable for understanding HCV antigen processing and presentation and the impact on the subsequent T cell priming. Priming and activation of an antigen-specific T cell relies on physical interactions between the T-cell receptor the T lymphocyte and the peptide antigen in the MHC complex of the APC. Unlike primary T cell clones that are maintained through repetitive antigen stimulation and cytokine growth factors, the hybrids generated by the methods described herein grow vigorously in simple serum-containing cell-culture medium without requirement of special supplements. They do not fluctuate their activity in cyclic manner, as occurs with some antigen-stimulated T-cell clones. Freezing and recovery is easy and moreover good viability and activity are observed. Having a spectrum of TCR with varying binding strengths provides several opportunities to study, improve, and treat cell-mediated liver damage of HCV effector T lymphocytes. The data presented herein provides strong evidence that one can effectively establish stable immortalized T cell lines with restriction to human HLA molecules to many different antigens. Additionally, the data provided herein supports the use of genetically engineered TCRs in adoptive T cell therapies so as to engineer CD8-independent TCRs for introduction into new effector CD8+ or CD4$^+$ Th cells.

Several of the embodiments described herein have biotechnological and therapeutic use. For example, the nucleic acids described herein can be incorporated into constructs that allow for expression of the TCR or a fragment thereof (e.g., an alpha and/or beta chain or mutant thereof) in a cell (e.g., a T cell population) so as to allow functional analysis of the TCR and its interaction with HCV or an HCV peptide. The constructs described herein can also be used, for example, to transfect T cells (e.g., isolated from a patient that has HCV) so as to obtain a population of T cells that expresses one or more of the HCV-specific TCRs described herein. The transfected T cells can then be re-introduced to the patient so that the patient can mount an immunological response to HCV.

Accordingly, embodiments of the invention include a purified, enriched, or isolated nucleic acid that encodes one or more of the TCR alpha and/or beta chains described herein (e.g., SEQ. ID. NO: 1, SEQ. ID. NO: 2, SEQ. ID NO: 3, SEQ. ID. NO: 4, SEQ. ID. NO: 5, SEQ. ID. NO. 6, SEQ. ID. NO: 7, SEQ. ID. NO: 8, SEQ. ID. NO. 9, SEQ ID NO: 104, SEQ ID NO: 105, SEQ ID NO: 106, SEQ ID NO: 107, SEQ ID NO: 119 etc.). As used herein, "enriched" means that the concentration of the material is at least about 2, 5, 10, 100, or 1000 times its natural concentration (for example), advantageously 0.01%, by weight, preferably at least about 0.1% by weight. Enriched preparations from about 0.5%, 1%, 5%, 10%, and 20% by weight are also contemplated. The term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. It is also oftentimes advantageous that the sequences be in purified form. The term "purified" does not require absolute purity; rather, it is intended as a relative definition. Isolated proteins have been conventionally purified to electrophoretic homogeneity by Coomassie staining, for example. Purification of starting material or natural material to at least one order of magnitude, preferably two or three orders, and more preferably four or five orders of magnitude is expressly contemplated.

Some embodiments, for example, concern an isolated nucleic acid comprising, consisting essentially of, or consisting of a nucleotide sequence selected from the group consisting of SEQ. ID. NO: 63, SEQ. ID. NO: 64, SEQ. ID NO: 65, SEQ. ID. NO: 66, SEQ. ID. NO: 67, SEQ. ID. NO. 68, SEQ. ID. NO: 69, SEQ. ID. NO: 70, SEQ. ID. NO. 71, SEQ. ID. NO. 74, SEQ. ID. NO. 75, SEQ. ID. NO. 76, SEQ. ID. NO. 77, SEQ. ID. NO. 78, SEQ. ID. NO. 79, SEQ. ID. NO. 83, SEQ. ID. NO. 84, SEQ. ID. NO. 85, SEQ. ID. NO. 86, SEQ. ID. NO. 87, SEQ. ID. NO. 90, SEQ. ID. NO. 90, SEQ. ID. NO. 91, SEQ. ID. NO. 92, SEQ. ID. NO. 93, SEQ. ID. NO. 94, SEQ. ID. NO. 95, SEQ. ID. NO. 98, SEQ. ID. NO. 99, SEQ. ID. NO. 100, SEQ. ID. NO. 101, SEQ. ID. NO. 102, and SEQ. ID. NO. 103. Many other nucleic acids, however, are also embodied. It will be readily appreciated that the redundancy of the genetic code, and the ability to readily introduce natural or synthetic introns into these sequences, to append non-coding sequences including without limitation promoters, spacer nucleic acids, IRESs, polyadenylation sequences, nuclear receptor response elements, viral encapsidation sites, and transposons, as well as many other similar and dissimilar modifications and the amino acids encoded thereby, are contemplated. Moreover, the inventive nucleic acids can encode a pre-protein in which a portion of the protein is removed to yield an polypeptide having an amino acid sequence of the invention (e.g., SEQ ID NOS: 1-9, SEQ ID NO: 104, SEQ ID NO: 105, SEQ ID NO: 106, SEQ ID NO: 107, and SEQ ID NO: 119). Similarly, directed evolution by known methods and routine screening provides analogs and derivatives of the TCRs and the nucleic acids encoding the same by straightforward and predictable methods.

For example, the inventive nucleic acids can be mutated to derive other useful α- and β-chains of T cell receptors capable of recognizing HCV antigens. For example, the nucleic acids of SEQ ID NOS: 63-71, SEQ ID NOS: 74-79, SEQ ID NOS: 82-87, SEQ ID NOS: 90-95, and SEQ ID NOS: 98-103, can be used to generate a library of mutant nucleic acids. One preferred method of generating this library is to clone a portion of one or more nucleic acids of SEQ ID NOS: 63-71, SEQ ID NOS: 74-79, SEQ ID NOS: 82-87, SEQ ID NOS: 90-95, and SEQ ID NOS: 98-103 into a vector and propagating the same in the *E. coli* mutator strain XL1-Red (available from Strategene®, La Jolla, Calif.). A library of yeast cells can be generated by transfecting yeast with the mutagenized nucleic acids of SEQ ID NOS: 63-71, SEQ ID NOS: 74-79, SEQ ID NOS: 82-87, SEQ ID NOS: 90-95, and SEQ ID NOS: 98-103 under suitable conditions such that the yeast display the T cell receptors on their surface. An anti-TCR antibody or other labeling reagent can then be used to identify, such as by flow cytometry, the yeast expressing suitable T cell receptor mutants on their surface. Conventional binding assays measuring the avidity of the mutant T cell receptors for the appropriate peptide/Major Histocompatibility Complexes (MHC) can be used to select desired derivatives of nucleic acids of SEQ ID NOS: 63-71, SEQ ID NOS: 74-79, SEQ ID NOS: 82-87, SEQ ID NOS: 90-95, and SEQ ID NOS: 98-103.

Aspects of the invention also provide nucleic acids mutated in the nucleic acids encoding variants of SEQ ID NOS: 1-9, SEQ ID NO: 104, SEQ ID NO: 105, SEQ ID NO: 106, SEQ ID NO: 107 and SEQ ID NO: 119 in which the CDR3 regions of the these proteins has been mutated by addition, deletion, and/or mutation, but preferably mutation, of one, two, three, three to five, three to ten, five to ten, five to twenty, or ten to twenty amino acids of the CDR3 regions. The variant α- and β-chains produced thereby preferably have the functions of variant TCRs described previously herein. The nucleic acids encoding the α- and β-chains described herein can be further optimized by replacing codons yielding low levels of translation with codons yielding high levels of translation (e.g., codon optimization).

The aforementioned isolated nucleic acid sequences can be operably linked to a nucleic acid sequence encoding a promoter (e.g., a constitutive or inducible promoter) and can be incorporated into a nucleic acid construct (e.g., an expression construct), which may comprise other sequences including nucleic acids encoding a selectable marker (e.g., a neomycin resistance gene), activation sequences (e.g., a site for binding of a transcriptional activator protein), protease cleavage sequences (e.g., viral protease cleavage sequences such as the 2A protease), reporter genes (e.g., green fluorescent protein, luciferase, or chloramphenicol transferase) and/or inducible suicide genes (e.g., herpes simplex virus—thymidine kinase (HSV-TK), which may itself be operably linked to a constitutive promoter, such as, SV40, actin, or CMV). Viral promoters, such as, without limitation, the major late CMV promoter, the RSV promoter, and the promoter found in the long-terminal repeat of the murine stem cell virus are among the preferred promoters, which can be operably linked with one or more of the nucleic acids described herein. Additional suitable genetic elements known in the art can also be ligated to, attached to, or inserted into the nucleic acid and constructs described herein to provide additional functions, level of expression, or pattern of expression.

A variety of host-expression vector systems can be utilized to express the nucleic acids and constructs described herein. Suitable vectors include without limitation viral vectors. Suitable viral vectors include without limitation retroviral vectors, lentiviral vectors, alphaviral, vaccinia, adenoviral, adenoassociated viral, herpes viral, and fowl pox viral vectors, and preferably have a native or engineered capacity to transfect T cells. Additionally, the vectors useful in the context of the invention can be "naked" nucleic acid vectors (i.e., vectors having little or no proteins, sugars, and/or lipids encapsulating them), or complexed with other molecules. Preferred expression systems include the pLPCX vector from Clonetech® and the TCRalpha chain-2A autocleavaging protease-TCRBeta chain system.

The expression systems encompass, however, engineered host cells that express the peptides described herein and purification or enrichment of the peptides from such expression systems can be accomplished using appropriate detergents and lipid micelles and methods well known to those skilled in the art. However, such engineered host cells themselves can be used in situations where it is important not only to retain the structural and functional characteristics of the peptides but to assess biological activity, e.g., in screening assays.

The expression systems that can be used include, but are not limited to, microorganisms such as bacteria (e.g., *E. coli* or *B. subtilis*) transformed with recombinant bacteriophage DNA, plasmid DNA or cosmid DNA expression vectors containing nucleotide sequences described herein; yeast (e.g., *Saccharomyces, Pichia*) transformed with recombinant yeast expression vectors containing the nucleotide sequences; insect cell systems infected with recombinant virus expression vectors (e.g., baculovirus) containing the nucleotide sequences; or mammalian cell systems (e.g., COS, CHO, BHK, 293, 3T3, CIR-A2, and BW TRC-) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the gene product being expressed. For example, when a large quantity of such a protein is to be produced, for raising antibodies to a TCR, for example, vectors which direct the expression of high levels of fusion protein products that are readily purified can be desirable. Such vectors include, but are not limited, to the *E. coli* expression vector pUR278 (Ruther et al., *EMBO J.*, 2:1791 (1983), in which the TCR coding sequence can be ligated individually into the vector in frame with the lacZ coding region so that a fusion protein is produced; pIN vectors (Inouye & Inouye, *Nucleic Acids Res.*, 13:3101-3109 (1985); Van Heeke & Schuster, *J. Biol. Chem.*, 264:5503-5509 (1989)); and the like. pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The TCR gene coding sequence can be cloned individually into non-essential regions (for example the polyhedrin gene) of the virus and placed under control of an AcNPV promoter (for example the polyhedrin promoter). Successful insertion of TCR gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al., *J. Virol.* 46: 584 (1983); and Smith, U.S. Pat. No. 4,215,051).

In mammalian host cells, a number of viral-based expression systems can be utilized. In cases where an adenovirus is used as an expression vector, the TCR nucleotide sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the gene product in infected hosts. Specific initiation signals can also be required for efficient translation of inserted TCR nucleotide sequences. These signals include the ATG initiation codon and adjacent sequences. In cases where an entire TCR gene or cDNA, including its own initiation codon and adjacent sequences, is inserted into the appropriate expression vector, no additional translational control signals are needed.

Preferred vectors comprise a portion of the murine stem cell virus LTR or a known analog thereof. Vectors further comprising the gag region and env splice site, can be obtained from the vector SFGtcLuc+ITE4−. In some embodiments, the vector contains a single chain TCR encoding both α-chain and β-chain specific sequences in a single polypeptide. When the vector comprises a single chain TCR, it can, but preferably does not contain other TCR-related polypeptides. It is convenient, however, to incorporate nucleic acids encoding portions of the α-chain and β-chain of a single TCR (or variant thereof) into a single vector, in which event each of the two nucleic acids independently can be in any of the six reading frames, and positioned proximally or distally to each other. When the two nucleic acids are placed proximal to each other in a vector it is often-convenient to drive the expression of both nucleic acids from a single promoter and to include an internal ribosome binding site (IRES) 5' of the second nucleic acid. Alternatively, a second promoter, such as a phosphoglycerol kinase (PGK) promoter can be used to drive the expression of the second nucleic acid construct. In some embodiments, a proteolytic cleavage site (e.g., the 2A protease cleavage site from Thosea asigna virus, an insect virus) is engineered between the alpha and beta chain specific sequences (e.g., a viral protein cleavage site). It should be understood that other protease domains including other 2A protease domains obtained form other virus can be used. Preferably, the pLPCX vector from Clonetech® and the TCRalpha chain-2A autocleavaging protease-TCRBeta chain system is used. In another embodiment, a "single-chain" TCR construct in which portions of SEQ ID NOS: 1-9, SEQ ID NO: 104, SEQ ID NO: 105, SEQ ID NO: 106, SEQ ID NO: 107, and SEQ ID NO: 119, can be encoded by a nucleic acid encoding a single polypeptide. However, in cases where only a portion of the TCR coding sequence is inserted, exogenous translational control signals, including, perhaps, the ATG initiation codon, should be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc.

The nucleic acids and vectors can be transduced into cells either in vitro or in vivo. Suitable approaches include without limitation electroporation, transformation, transduction, conjugation or triparental mating, cotransfection, coinfection, membrane fusion (especially with cationic lipids), liposomecell fusion, high velocity bombardment with nucleic acid-coated or vector-coated microprojectiles, incubation with calcium phosphate-DNA precipitate, direct microinjection into single cells, and the like. Accordingly, other molecules that can be suitably combined with the nucleic acids described herein include without limitation viral coats, cationic lipids, liposomes, and targeting moieties such as ligands or receptors for target cell surface molecules.

In addition, a host cell strain can be chosen, which modulates the expression of the inserted sequences, or modifies and processes the gene product in the specific fashion desired. Such modifications (e.g., glycosylation) and processing (e.g., cleavage) of protein products are important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, and WI38.

For long-term, high-yield production of recombinant proteins, stable expression is preferred. For example, cell lines that stably express the TCR sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines, which express the TCR gene product.

A number of selection systems can be used, including but not limited to the herpes simplex virus thymidine kinase (HSV-TK) (Wigler, et al., *Cell* 11:223 (1977), hypoxanthine-guanine phosphoribosyltransferase (Szybalska & Szybalski, *Proc. Natl. Acad. Sci. USA* 48:2026 (1962), and adenine phosphoribosyltransferase (Lowy, et al., *Cell* 22:817 (1980) genes can be employed in tk-, hgprt- or aprt-cells, respectively. Also, antimetabolite resistance can be used as the basis of selection for the following genes: dhfr, which confers resistance to methotrexate (Wigler, et al., *Proc. Natl. Acad. Sci. USA* 77:3567 (1980); O'Hare, et al., *Proc. Natl. Acad. Sci. USA* 78:1527 (1981); gpt, which confers resistance to mycophenolic acid (Mulligan & Berg, Proc. *Natl. Acad. Sci. USA* 78:2072 (1981); neo, which confers resistance to the aminoglycoside G-418 (Colberre-Garapin, et al., *J. Mol. Biol.* 150:1 (1981); and hygro, which confers resistance to hygromycin (Santerre, et al., *Gene* 30:147 (1984)).

Alternatively, any fusion protein can be readily purified by utilizing an antibody specific for the fusion protein being expressed. For example, a system described by Janknecht et al. allows for the ready purification of non-denatured fusion proteins expressed in human cell lines. (Janknecht, et al., *Proc. Natl. Acad. Sci. USA* 88: 8972-8976 (1991)). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitrilo-acetic acid-agarose columns and histidine-tagged proteins are selectively eluted with imidazole-containing buffers.

Other embodiments include purified or isolated polypeptides that comprise, consist, or consist essentially of SEQ. ID. NO: 1, SEQ. ID. NO: 2, SEQ. ID NO: 3, SEQ. ID. NO: 4, SEQ. ID. NO: 5, SEQ. ID. NO. 6, SEQ. ID. NO: 7, SEQ. ID. NO: 8, SEQ. ID. NO. 9, SEQ ID NO: 104, SEQ ID NO: 105, SEQ ID NO: 106, SEQ ID NO: 107 and SEQ ID NO: 119. Any one of these sequences can be readily varied or altered without substantially diminishing (or altering) the ability of the encoded polypeptide to form part of a TCR that recognizes HCV antigens in the context of an MHC. For example, conservative and non-conservative variations can be made in complimentarity determining and non-complimentarity determining regions of the amino acid sequence of the TCR chain that do not affect function. Changes in the region of the CDR3, or within CDR3 are preferred.

The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis.

Similarly, it is known in the art that spacer amino acid sequences that add 1, 2, 3, about 5, about 10, 11-20, 21-35, and more amino acids to SEQ ID NOS: 1-9 SEQ ID NO: 104, SEQ ID NO: 105, SEQ ID NO: 106, SEQ ID NO: 107 and SEQ ID NO: 119, and deletions that remove 1, 2, 3, up to about 5, up to about 10, between 11 and 20, amino acids from SEQ ID NOS: 1-9 SEQ ID NO: 104, SEQ ID NO: 105, SEQ ID NO: 106, SEQ ID NO: 107 and SEQ ID NO: 119, can be made without destroying the essential characteristics of these polypeptides, which are to recognize HCV antigens in the context of an MHC with high avidity. The ordinarily skilled artisan can readily and routinely screen variant amino acids and/or the nucleic acids encoding them to determine if these variations substantially lessen or destroy the functionality of these sequences. Accordingly, the term "consisting essentially of" can be used to encompass, for example conservative alterations or the inclusion of spacer sequences that do not substantially impact the function, e.g., ability to bind NS3 or NS5 peptides.

The amino acid sequences that vary from SEQ ID NOS: 1-9 SEQ ID NO: 104, SEQ ID NO: 105, SEQ ID NO: 106, SEQ ID NO: 107 and SEQ ID NO: 119 provided herein preferably have at least 60% sequence identity, more preferably at least 85% sequence identity, even more preferably at least 92% sequence identity, and optionally at least 96% sequence identity to SEQ ID NOS: 1-9 SEQ ID NO: 104, SEQ ID NO: 105, SEQ ID NO: 106, SEQ ID NO: 107 and SEQ ID NO: 119. That is, embodiments can have at least, equal to or any number between about 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% homology or sequence identity to SEQ ID NOS: 1-9 SEQ ID NO: 104, SEQ ID NO: 105, SEQ ID NO: 106, SEQ ID NO: 107 and SEQ ID NO: 119.

Several homology or sequence identity searching programs based on nucleic acid sequences are known in the art and can be used to identify molecules that are homologous. In one approach, a percent sequence identity can be determined by standard methods that are commonly used to compare the similarity and position of the base pairs of two nucleic acids. Using a computer program such as BLAST or FASTA, two sequences can be aligned for optimal matching of their respective base pairs (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program.

Also provided are amino acid sequences, and nucleic acid sequences encoding the same in which, the hypervariable or complementarity determining regions or both of SEQ ID NOS: 1-9 SEQ ID NO: 104, SEQ ID NO: 105, SEQ ID NO: 106, SEQ ID NO: 107 and SEQ ID NO: 119 are engineered into other TCR genes such that the obtained amino acid sequence has 100% identity with one of SEQ ID NOS: 1-9 SEQ ID NO: 104, SEQ ID NO: 105, SEQ ID NO: 106, SEQ ID NO: 107 and SEQ ID NO: 119 for at least 8, at least 10, at least 12, at least 15, at least 18, at least 20, at least 21, at least 22, at least 23, at least 24, at least 25 consecutive amino acids, in at least one region (e.g, one, two, three, or at least three) of the obtained amino acid sequence, and when expressed in normal T cells (which prior to expression of the obtained amino acid sequence; do not recognize HCV) allow the T cell to attack HCV or HCV infected cells. As described above, these peptides can further include additional peptide sequences including a peptide encoded by the neomycin resistance gene, protease cleavage sequences, and/or the HSV-TK gene. Thus, some embodiments include amino acids that include more than one (e.g., two, three, four, or more) of the amino acid sequences disclosed herein, as well as nucleic acids encoding these amino acids.

Isolated cells or virus containing the aforementioned nucleic acids and polypeptides are also embodiments. For example, bacteria, virus, spleencocytes, hybridomas, packaging cells, or T cells that contain one or more of the aforementioned nucleic acids or peptides are embodiments (e.g., SEQ. ID. NO: 1, SEQ. ID. NO: 2, SEQ. ID NO: 3, SEQ. ID. NO: 4, SEQ. ID. NO: 5, SEQ. ID. NO. 6, SEQ. ID. NO: 7, SEQ. ID. NO: 8, SEQ. ID. NO. 9, SEQ ID NO: 104, SEQ ID NO: 105, SEQ ID NO: 106, SEQ ID NO: 107, SEQ ID NO: 119 or nucleic acids encoding the aforementioned peptides, e.g., SEQ ID NOS: 63-71).

Following synthesis or expression and isolation or purification of a TCR or a fragment thereof (e.g., alpha or beta chain), the isolated or purified peptide can be used to generate antibodies and tools for identifying agents that interact with the TCR. Depending on the context, the term "antibodies" can encompass polyclonal, monoclonal, chimeric, single chain, Fab fragments and fragments produced by a Fab expression library. Antibodies that recognize a TCR described herein and fragments thereof have many uses including, but not limited to, biotechnological applications, therapeutic/prophylactic applications, and diagnostic applications.

For the production of antibodies, various hosts including goats, rabbits, rats, mice, etc. can be immunized by injection with a TCR or any portion, fragment or oligopeptide that retains immunogenic properties. Depending on the host species, various adjuvants can be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol, BCG (*Bacillus Calmette-Guerin*) and *Corynebacterium parvum* are also potentially useful adjuvants.

Peptides used to induce specific antibodies can have an amino acid sequence consisting of at least three amino acids, and preferably at least 10 to 15 amino acids. Preferably, short stretches of amino acids encoding fragments of a desired TCR sequence (e.g., an alpha or beta chain) are fused with those of another protein such as keyhole limpet hemocyanin such that an antibody is produced against the chimeric molecule. While antibodies capable of specifically recognizing a TCR or portion thereof can be generated by injecting synthetic 3-mer, 10-mer, and 15-mer peptides that correspond to a protein sequence of a desired TCR chain into mice, a more diverse set of antibodies can be generated by using recombinant TCR peptides.

To generate antibodies to a desired TCR and fragments thereof, substantially pure peptides (e.g., alpha and/or beta chains) are isolated from a transfected or transformed cell. The concentration of the polypeptide in the final preparation is adjusted, for example, by concentration on an Amicon filter device, to the level of a few micrograms/ml. Monoclonal or polyclonal antibody to the polypeptide of interest can then be prepared as follows:

Monoclonal antibodies can be prepared using any technique that provides for the production of antibody molecules by continuous cell lines in culture. These include, but are not limited to, the hybridoma technique originally described by Koehler and Milstein (*Nature* 256:495-497 (1975), the human B-cell hybridoma technique (Kosbor et al. *Immunol Today* 4:72 (1983); Cote et al *Proc Natl Acad Sci* 80:2026-2030 (1983), and the EBV-hybridoma technique Cole et al. *Monoclonal Antibodies and Cancer Therapy*, Alan R. Liss Inc, New York N.Y., pp 77-96 (1985). In addition, techniques developed for the production of "chimeric antibodies", the splicing of mouse antibody genes to human antibody genes to obtain a molecule with appropriate antigen specificity and biological activity can be used. (Morrison et al. *Proc Natl Acad Sci* 81:6851-6855 (1984); Neuberger et al. Nature 312: 604-608(1984); Takeda et al. *Nature* 314:452-454(1985). Alternatively, techniques described for the production of single chain antibodies (U.S. Pat. No. 4,946,778) can be adapted to produce specific single chain antibodies. Antibodies can also be produced by inducing in vivo production in the lymphocyte population or by screening recombinant immunoglobulin libraries or panels of highly specific binding reagents as disclosed in Orlandi et al., *Proc Natl Acad Sci* 86: 3833-3837 (1989), and Winter G. and Milstein C; *Nature* 349:293-299 (1991).

Antibody fragments that contain specific binding sites for a TCR or portion thereof can also be generated. For example, such fragments include, but are not limited to, the $F(ab')_2$ fragments that can be produced by pepsin digestion of the antibody molecule and the Fab fragments that can be generated by reducing the disulfide bridges of the $F(ab=)_2$ fragments. Alternatively, Fab expression libraries can be constructed to allow rapid and easy identification of monoclonal Fab fragments with the desired specificity. (Huse W. D. et al. *Science* 256:1275-1281 (1989)).

By one approach, monoclonal antibodies to a TCR or fragments thereof are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, New York. Section 21-2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and can require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples; they are also used semi-quantitatively or qualitatively.

Methods of making TCRs are also embodiments. That is, robust approaches to generate TCRs have been discovered, which, in some embodiments, can be used to selectively enhance or favor production of CD8-independent TCRs. By some approaches, these methods are performed by immunizing human HLA (HHD) transgenic mice with a DNA construct encoding a peptide to which a specific TCR is desired ("candidate peptide"). Preferably, the DNA immunization is performed in conjunction with electroporation and may include one or more adjuvants. Spleencocytes are removed from the immunized transgenic mice and screened for cytolytic T lymphocytes (CTL) that are specific for the candidate peptide. The identification of CTL specific for the candidate peptide can be performed by contacting the CTLs with peptide and/or cells loaded with the peptide and measuring the production of interferon-gamma, or chromium$^{51}$ release, or the production of other immune response molecules. T cells expressing at least 1000 pg/ml of interferon gamma, for example, when exposed to low levels of candidate peptide and/or a cell loaded with the peptide are deemed to participate in immunologically relevant cytokine signaling. Once populations of CTLs that are specific for the candidate peptide are identified, they are fused with a tumor cell line to obtain an immortalized hybridoma (e.g., TCR$^-$BW cells). The immortalized hybridomas now produce copius amounts of RNA that encode TCRs that are specific for the candidate peptide. RNA from the hybridomas can be isolated and cDNAs can be generated therefrom using conventional techniques (e.g., reverse transcriptase polymerase chain reaction (RTPCR)). The cDNA can then be sequenced and can be cloned into a construct (e.g., an expression construct). That is, the resulting expression cassette harboring the genes encoding TCR alpha chain, a 2A protease motif, and TCR beta chain are assembled and cloned into a mammalian expression vector, preferably, the pLPCX vector from Clonetech® (e.g., the pLPCX vector from Clonetech® and the TCRalpha chain-2A autocleavaging protease-TCRBeta chain system can be used).

In some embodiments, the DNA encoding the alpha and beta TCR chains in the expression constructs are separated by a protease cleavage site (e.g., a viral protease cleavage site such as the 2A protease) so as to facilitate assembly of the TCR by a T cell. The construct can also comprise a suicide gene such as an HSV-TK gene, which is driven by a strong constitutive promoter (e.g., SV40, actin, or CMV). In some embodiments, a separate construct that comprises the HSV-TK gene driven by a strong promoter (e.g., SV40 or CMV) is used. The constructs may also be incorporated into packaging cells so as to generate a retroviral vector and the vector can be used to infect T cells (preferably T cells isolated from a patient in need of a TCR specific for the candidate peptide).

Accordingly, aspects of the invention also concern methods of treatment, inhibition of infectivity, or prophylaxis of a disease, such as, HCV. By some approaches, a TCR specific for an HCV peptide (e.g., an NS3 peptide such as, 1073-1081, or an NS5 peptide such as, 1992-2000) is generated by providing a DNA construct encoding said peptide and immunizing human HLA (HHD) transgenic mice with said DNA, preferably in the presence of an adjuvant and/or electroporation. Spleenocytes are obtained from said immunized mice and CTLs specific for the HCV peptide (e.g., an NS3 peptide such as 1073-1081 or NS5 peptide such as 1992-2000) are identified (e.g., by measuring production of an immune response molecule such as, interferon gamma or chromium$^{51}$ release in the presence of the peptide and/or cells loaded with the peptide). CTLs specific for the HCV peptide (e.g., an NS3 peptide such as, 1073-1081, or NS5 peptide such as, 1992-2000) are then fused to a tumor cell line (e.g., TCR$^-$ BW cells) to obtain immortalized hybridomas. Reverse transcriptase polymerase chain reaction (RT-PCR) is then performed (e.g., using oligonucleotides disclosed herein). The individual PCR products are inserted into an expression construct (e.g., pCR2.1 vector or a commercially available vector from Invitrogen® or Orbigen Inc.). The resulting expression cassette harboring the genes encoding TCR alpha chain, a 2A protease motif, and TCR beta chain are assembled and cloned into a mammalian expression vector, preferably, the pLPCX vector from Clonetech®. That is, preferably, the pLPCX vector from Clonetech® and the TCRalpha chain-2A autocleavaging protease-TCRBeta chain system is used. Optionally, the construct contains an HSV-TK gene driven by a promoter (e.g., a constitutive promoter such as, SV40 or CMV). The construct comprising the DNA that encodes the HCV-specific TCR and, optionally, the HSV-TK gene is then transfected into a packaging cell line so as to obtain retroviral vectors (e.g., a commercially available packaging cell line or PG13 gibbon ape leukemia virus-packaging cells and the human ecotropic packaging cell line, Phoenix Eco). After co-culture, the packaging cells (e.g., Phoenix Eco cells) are removed from the culture (e.g., by negative selection with magnetic beads conjugated with anti-LYT-2 antibodies). The clones are expanded and high titer clones are selected by dot-blot titration. Southern blotting can be performed to confirm vector integration and copy number.

T cells from a patient in need of an agent that inhibits HCV proliferation are then obtained. Peripheral blood lymphocytes (PBL) are collected by leukophoresis, and lymphocytes are separated by centrifugation on a Ficoll/Hypaque cushion, washed in buffer, then resuspended at a concentration of approximately $1 \times 10^6$/ml in medium, preferably serum-free. The lymphocytes are stimulated with a growth factor (e.g., IL-2, and/or CD3). The lymphocytes are cultured in vitro for 10, 24, 36, or 48 hours before transduction. Following stimulation, lymphocytes are transduced with the retroviral vectors by transfer to culture dishes that are precoated with retroviral vectors. To coat culture plates with the vectors, nontissue culture-treated six-well plates are first treated with recombinant fibronectin fragment (RetroNectin®, Takara, Otsu, Japan). To these plates retroviral vector supernatant is added, the procedure may be repeated the following day, after which time cells may be expanded in an incubator and split as necessary to maintain cell density between approximately $0.5 \times 10^6$ cells/ml and $4 \times 10^6$ cells/ml. The reactivity of the transfected T cells is then, preferably, measured by analyzing the production of an immune response molecule (e.g., interferon gamma) or chromium$^{51}$ release in the presence of the HCV peptide and/or a cell loaded with the peptide. The transfected T cells can then be purified from the culture medium, suspended in a pharmaceutically acceptable buffer or excipient and administered to the subject (e.g., intravenously). Any suitable number of transduced T cells can be administered to a mammal. While a single T cell is capable of expanding and providing a benefit, it is preferable to administer at least $10^3$, more preferably at least $10^5$, even more preferably at least $10^8$ and optionally $10^{12}$ or more transduced T cells. One preferred embodiment comprises administration of from about $10^8$ to about $10^{12}$ transduced T cells to a human. In some embodiments, the inoculated subject is preferably also provided IL-2, and more preferably a high-dose of IL-2. Without desiring to be bound by any particular theory it is believed that the high-dose of IL-2 encourages proliferation of the modified T cells. Optionally, the amount of inhibition of proliferation of HCV is measured after treatment and/or at different times after treatment. Such measurements can be made virologically (e.g., by detecting the level of HCV RNA in the blood of the patient).

The nucleic acids, peptides, and T cells described herein can be employed in admixture with conventional excipients, i.e., pharmaceutically acceptable organic or inorganic carrier substances suitable for parenteral, enteral (e.g., oral) or topical application that do not deleteriously react with the pharmacologically active ingredients. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable vehicles are described in *Remmington's Pharmaceutical Sciences*, 15th Edition, Easton:Mack Publishing Company, pages 1405-1412 and 1461-1487(1975) and The National *Formulary* XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the actives.

The effective dose and method of administration of a particular pharmaceutical formulation having nucleic acids, peptides, and T cells described herein can vary based on the individual needs of the patient and the treatment or preventative measure sought. Therapeutic efficacy and toxicity of such compounds can be determined by standard pharmaceutical procedures in cell cultures or experimental animals, e.g., ED50 (the dose therapeutically effective in 50% of the population). The dosage of such active ingredients lies preferably within a range of circulating concentrations that include the ED50 with no toxicity. The dosage varies within this range depending upon type of nucleic acids, peptides, and T cells described herein, the dosage form employed, sensitivity of the organism, and the route of administration.

Normal dosage amounts of nucleic acids, peptides, and T cells described herein can vary from approximately 1 to 100,000 micrograms, up to a total dose of about 10 grams, depending upon the route of administration. Desirable dosages include 250 µg, 500 µg, 1 mg, 50 mg, 100 mg, 150 mg, 200 mg, 250 mg, 300 µg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g. When T cells are administered, any suitable number of transduced T cells can be provided including but not limited to a single T cell is capable of expanding and providing a benefit but preferably at least, equal to, or greater than $10^3$, $10^5$, $10^8$ or $10^{12}$ transduced T cells. Preferably, from about $10^8$ to about $10^{12}$ transduced T cells are provided to a human. The exact dosage is chosen by the individual physician in view of the patient to be treated. Dosage and administration are adjusted to provide sufficient levels of the active moiety or to maintain the desired effect. Additional factors that can be taken into account include the severity of the disease, age of the organism, and weight or size of the organism; diet, time and frequency of administration, drug combination(s), reaction sensitivities, and tolerance/response to therapy.

Routes of administration of the active ingredients described herein include, but are not limited to, topical, transdermal, parenteral, gastrointestinal, transbronchial, and transalveolar. Transdermal administration is accomplished by application of a cream, rinse, gel, etc. capable of allowing the pharmacologically active compounds to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the pharmacologically actives described herein that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference.

Compositions having the pharmacologically actives described herein that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having the pharmacologically actives described herein that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the pharmacologically actives described herein.

Compositions having the pharmacologically actives described herein that are suitable for gastrointestinal administration include, but not limited to, pharmaceutically acceptable powders, pills or liquids for ingestion and suppositories for rectal administration.

Example 1

This Example describes some of the materials and methods used in the experiments discussed herein in greater detail.

Animals

Inbred HHD-C57/BL6 (HHD$^+$ H-2D$^{b-/-}$ β2m$^{-/-}$) mice transgenic for HLA-A2.1 monochain histocompatibility class I molecule, and deficient for both H-2D$^b$ and murine β2-microglobulin (β2m) were kindly provided by Dr F Lemonnier, Institut Pasteur, France (35). HHD-C57/BL6 mice were bred and maintained in-house (Karolinska Institutet, Karolinska University Hospital Huddinge, Stockholm, Sweden). The ethical committee for animal research at Karolinska Institutet had approved all animal experiments.

Plasmids and Synthetic Peptides

The DNA plasmid (pVax1-NS3/4A) containing the full-length codon optimized (co) NS3/4A gene in pVAX1 have been described previously. See Frelin, L. et al. (2004), Codon optimization and mRNA amplification effectively enhances the immunogenicity of the hepatitis C virus nonstructural 3/4A gene, Gene Ther 11:522-33. which is hereby incorporated by reference in its entirety. Plasmid DNA was grown and purified as described. See Frelin, L., et al., (2003) Low dose and gene gun immunization with a hepatitis C virus nonstructural (NS) 3 DNA-based vaccine containing NS4A inhibit NS3/4A-expressing tumors in vivo, Gene Ther 10:686-99, which is hereby incorporated by reference in its entirety. The purified plasmid DNA was dissolved and diluted in sterile phosphate-buffered saline (PBS) to a concentration of 1 mg/ml. Peptides were produced corresponding to HLA-A2 epitopes of the NS3 region of HCV. The following HCV NS3 peptides were used: (CVNGVCWTV (SEQ. ID. NO.: 20) [aa 1073 to 1081]), and KLVALGVNAV (SEQ. ID. NO.: 21) [aa 1406 to 1415]), respectively, referred to as NS3 1073-1081, and NS3 1406-1415. Each aa in the NS3 1073-1081 epitope was sequentially replaced by alanine (Ala), generating the following peptides: AINGVCWTV$^{1073\text{-}Ala}$ (SEQ. ID. NO.: 22), CANGVCWTV$^{1074\text{-}Ala}$ (SEQ. ID. NO.: 23), CIAGVCWTV$^{1075\text{-}Ala}$ (SEQ. ID. NO.: 24), CINAVCWTV$^{1076\text{-}Ala}$ (SEQ. ID. NO.: 25), CINGACWTV$^{1077\text{-}Ala}$ (SEQ. ID. NO.: 26), CINGVAWTV$^{1078\text{-}Ala}$ (SEQ. ID. NO.: 27), CINGVCATV$^{1079\text{-}Ala}$ (SEQ. ID. NO.: 28), CINGVCWAV$^{1080\text{-}Ala}$ (SEQ. ID. NO.: 29), and CINGVCWTA$^{1081\text{-}Ala}$ (SEQ. ID. NO.: 30). The peptides were synthesized using an automated peptide synthesizer as described previously. See Sallberg, M et al., (1991) Rapid "tea-bag" peptide synthesis using 9-fluorenylmethoxycarbonyl (Fmoc) protected amino acids applied for antigenic mapping of viral proteins. Immunol Lett 30:59-68, which is hereby incorporated by reference in its entirety.

Immunization Protocol

DNA immunizations were performed by regular intramuscular (i.m.) immunization in the tibialis anterior (TA) muscle (50 μg/dose). Immediately after the injection, in vivo electroporation was applied. The immunization procedure was done exactly as described previously. See Ahlen, G., et al. (2007) In vivo electroporation enhances the immunogenicity of hepatitis C virus nonstructural 3/4A DNA by increased local DNA uptake, protein expression, inflammation, and infiltration of CD3+ T cells, J Immunol 179:4741-53, which is hereby incorporated by reference in its entirety. The procedure was repeated up to three times at monthly intervals.

Cell Lines

BW5147 alpha-beta-cell line (BW TCR$^-$ cells) kindly provided Dr. Kappler and Dr. Marrack at National Jewish Medical and Research Center, were grown in DMEM 10% FBS supplemented with 1 mM non essential amino acids, 2 mM L-glutamine, 44.84 mg/L Gentamicin, 2 μM 2-mercaptoethanol, 100 U/ml penicillin, and 100 μg/ml streptomycin (referred to as complete BW TCR$^-$ medium). T2, C1R-A2 and C1R-null cells (kindly provided by Dr. M Maeurer, Swedish Institute for Infectious Disease, Stockholm, Sweden) were grown in RPMI 10% FBS supplemented with 2 mM L-glutamine, 100 mM HEPES, 100 U/ml penicillin, and 100 μg/ml streptomycin. T2 is a HLA A2.1+ cell line, a cloned hybrid between the 721.174 (variant of the LCL 721 B lymphoblastic cell line) and CEMR.3 (8-azaguanine and ouabain resistant clone of the CEM T lymphoblastic cell line). C1R-A2 is an EBV-transformed B-lymphocyte cell line expressing the HLA-A2 molecule. C1R-null is HLA-A2-negative. Endogenous peptides on HLA-A2 molecules expressed as a transgene on C1R-A2 cells were removed by mild acid treatment (pH 3.3) and HCV NS3-specific HLA-A2 peptides were used to reconstitute the HLA-A2 molecules as shown previously. See Nilges, K et al. (2003) Human papillomavirus type 16 E7 peptide-directed CD8+ T cells from patients with cervical cancer are cross-reactive with the coronavirus NS2 protein. J Virol 77:5464-74, which is hereby incorporated by reference in its entirety. RMAS-HHD (HHD$^+$ H-2$^{b-}$; kindly provided by Dr F Lemonnier, Institut Pasteur, France) were maintained in RPMI 1640 medium supplemented with 5% FBS, 2 mM L-glutamine, 100 U/ml penicillin, 100 μg/ml streptomycin and 800 μg/ml Geneticin (G418). All cells were grown in a humidified incubator at +37° C. and with 5% CO$_2$. All medium and supplements were purchased from Invitrogen®, Carlsbad, Calif., USA.

Fusion and Selection and T Cell Hybridomas

Spleencocytes and lymph node cells from HHD-C57BL/6 coNS3/4A-DNA immunized mice were harvested two weeks after the last immunization and stimulated in vitro for 4-5 days in the presence of 10 μg/ml of the different HCV NS3/4A HLA-A2 peptides. After stimulation, CD8+ T cells were isolated using a commercially available CD8 T cell isolation kit and fused with BW TRC$^-$ cells as fusion partner. In brief, directly after bead purification, the CD8+ cells were mixed together with the BW TRC$^-$ cells in a 1:5 ratio (e.g BW TRC$^-$ cells never exceeded 10$^7$ cells per tube). The cells were washed twice in PBS. PEG1450 was subsequently added to the dry cell pellet. Thereafter, 50 ml MEM were slowly added and the cells were incubated for 5 min at 37° C. After incubation, the cells were washed in PBS, re-suspended in complete BW TRC⁻ medium, and counted. Fused cells were seeded at a concentration of 1 to 5 cells/well in U-bottom 96-well plates and grown for two days in complete BW TRC⁻ medium. Thereafter the cells were grown in complete BW TRC⁻ medium supplemented with 3X Hypoxanthine Aminopterin Thymidine (HAT) for 15 days to select for fused hybridomas. Lastly, the hybridomas were grown in BW TRC⁻ medium supplemented with 1× Hypoxanthine Thymidine (HT) for another 15 days. After the selection procedure, established hybridoma cell lines were cultured in complete BW TRC⁻ medium.

Flow Cytometry

Hybridoma clones were screened for CD3-expression with an FITC-CD3 antibody. CD3+ monoclonal hybridomas were subsequently screened for CD8-expression using a FITC-CD8 antibody and pentamer binding using the R-PE labeled HLA-A2 (CINGVCWTV (SEQ. ID. NO.: 10)) pentamer and the HBV core pentamer was used as negative control. Surface expression of HLA-A2 was analyzed on all cells used (T2, C1R-A2, C1R-null, RMAS-HHD) using a FITC-HLA-A2 antibody. For pentamer staining, $1\times10^6$ cells were incubated for 15 min at room temperature in the dark with 10 µl of pentamer in a total volume of 50 µl. Thereafter, the cells were washed in washing buffer and fixed in 2% PFA in PBS. Approximately 25000 total events from each sample were acquired on a FACSCalibur flow cytometer and were evaluated using commercially available software.

Functional Analysis on Peptide-Loaded Targets

CD3+ monoclonal hybridomas were screened for interleukin-2 (IL-2) and interferon-γ (IFN-γ) production after 22 hrs of co-culture with T2 cells loaded with the indicated peptides. In a V-bottom 96-wells plate, $2\times10^5$ hybridoma cells and the same amount of T2 cells were co-cultured in 200 µl of complete BW TCR⁻ medium. 100 µl of each supernatant were tested in an enzyme-linked immunosorbant assay (ELISA) specific for mouse IL-2 and mouse IFN-γ (Mabtech, Nacka Strand, Sweden). The hybridoma clones tested positive were re-tested on target cells loaded with CINGVCWTV (SEQ. ID. NO.: 10) [1073-1081] peptide, and were regularly checked by FACS for CD3 expression. A peptide titration assay using the $NS3_{1073-1081}$ peptide and its alanine substitution analogues were conducted by co-culturing T2 cells loaded with serial dilutions of each peptide together with the indicated hybridoma clones.

Functional Analysis on Targets Expressing Endogenous Processed NS3 Peptide

The pVax1-NS3/4A transiently transfected C1R-A2 cells were used as targets in an 24 hour co-culture with $2\times10^5$ hybridoma cells. Cells transfected with the pEGFP plasmid was used was control. Bulk transfection was carried out using the Lipofectamine 2000 (Invitrogen®) the day before the assay and equal amount of transfected cells were co-cultured with hybridoma cells. The culture supernatants were harvested 24 hours after co-incubation for IL-2 analysis.

TCR Gene Typing and Sequencing

Total RNA was extracted from $10\times10^6$ cells from each hybridoma clone using 750 µl Trizol (Invitrogen®). cDNA was generated from 5 µg of total RNA using Superscipt® III RT enzyme 200 U/µl (Invitrogen®) and 50 µM oligo $dT_{(12-18)}$ primers according to Superscipt® III manual from Invitrogen®. The reaction was incubated for 60 minutes at 37° C. and subsequently inactivated by heating at 70° C. for 15 minutes. T cell receptor (TCR) variable alpha (VA) and beta (VB) chain usage was determined using a PCR-based approach covering the entire murine TCR VA/VB repertoire. The annealing temperatures of the different VA and VB primers with the constant region primers (Ca inner and Cb inner) are reported in the following TABLE 1, the other PCR conditions were the same for all the reactions: initial denaturation for 4 minutes at 94° C.; 35 cycles of 45 seconds denaturation at 94° C., 30 seconds of annealing, 45 seconds of elongation at 72° C. and final elongation 10 minutes at 72° C.

TABLE 1

| Primer name | Sequence | Annealing temperature |
|---|---|---|
| Ca Inner | AGAGGGTGCTGTCCTGAGAC (SEQ. ID. NO.: 31) | Melting temperature 64° C |
| Va1 | CAGCAGAGCCCAGAATCCCT (SEQ. ID. NO.: 32) | 55° C |
| Va2 | TTCCCATGGTACTGGCAGTT (SEQ. ID. NO.: 33) | 50° C |
| Va3/4 | CTKTTCTGGTATGTCCA (SEQ. ID. NO.: 34) | 45° C |
| Va4 | GGTACCCWRMYCTKTTCTGGTA (SEQ. ID. NO.: 35) | 55° C |
| Va5/7 | AYYTYTTCTGGTACAAGCA (SEQ. ID. NO.: 36) | 50° C |
| Va6/12 | ATCTAYTGGTACCGACAGGT (SEQ. ID. NO.: 37) | 50° C |
| Va8 | GTGACCCAGACAGAAGGCCT (SEQ. ID. NO.: 38) | 55° C |
| Va10 | TGCAGTGGTTTTACCAAAG (SEQ. ID. NO.: 39) | 50° C |
| Va11 | AGAATTCCAGGGGCAGC (SEQ. ID. NO.: 40) | 50° C |
| Va15 | GAAAGCCAAACGCTTCTCC (SEQ. ID. NO.: 41) | 50° C |
| Cb inner | GCCAAGCACACGAGGGTAGCC (SEQ. ID. NO.: 42) | Melting temperature 70° C |
| Vb1 | ATCTAATCCTGGGAAGAGCAAAT (SEQ. ID. NO.: 43) | 60° C |
| Vb2 | GGCGTCTGGTACCACGTGGTCAA (SEQ. ID. NO.: 44) | 65° C |
| Vb3 | GTGAAAGGGCAAGGACAAAAAGC (SEQ. ID. NO.: 45) | 65° C |
| Vb4 | GATATGCGAACAGTATCTAGGC (SEQ. ID. NO.: 46) | 60° C |
| Vb5 | ACATAACAAAGGAAAGGGAGAA (SEQ. ID. NO.: 47) | 55° C |
| Vb6 | TCCTGATTGGTCAGGAAGGGCAA (SEQ. ID. NO.: 48) | 65° C |
| Vb7 | TACCTGATCAAAAGAATGGGAGA (SEQ. ID. NO.: 49) | 60° C |
| Vb8 | GTACTGGTATCGGCAGGACAC (SEQ. ID. NO.: 50) | 60° C |
| Vb9 | AGCTTGCAAGAGTTGGAAAACCA (SEQ. ID. NO.: 51) | 60° C |
| Vb10 | GATTATGTTTAGCTACAATAATA (SEQ. ID. NO.: 52) | 50° C |

TABLE 1-continued

| Primer name | Sequence | Annealing temperature |
|---|---|---|
| Vb11 | ACAAGGTGACAGGGAAGGGACAA (SEQ. ID. NO.: 53) | 65° C |
| Vb12 | ACCTACAGAACCCAAGGACTCAG (SEQ. ID. NO.: 54) | 65° C |
| Vb13 | CAGTTGCCCTCGGATCGATTTTC (SEQ. ID. NO.: 55) | 65° C |
| Vb14 | GCCGAGATCAAGGCTGTGGGCAG (SEQ. ID. NO.: 56) | 65° C |
| Vb15 | AGAACCATCTGTAAGAGTGGAAC (SEQ. ID. NO.: 57) | 60° C |
| Vb16 | CATCAAATAATACATATGGGGCA (SEQ. ID. NO.: 58) | 55° C |
| Vb17 | GTAGTCCTGAAAAGGGCACACT (SEQ. ID. NO.: 59) | 60° C |
| Vb18 | CATCTGTCAAAGTGGCACTTCA (SEQ. ID. NO.: 60) | 60° C |
| Vb19 | AGACATCTGGTCAAAGGAAAAG (SEQ. ID. NO.: 61) | 55° C |

PCR products were cloned by TOPO TA cloning system (Invitrogen®) into pCR-4 TOPO vector (Invitrogen®) and sequenced. Sequences were compared with an Immunogenetics database (The European Bioinformatics Institute, Cambridge, UK) to identify the VA/VB usage for each TCR gene HCV Replicon Cells Hepatoma Huh-7-Lunet cells designated Lunet-HlaA2-neoET, Lunet-Blr/neo ET or Lunet-HlaA2 (neo) were generated by similar protocol as described earlier. See Kantzanou, M., et al. (2003) Viral escape and T cell exhaustion in hepatitis C virus infection analysed using Class I peptide tetramers, Immunol Lett 85:165-71, which is hereby incorporated by reference in its entirety. The Lunet-HlaA2-neoET has ectopic HLA-A2 expression and a selectable HCV subgenomic RNA replicon of genotype 1b, harboring replication enhancing mutations in NS3 and NS4B (Con1-ET). The control replicon cell line Lunet-blr/neo ET is the same as above but transduced with an empty viral vector without the HLA-A2 gene. Both were maintained in DMEM medium supplemented with 10% FCS, non-essential amino acids, glutamine and Pen/Strep, with addition of blasticidin S hydrochloride (3 μg/ml) and G418 (1 mg/ml). Lunet-HlaA2 expressing HLA-A2 under blasticidin selection but without HCV replicon were maintained in the same DMEM medium as above but with 3 μg/ml of blasticidin S hydrochloride and no G418. For the co-culture experiments the Lunet, cells were washed and re-seeded one day before in fresh medium without the antibiotic selection. All medium and supplements were purchased from Invitrogen®, Carlsbad, Calif., USA.

Example 2

This example describes some of the experiments that were performed using the materials and methods set forth in Example 1 to discover the HCV-specific TCRs described herein.

Production and Functional Analysis of $NS3_{1073}$ Specific Hybridomas

By fusing $NS3_{1073}$ specific CD8+ T cells isolated from pVax-NS3-immunized HLA-A2 transgenic mice (HHD) with TCR− BW cells, nine stable HHD-restricted IL-2+ IFN-g+ T-cell hybridomas with specificity to the conserved human HLA-A2 restricted $NS3_{1073}$ CTL epitope were selected (TABLE 2). These immortalized hybridoma cell lines secreted up to nanograms of mouse IL-2 within 24 hours upon stimulation with $NS3_{1073}$ loaded HHD-spleenocytes (FIG. 1A). The overnight IL-2 production ranged from 17 to 34 fold over the non-peptide control targets (3000-5000 pg/ml vs <150 pg/ml). The reactivity is CD8-independent since BW-derived hybridomas lack the CD8 co-factor. See Rock, K. L., et al. (1990) Generation of class I MHC-restricted T-T hybridomas, J Immunol 145:804-11, which is hereby incoporated by reference in its entirety.

TABLE 2

Summary of Stepwise Hybridoma Clone Selection

| Total HAT Clones | Total CD3 Clones | Total IL-2 Clones | Static IL-2 and IFN-g Clones |
|---|---|---|---|
| 108 (100%) | 95 (87.9%) | 21 (19.4%) | 9 (83%) |

Figure 3:
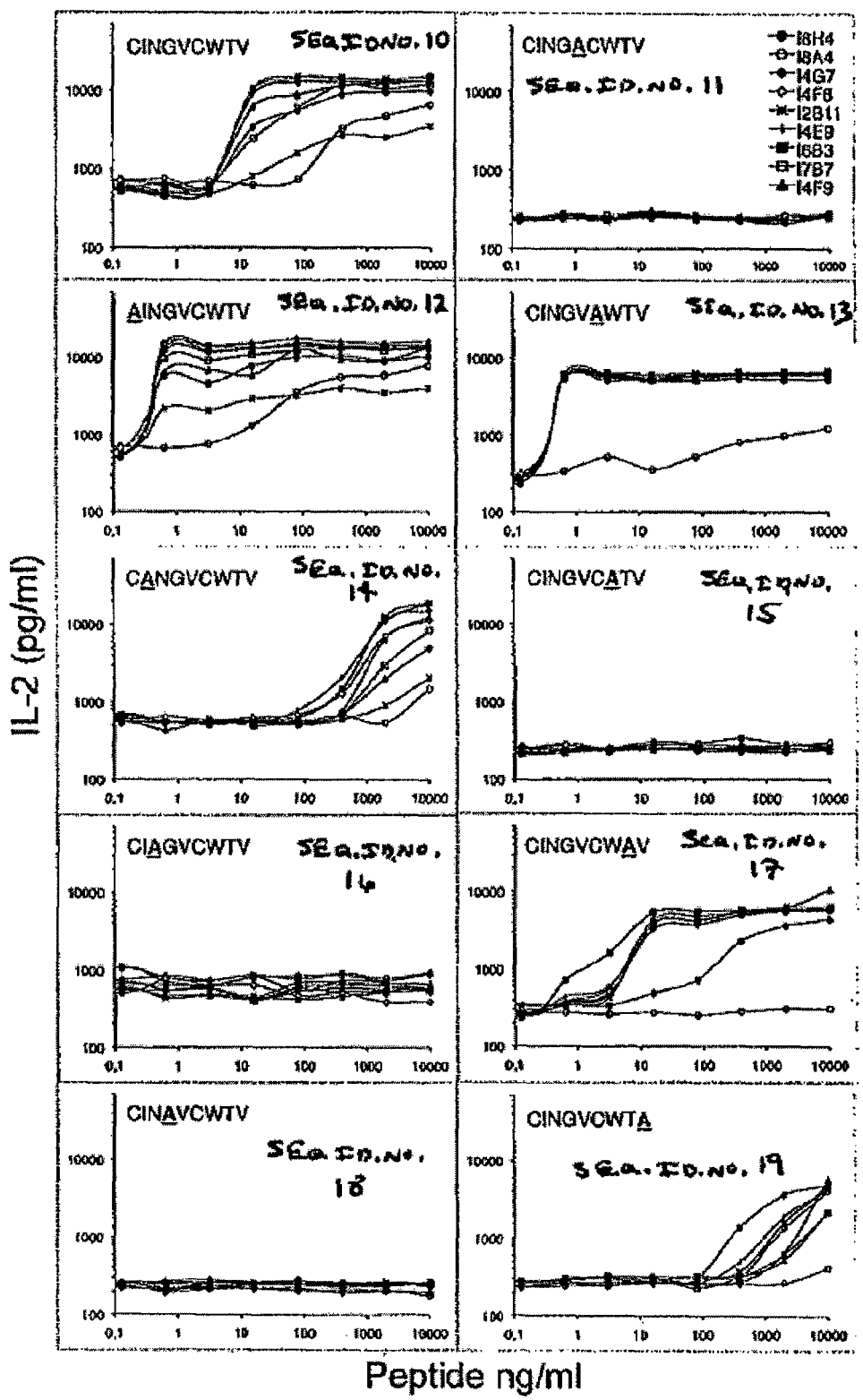
FIG. 3 Functional avidity to wild type $NS3_{1073}$ and the 9 mutant peptide analogs (SEQ. ID. NOS.: 12-19). IL-2 production in hybridoma co-cultures with T2 cells that are loaded with titrating amounts of the wild type $NS3_{1073}$ and the respective peptide analogue that is mutated (alanine substitution) at indicated position (pos 1 to 9). Average values of duplicate co-cultures are shown.

HHD is a human/mouse chimeric molecule, comprised of the HLA-A2.1a1a2b2m and the mouse H-2D$^b$ a3m, transmembrane and cytoplasmic domains. See Pascolo, S., N. et al., (1997) HLA-A2.1-restricted education and cytolytic activity of CD8(+) T lymphocytes from beta2 microglobulin (beta2m) HLA-A2.1 monochain transgenic H-2Db beta2m double knockout mice. J Exp Med 185:2043-51, which is hereby incorporated by reference in its entirety. To assess the recognition of $NS3_{1073}$ on human cell targets, these murine hybridomas were incubated with T2 cells that are a TAP deficient HLA-A2+ lymphoblastic cell line, which allows effective exogenous loading of peptide. As shown in FIG. 1B, T2 loaded with the $NS3_{1073}$ demonstrated a marked IL-2 and IFN-g secretion that was 7-43 and 4-12 folds respectively over the unloaded controls. T2 loaded with the negative control $NS3_{1406}$ (KLVALGINAV (SEQ. ID. NO.: 62)) peptide was not recognized (FIG. 1B AND C). Whilst no major difference was observed in the HHD-restricted response there was some variation in their response to the HLA-A2.01+ human T2 targets. In particular the hybridoma I8A4 was repeatedly found to be a low responder toward the $NS3_{1073}$ loaded T2 (FIG. 1C) as well as the C1R-A2 and HUH-6 targets (FIG. 6D) in comparison to the other clones. Compared to other clones, the functional avidity of the I8A4 also differed from the others and it was noted that it required up to 400 ng/ml peptide/ml to obtain 50% of maximal cytokine production. A few ng/ml of peptide loading was sufficient to stimulate the I4G7 and I4F8 to reach 50% of max cytokine secretion. The I8A4 represents a low functional avidity hybridoma, in comparison to the I4G7, I4G7, I4F8, I4E9, I6B3 and I4F9, which show characteristics resembling high functional avidity T cells (e.g., are reactive at <100 ng peptide/ml) (FIG. 1D and FIG. 3).

TCR Va and Vb Gene Sequencing and Affinity to NS3 Pentamer

Figure 2:
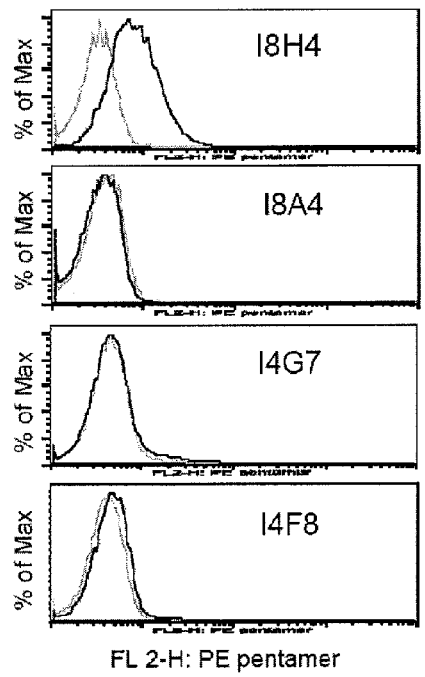
FIG. 2 (A) TCR alpha and beta chain CDR3 region of the indicated hybridoma clone. I8H4 alpha chain (SEQ ID NO. 1) and I8H4 beta chain (SEQ ID NO. 2); I8A4 alpha chain (SEQ ID NO. 3) and I8A4 beta chain (SEQ ID NO. 4); I4G7 alpha chain (SEQ ID NO. 5) and I4G7 beta chain1 (SEQ ID NO. 6) and I4G7 beta chain2 (SEQ ID NO. 7); and I4F8, I2B11, I4E9, I6B3, and I7B7, I4F9 alpha chain (SEQ ID NO. 8) and I4F8, I2B11, I4E9, I6B3, and I7B7, I4F9 beta chain (SEQ ID NO. 9). (B) Affinity to the $NS3_{1073}$/HLA-A2 pentamer. Hybridomas were stained at room temperature for 15 min with PE-labeled $NS3_{1073}$/HLA-A2 pentamer (black line unfiled) or PE-labeled HBVcore control pentamer (grey filled), then stained with FITC-labeled anti-mouse CD3 antibody. The fluorescence intensity was quantified by FACS analysis. Histograms of fluorescence intensity in pentamer staining is gated on live CD3+ population.

The TCR gene sequence of the selected hybridoma T-cell lines was then determined. Rearranged alpha respectively beta chain TCR genes from these hybridomas were identified and were grouped into four individual TCR clones when aligned side-by-side. As shown in FIG. 2A, unique CDR3 coding regions were found in all clones sequenced. It was also noted that the I4G7 had two different beta chains that are encoded by the BV13.1-JB1.3 and VB13.3-BD2-BJ2.4 in addition to the alpha chain (AV9-AJ27). The clones I4F8, I2B11, I4E9, I6B3, I7B7 and I4F9 appear to be sister clones sharing same TCR.

One factor that can have an impact on the T cell function is its TCR's affinity to the peptide-HLA complex. Lack of CD8 co-receptor expression may enable a CD8-independent stabilization of the TCR-peptide/HLA complex. See Roszkowski, J. J., et al., (2003) CD8-independent tumor cell recognition is a property of the T cell receptor and not the T cell, J Immunol 170:2582-9, which is hereby incorporated by reference in its entirety. Because BW hybridomas lack CD8 co-factor it was not clear whether any of these TCRs were capable of binding the $NS3_{1073}$ pentamer. This was confirmed by incubating the four TCR clones individually with an R-PE-labeled $NS3_{1073}$/HLA-A2 pentamer. The fluorescence was quantified in a flow cytometry analysis along with a negative control pentamer (HBVcore$_{18-27}$-HLA-A*201). As shown in FIG. 2B, the I8H4 TCR (AV16/BV13.1) but not the others demonstrated an increase in fluorescence intensity with $NS3_{1073}$ pentamer staining. Thus, in spite of the lack of CD8 co-factor, the I8H4 had an affinity to the $NS3_{1073}$ pentamer.

Cross-Genotype Reactivity

Figure 5:
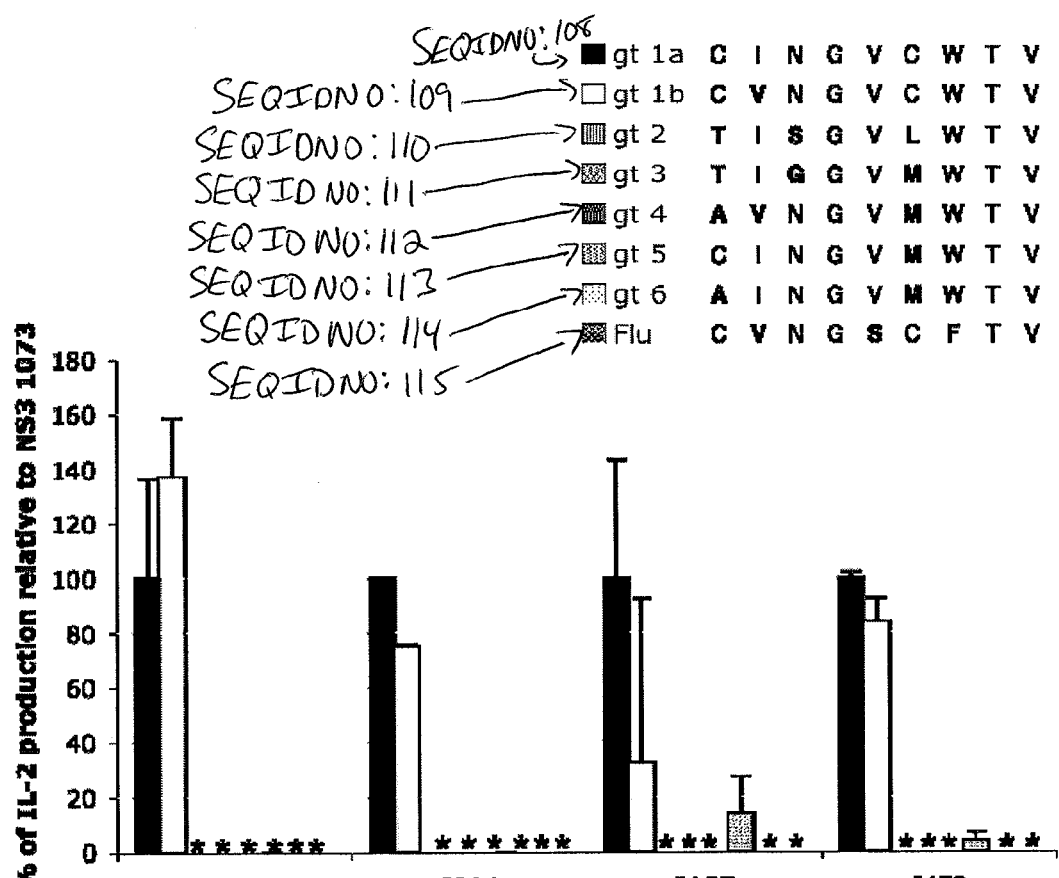
FIG. 5 Cross-reactivity against other viral peptides that share homology to the $NS3_{1073}$ peptide sequence encoded by the DNA vaccine (genotype 1a). Overnight IL-2 production in T-BW hybrid clones against T2 cells loaded with indicated viral peptide (10 μg/ml peptide) was measured for each T cell clone and given as percentage to that against the genotype 1a of $NS3_{1073}$ peptide. Amino acids that differ from the genotype 1a are indicated in bold. Co-cultures were done in triplicates.

Cross-reactivity studies were completed against other viral peptides in particular the natural occurring genotypes of $NS3_{1073}$ and the Flu neuraminidase Flu-$NA_{231}$ to which cross-reactivity to $NS3_{1073}$ of 1b strain has been described. FIG. 5 shows T cell clones IL-2 production when cultured with SEQ ID NOS. 108-115, respectively. Only T-cells cultured with the genotype 1a and 1b of the $NS3_{1073}$ peptide exhibit substantial IL-2 production. None of the other HCV genotype peptide variants tested was sufficiently stimulatory to induce substantial IL-2 production although all variants displayed significant binding affinity to the HLA-A2 molecule. No IL-2 production was found against the Flu NA peptide (SEQ ID NO: 115), or other viral peptides including the HCV $NS5_{2221}$ (SEQ ID NO: 116), $NS5_{1992}$ (SEQ ID NO: 117), and HCMV $pp65_{495}$ (SEQ ID NO: 118). The results suggest these T cell clones are highly specific for the genotype 1 of HCV NS3.

Single Amino Acid Mutation in $NS_{1073}$ Peptide does not Impair Binding to HLA-A2.1

Observations in human CTLs from acute HCV infection indicate that addition to anchor positions (2, 7 and 9) that help to stabilize the peptide-HLA complex, the amino acid residues at positions (3, 4 and 5) in $NS3_{1073}$ may support the interaction with the TCR (45). To test the tolerability to a.a. mutations in $NS3_{1073}$ epitope, hybridomas were stimulated with saturated amount of alanine substituted peptide analogues (10 µg/ml). As shown in FIG. 4A, the reactivity in I8A4 hybridoma (low functional avidity) was severely compromised in each substituted position, except at position 1. Meanwhile, the hybridoma I8H4, I4G7, I4F8 and the others sister clones with same TCR were comparably less sensitive to mutation, only position 3, 4, 5 and 7 were found to be critical for their function. This provided strong evidence that that these clones have a higher functional avidity.

The amount of mutant peptides was titrated and it was observed that reduction in peptide density further impaired the functional avidity in most hybridomas. As shown in FIG. 4B, it was found that up to pg level of mutant peptide 2, 3, 4, 5, 7 and 9 was often required to obtain an EC50 IL-2 secretion to that of the wt response. One exception was the I4G7 (high functional avidity) hybridoma that appeared to tolerate a.a. change in position 2, to which other hybridomas are sensitive to (EC50: 80 ng/ml vs up 2 µg/ml for the others).

Figure 6:
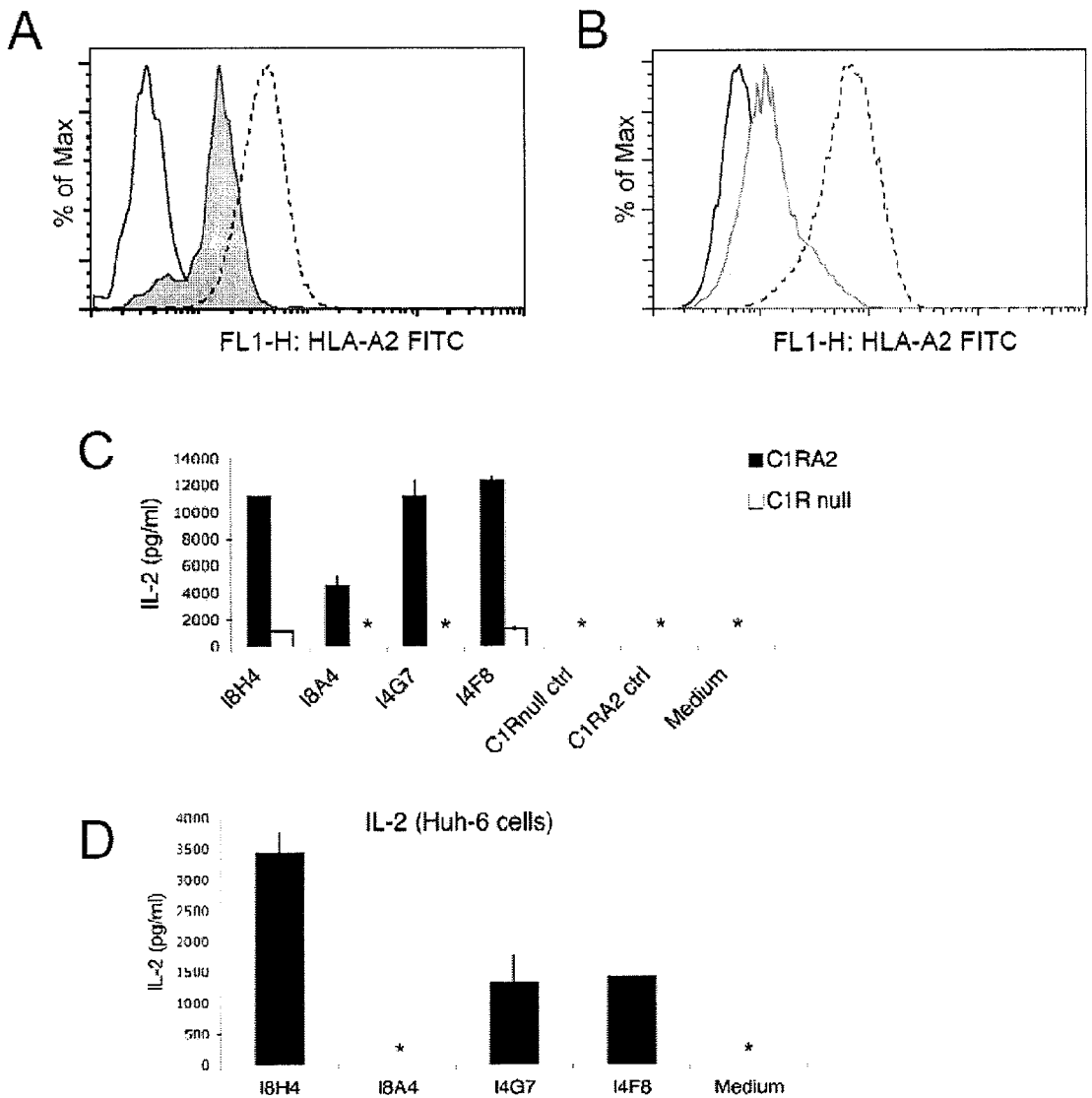
FIG. 6 HLA-A2 expression in the B-lymphocyte C1R-A2 cell line (A, filled grey) and the hepatoblastoma Huh6 cell line (B, filled grey) loaded with $NS3_{1073}$ peptide compared to that of the C1R-null cells (solid line no fill) and T2 cells (dotted line). (C+D) IL-2 secretion in T-BW hybrid clones following co-culture with (C) C1RA2 cells or C1R null cells or (D) HuH-6 cells loaded with 10 µg/ml of NS3$_{1073}$ peptide. Average values and standard deviation of duplicate co-cultures are shown. Comparative results were obtained in two separate experiments.

Reactivity to $NS3_{1073}$ Peptide Loaded on Other Target Cells with HLA-A.2 Expression A constitutive HLA-A.2 expression and TAP deficiency in T2 cells favor an efficient loading of exogenous peptide, it was thus desired to determine whether peptide recognition by the hybridomas was not restricted only to this target cell line. For further verification of hybridoma integrity, they were tested on C1R cells normal or defective of HLA A2 expression (C1R.A2 and C1R.null), as well as Huh-6 cell lines. In contrast to T2 cells, the C1R.A2 has no defect in tap transporter protein (TAP), endogenous peptides preoccupying MHC molecules are stripped by a mild acid treatment to accommodate exogenous peptide antigens. The HLA-A2.01 density quantified after $NS3_{1073}$ loading by flow cytometry sorting demonstrate that the HLA-A2 expression does not reach same level as that of T2 but is clearly positive compared with the control cell line defective of HLA-A2 (C1R.null) expression (FIG. 6A). The Huh-6 showed the lowest HLA-A2 expression, as only a fraction of the cells were positive for the staining as compared to the negative control C1R.null cell line (FIG. 6B). As shown in FIG. 6C, the hybridomas co-cultured with $NS3_{1073}$ peptide loaded C1R-A2 cells secreted IL-2 at the same magnitude as that observed for T2 targets. Significant IL-2 release against the peptide-loaded Huh-6 cells was present in the I8H4, I4G7, and I4F8 clones (FIG. 6D).

Figure 7:
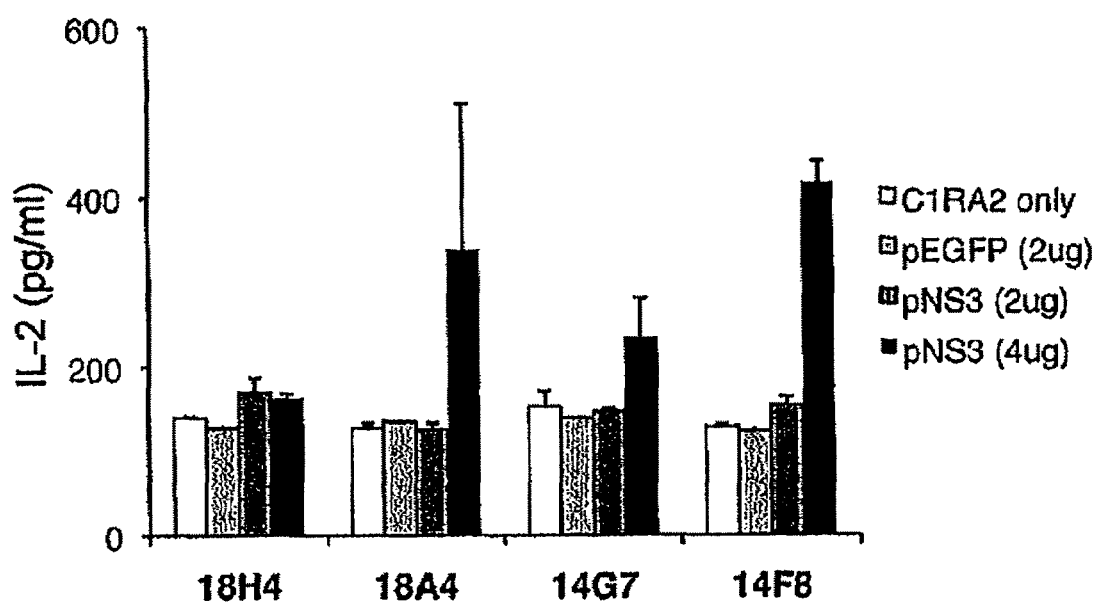
FIG. 7 IL-2 secretion upon co-culture with C1R-A2 transfected with pNS3 plasmid. Hybridomas were co-cultured with C1R-A2 cells transiently transfected or not with pNS3 (2 or 4 µg) plasmid or pEGFP (4 µg) control. Data represent mean values and standard errors of the amount of IL-2 detected in duplicate co-cultures. Comparative results were obtained in two separate experiments.

Moreover as shown in FIG. 7, the hybridomas recognize pNS3-transfected C1R-A2 (transfection efficiency 1-2%), in which I8A4, I4G7 and I4F8 secreted certain levels of IL-2 that is markedly over the cut-off (mean value of IL-2 in pEGFP control+3 SD). Thus, it was determined that the target recognition function in these hybridomas is mediated in an HLA-A.2-dependent manner. The data also provide evidence that an efficient IL-2 release was obtained in the presence of lower MHC expression or low target cell frequency.

Reactivity Against HCV RNA Replicon Hepatoma cells

Figure 8:
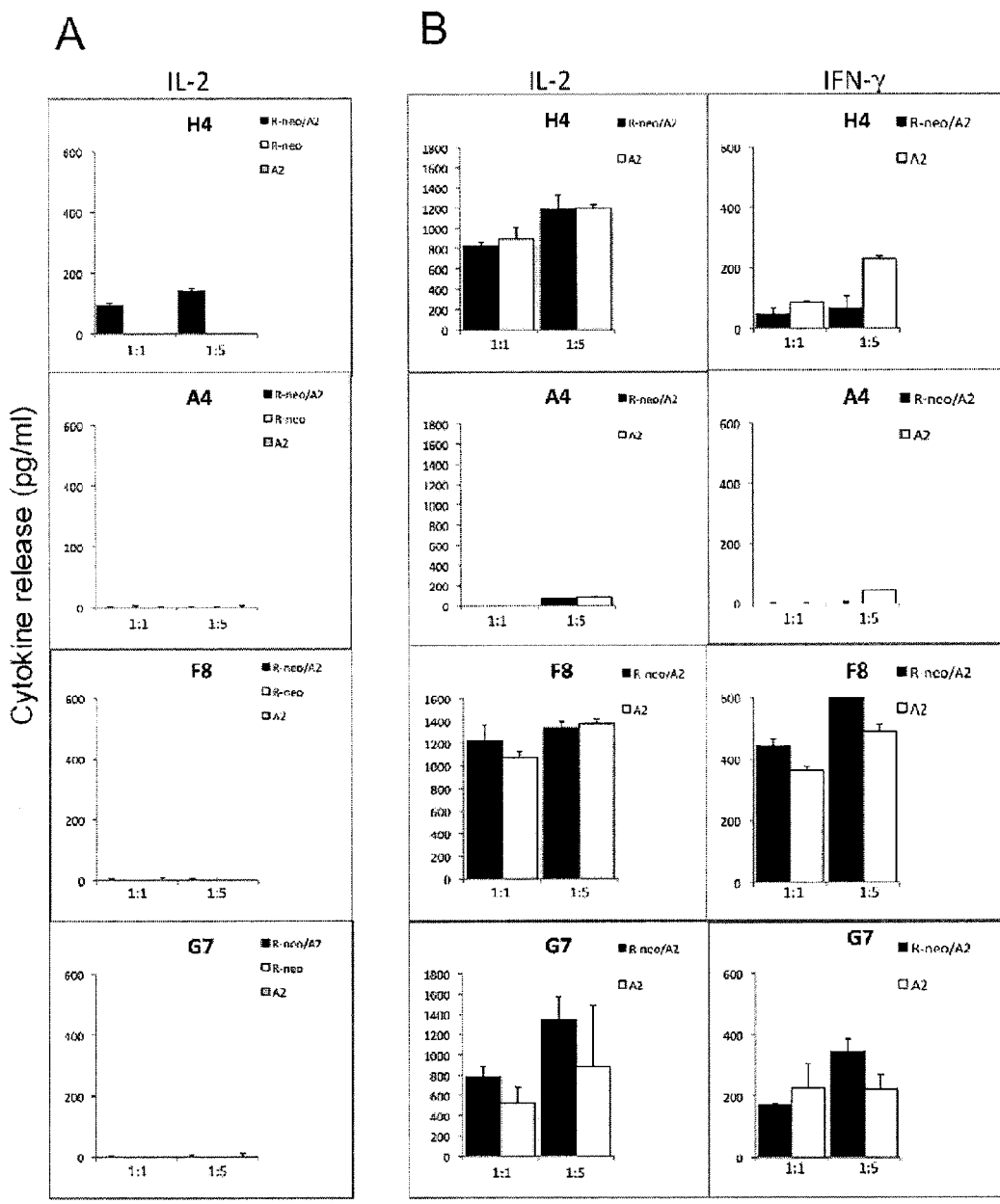
FIG. 8 Cytokine release against the Huh7/Lunet-derived HCV replicon cells. A) IL-2 concentration in T-BW hybrid clone I8H4 (H4), I8A4 (A4), I4G7 (G7) or I4F8 (F8) co-cultured with the Lunet-HlaA2-neoET (R-neo/A2) replicon cells that harbor both HCV Con1-ET subgenomic replicon and HLA-A2, or co-cultured with control cell lines Lunet-blr/neo ET (R-neo) or Lunet-HlaA2 neo (A2) that harbor only HCV replicon or HLA-A2, respectively. B) IL-2 and IFN-γ concentration in the T-BW hybrid clones co-cultured with Lunet-HlaA2-neoET (R-neo/A2) HCV replicon cells, or the control Lunet-HlaA2 neo (A2) cells that express HLA-A2 but no HCV replicon, that were loaded with NS3$_{1073}$ peptide (gt1a, 10 µg/ml). Co-cultures consisted of 1×10$^5$ of indicated Lunet cells and T-BW cells in ratio 1:1 or 1:5. The cytokine production was measured by ELISA. Average values and standard deviation of duplicate co-cultures are shown.

As shown in FIG. 8B, an antigen-specific IL-2 production by the T cell clones was detected after co-culture in different ratios with peptide- ($NS3_{1073}$ gt 1a, SEQ ID NO: 108) loaded HCV replicon cells harboring both Con1-ET replicon and HLA-A2 (R-neo/A2) or control cells expressing only the HLA-A2 (A2). In these cultures both IL-2 and IFN-γ were detected, in particularly from the high avidity I8H4 (H4), I4G7 (G7) and I4F8 (F8) T cell clones and indicates that the lentiviral transferred HLA expression is functional.

A shown in FIG. 8A, IL-2 production was detected in the co-culture of the I8H4 (H4) and HLA-A2-positive HCV replicon cells (R-neo/A2), and the IL-2 production was dependent on the ratio of the added cells. No IFN-γ was detected. Stimulation with HCV replicon cells without HLA-A2 expression or cells with HLA-A2 expression only did not stimulate any IL-2 release from the I8H4.

Example 3

This example describes some of the experiments that were performed to discover the HCV-specific TCRs for NS5 peptides.

Human HLA (HHD) transgenic mice were immunized with a DNA construct encoding NS5 1992-2000 (SEQ ID NO: 117). The DNA immunization was performed as described in Example 1. Spleenocytes are removed from the immunized transgenic mice fused with TCR⁻BW cells so as to generate immortalized hybridomas. Hybridomas were selected that showed CD3 expression, as well as IL-2 and IFN-g secretion above a threshold level when exposed to NS5$_{1992}$. The selected hybridomas were expanded and poly A+ RNA that encodes the desired TCRs are extracted, purified and cDNA were generated therefrom by RTPCR. The cDNA was then sequenced and cloned as described in Example 1 to obtain VA and VB chain sequences for two receptors: TCR-19 (SEQ ID NO: 88 and SEQ ID NO: 89) and TCR-69 (SEQ ID NO: 96 and SEQ ID NO: 97). Unique CDR3 coding regions were found in the clones: TCR-19 (SEQ ID NO: 104 SEQ and ID NO: 105) and TCR-69 (SEQ ID NO 106 and SEQ ID NO: 107) (FIG. 9).

Example 4

This example describes an approach to make TCRs to a desired candidate peptide. Accordingly, human HLA (HHD) transgenic mice are immunized with a DNA construct encoding a candidate peptide (e.g., a hepatitis peptide such as NS5, HBV core peptide, a birch antigen peptide, or a Japanese Encephalitis Virus (JEV) peptide). Preferably, the DNA immunization is performed in conjunction with electroporation and may include one or more adjuvants. Spleencocytes are removed from the immunized transgenic mice and screened for CTLs that are specific for the candidate peptide. The identification of CTLs specific for the candidate peptide is performed by contacting the CTLs with the candidate peptide and/or cells loaded with the peptide and measuring the production of interferon-gamma, and/or chromium$^{51}$ release. T cells that express at least 1000 pg/ml of interferon gamma when exposed to low levels of candidate peptide and/or cells loaded with the peptide are selected for further processing. Once populations of CTLs that are specific for the candidate peptide are identified, they are fused with TCR⁻BW cells so as to generate immortalized hybridomas. The immortalized hybridomas are expanded and poly A+ RNA that encodes the desired TCRs are extracted, purified and cDNA is generated therefrom by RTPCR. The cDNA is then sequenced and cloned into an expression construct, preferably a lentiviral expression system (Invitrogen® or Orbigen Inc.), which can then be transferred to a packaging cell line (Phoenix systems, Orbigen Inc.). That is, the resulting expression cassette harboring the genes encoding TCR alpha chain, a 2A protease motif, and TCR beta chain are assembled and cloned into a mammalian expression vector, preferably, the pLPCX vector from Clonetech® (e.g., the pLPCX vector from Clonetech® and the TCRalpha chain-2A autocleavaging protease-TCRBeta chain system can be used). Retroviral vectors isolated from the expression system are then used to infect stimulated T cells (preferably T cells isolated from a subject in need of a TCR specific for the candidate peptide that have been stimulated with a growth factor such as IL-2) so as to generate said TCRs. The ability of the TCRs to interact with the candidate peptide is then determined using the aforementioned interferon-gamma and chromium$^{51}$ release assays after stimulation with the peptide and/or cells loaded with the peptide.

Example 5

This example describes an approach that can be used to provide T cells that are specific for an HCV peptide to a subject in need of an agent that inhibits the proliferation of HCV. Accordingly, a TCR specific for an HCV peptide (e.g., an NS3 peptide such as, 1073-1081) is generated by providing a DNA construct encoding said peptide and immunizing human HLA (HHD) transgenic mice with said DNA, preferably in the presence of an adjuvant and/or electroporation. Spleenocytes are obtained from said immunized mice and CTLs specific for the HCV peptide (e.g., an NS3 peptide such as 1073-1081) are identified (e.g., by measuring production of an immune response molecule such as, interferon gamma or chromium$^{51}$ release in the presence of the peptide and/or cells loaded with the peptide). CTLs specific for the HCV peptide (e.g., an NS3 peptide such as, 1073-1081) are then fused to TCR⁻BW cells to obtain immortalized hybridomas. RTPCR is then performed (e.g., using oligonucleotides disclosed in TABLE 1). The individual PCR products are inserted into an expression construct (e.g or a commercially available vector from Invitrogen® or Orbigen Inc). The resulting expression cassette harboring the genes encoding TCR alpha chain, a 2A protease motif, and TCR beta chain are assembled and cloned into a mammalian expression vector, preferably, the pLPCX vector from Clonetech®. That is, preferably, the pLPCX vector from Clonetech® and the TCRalpha chain-2A autocleavaging protease-TCRBeta chain system is used. Optionally, the construct contains an HSV-TK gene driven by a promoter (e.g., a constitutive promoter such as, SV40, actin or CMV). The construct comprising the DNA that encodes the HCV-specific TCR and, optionally, the HSV-TK gene is then transfected into a packaging cell line so as to obtain retroviral vectors (e.g., a commercially available packaging cell line such as Phoenix Eco of Orbigen Inc. or one from Invitrogen®). After co-culture, the packaging cells are removed from the culture (e.g., by negative selection with magnetic beads conjugated with anti-LYT-2 antibodies). The clones are expanded and high titer clones are selected by dot-blot titration. Southern blotting can be performed to confirm vector integration and copy number.

T cells from a patient in need of an agent that inhibits HCV proliferation are then obtained. Peripheral blood lymphocytes (PBL) are collected by leukophoresis, and lymphocytes are separated by centrifugation on a Ficoll/Hypaque cushion, washed in buffer, then resuspended at a concentration of approximately 1×10$^6$/ml in medium, preferably serum-free. The lymphocytes are stimulated with a growth factor (e.g., IL-2, and/or CD3). The lymphocytes are cultured in vitro for 10, 24, 36, or 48 hours before transduction. Following stimulation, lymphocytes are transduced with the retroviral vectors by transfer to culture dishes that are precoated with retroviral vectors. To coat culture plates with the vectors, nontissue culture-treated six-well plates are first treated with recombinant fibronectin fragment (RetroNectin®, Takara, Otsu, Japan). To these plates retroviral vector supernatant is added, the procedure may be repeated the following day, after which time cells may be expanded in an incubator and split as necessary to maintain cell density between approximately 0.5×10$^6$ cells/ml and 4×10$^6$ cells/ml. The reactivity of the transfected T cells is then, preferably, measured by analyzing the production of interferon gamma or chromium$^{51}$ release in the presence of the HCV peptide and/or cells loaded with the peptide.

The transfected T-cells can then be purified from the culture medium, suspended in a pharmaceutically acceptable buffer or excipient and administered to the subject (e.g., intravenously). Preferably, from about 10$^8$ to about 10$^{12}$ transduced T cells are provided to a human. In some embodiments, the inoculated subject is preferably also provided IL-2, and more preferably a high-dose of IL-2. At a time appropriate to stop the T cells from proliferating, provided the T cells contain HSV-TK, acyclovir or gancyclovir is provided to the subject. Optionally, the amount of inhibition of proliferation of HCV is measured after treatment and/or at different times after treatment. Such measurements can be made virologically (e.g., by detecting the level of HCV RNA in the blood of the patient).

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. An isolated nucleic acid comprising a sequence encoding a peptide that comprises the sequence of SEQ ID NO:1, wherein said isolated nucleic acid is codon-optimized for expression in humans.

2. The isolated nucleic acid of claim 1, wherein said isolated nucleic acid comprises SEQ ID NO:76.

3. The isolated nucleic acid of claim 1, wherein said isolated nucleic acid comprises SEQ ID NO:78.

4. An isolated cell comprising the isolated nucleic acid of claim 1.

5. The isolated cell of claim 4, wherein said isolated nucleic acid comprises SEQ ID NO:63.

6. The isolated cell of claim 4, wherein the peptide that comprises the sequence of SEQ ID NO: 1 comprises the sequence of SEQ ID NO:72.

7. The isolated cell of claim 4, wherein said isolated nucleic acid comprises SEQ ID NO:74.

8. The isolated cell of claim 4, wherein said isolated nucleic acid comprises SEQ ID NO:76.

9. The isolated cell of claim 4, wherein said isolated nucleic acid comprises SEQ ID NO:78.

10. A host-expression vector comprising the isolated nucleic acid of claim 1.

11. The host-expression vector of claim 10, wherein said isolated nucleic acid comprises SEQ ID NO:63.

12. The host-expression vector of claim 10, wherein said peptide that comprises the sequence of SEQ ID NO:1 comprises the sequence of SEQ ID NO:72.

13. The host expression vector of claim 12, wherein said isolated nucleic acid comprises SEQ ID NO:74.

14. The host-expression vector of claim 12, wherein said isolated nucleic acid comprises SEQ ID NO:76.

15. The host-expression vector of claim 12, wherein said isolated nucleic acid comprises SEQ ID NO:78.

16. The isolated nucleic acid of claim 1, wherein said nucleic acid further comprises a nucleic acid sequence encoding a peptide that comprises the sequence of SEQ ID NO:2.

17. The isolated nucleic acid of claim 16, wherein said isolated nucleic acid comprises SEQ ID NO:64.

18. The isolated nucleic acid of claim 16, wherein the sequence that encodes SEQ ID NO:2 encodes SEQ ID NO:73.

19. The isolated nucleic acid of claim 18, wherein said isolated nucleic acid comprises SEQ ID NO:75.

20. The isolated nucleic acid of claim 16, wherein said isolated nucleic acid comprises SEQ ID NO:77.

21. The isolated nucleic acid of claim 16, wherein said isolated nucleic acid comprises SEQ ID NO:79.

22. The isolated nucleic acid of claim 16, wherein the isolated nucleic acid that encodes SEQ ID NO: 1 and that encodes SEQ ID NO:2 further encodes a 2A protease cleavage site positioned between SEQ ID NO: 1 and SEQ ID NO:2.

23. The isolated nucleic acid of claim 1, wherein said isolated nucleic acid comprises SEQ ID NO:63.

24. The isolated nucleic acid of claim 1, wherein said peptide that comprises the sequence of SEQ ID NO:1 comprises the sequence of SEQ ID NO:72.

25. The isolated nucleic acid of claim 1, wherein said isolated nucleic acid comprises SEQ ID NO:74.

* * * * *